(12) United States Patent
Matthews

(10) Patent No.: US 9,974,846 B2
(45) Date of Patent: May 22, 2018

(54) RECOMBINANT TRYPANOSOMA THEILERI PARASITE

(75) Inventor: Keith Roland Matthews, Edinburgh (GB)

(73) Assignee: THE UNIVERSITY COURT OF THE UNIVERSITY OF EDINBURGH, Edinburgh (GB)

( * ) Notice: Subject to any disclaimer, the term of this patent is extended or adjusted under 35 U.S.C. 154(b) by 0 days. days.

(21) Appl. No.: 13/813,100

(22) PCT Filed: Jul. 29, 2011

(86) PCT No.: PCT/GB2011/001154
§ 371 (c)(1),
(2), (4) Date: May 6, 2013

(87) PCT Pub. No.: WO2012/013939
PCT Pub. Date: Feb. 2, 2012

(65) Prior Publication Data
US 2013/0216578 A1    Aug. 22, 2013

Related U.S. Application Data

(60) Provisional application No. 61/370,223, filed on Aug. 3, 2010.

(30) Foreign Application Priority Data

Jul. 29, 2010   (EP) ..................................... 10171304

(51) Int. Cl.
| | | |
|---|---|---|
| *C12N 15/00* | (2006.01) | |
| *A61K 39/005* | (2006.01) | |
| *A61K 39/00* | (2006.01) | |
| *C07K 14/44* | (2006.01) | |

(52) U.S. Cl.
CPC ............ *A61K 39/005* (2013.01); *A61K 39/00* (2013.01); *C07K 14/44* (2013.01); *A61K 2039/523* (2013.01)

(58) Field of Classification Search
USPC ........................... 424/269.1; 435/71.2, 320.1
See application file for complete search history.

(56) References Cited

U.S. PATENT DOCUMENTS

2004/0092467 A1   5/2004   Chang et al.

FOREIGN PATENT DOCUMENTS

| | | |
|---|---|---|
| EP | 0473210 | 3/1992 |
| WO | WO1998011245 | 3/1998 |
| WO | WO2000032796 | 6/2000 |
| WO | WO2001032896 | 5/2001 |
| WO | WO2004026903 | 4/2004 |
| WO | WO2004044184 | 5/2004 |
| WO | WO2004054969 | 7/2004 |

OTHER PUBLICATIONS

Clayton, C.E. "Genetic manipulation of kinetoplastida." *Parasitology Today*, vol. 15, No. 9, pp. 372-378. Sep. 1999.
Roland et al. *Current Opinion in Molecular Therapeutics*, vol. 7, pp. 62-72. 2005.
Panicali et al. "Construction of poxviruses as cloning vectors: insertion of the thymidine kinase gene from herpes simplex virus into the DNA of infectious vaccinia virus." *Proceedings of the National Academy of Sciences of the USA*, vol. 79, pp. 4927-4931. 1982.
Vermeulen, A.N. "Progress in recombinant vaccine development against coccidiosis: A review and prospects into the next millennium." *International Journal for Parasitology*, vol. 28, pp. 1121-1130. 1998.
Bose et al. "Characterization of Megatrypanum trypanosomes from European cervidae." *Parasitology*, vol. 107, iss. 1, pp. 55-61. 1993.
Rodrigues et al. "Phylogeny of Trypanosoma (Megatrypanum) theileri and related trypanosomes reveals lineages of isolates associated with artiodactyl hosts diverging on SSU and ITS ribosomal sequences." *Parasitology*, vol. 132, pp. 215-224. 2006.
Bose et al. "Transmission of *Trypanosoma theileri* to cattle by Tabanidae." *Parasitology Research*, vol. 73, pp. 421-424. 1987.
Morzaria et al. *Veterinary Parasitology*, vol. 19, pp. 13-21. 1986.
Tielens et al. "Surprising variety in energy metabolism within Trypanosomatidae." *Trends in Parasitology*, vol. 25, pp. 482-490. 2009.
Lamy et al. *Bulletin de l'Academie Veterinaire de France*, vol. 40, pp. 323-325. 1967.
Ward et al. *Australian Veterinary Journal*, vol. 61, p. 324. 1984.
Doherty et al. *Vet. Rec.*, vol. 132, p. 653-656. 1993.
Clayton et al. "Tests of heterologous promoters and intergenic regions in Leishmania major." *Molecular & Biochemical Parasitology*, vol. 105, pp. 163-167. 2000.
El-Sayed et al. "Comparative genomics of trypanosomatid parasitic protozoa." *Science*, vol. 309, p. 404-409. 2005.
Palenchar et al. "Gene transcription in trypanosomes." *Molecular & Biochemical Parasitology*, vol. 146, p. 135-141. 2006.
Eid et al. "Stable Integrative Transformation of Trypanosoma brucei that Occurs Exclusively by Homologous Recombination." *Proceedings of the National Academy of Sciences of the USA*, vol. 88, pp. 2118-2121. 1991.
Kelly et al. "A shuttle vector which facilitates the expression of transfected genes in Trypanosoma cruzi and Leishmania." *Nucleic Acids Research*, vol. 20, pp. 3963-3969. 1992.

(Continued)

*Primary Examiner* — Jennifer E Graser
(74) *Attorney, Agent, or Firm* — Hoxie & Associates LLC

(57) ABSTRACT

The present invention relates to the field of the veterinary medicine of bovine animals. In particular the invention relates to a recombinant *Trypanosoma theileri* parasite, preferably comprising a heterologous nucleic acid sequence that is capable of encoding a protein for instance an antigen, a cytokine, a hormone, an antimicrobial protein, or an antibody. Also disclosed are uses of and methods for making and using the recombinant *T. theileri* parasite in medical or non-curative treatments; in particular as a sustained delivery vector for proteins to bovine animals, e.g. as a vaccine.

3 Claims, 22 Drawing Sheets

(56) References Cited

OTHER PUBLICATIONS

Figure 1:
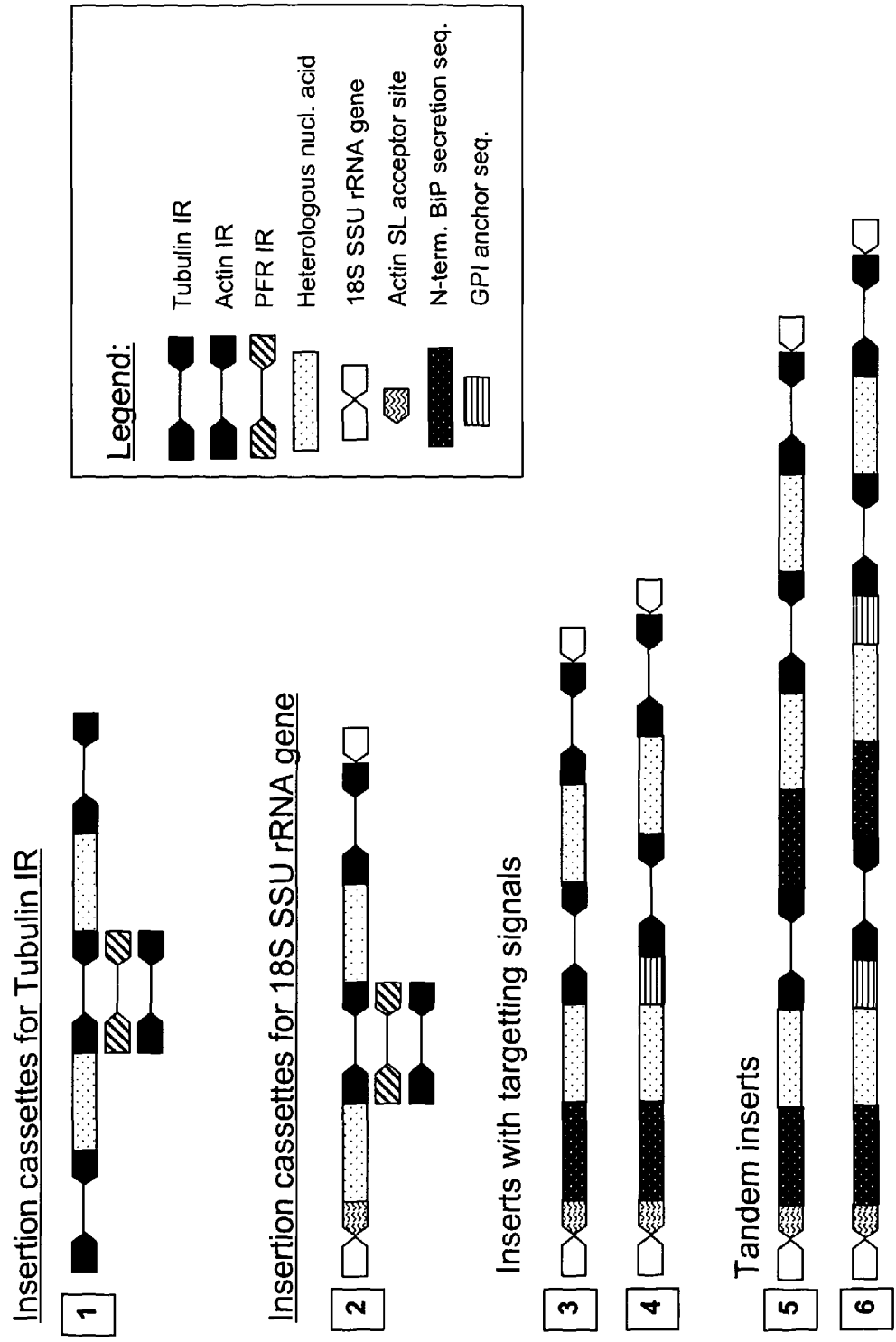

Rodrigues et al. "Characterization of spliced leader genes of Trypanosoma (Megatrypanum) theileri: phylogeographical analysis of Brazilian isolates from cattle supports spatial clustering of genotypes and parity with ribosomal markers." *Parasitology*, vol. 137, pp. 111-122. 2010.

Townsend et al. "Trypanosoma theileri: antibody-dependent killing by purified populations of bovine leucocytes." *Clinical and Experimental Immunology*, vol. 48, pp. 289-299. 1982.

Germain et al. "The biochemistry and cell biology of antigen processing and presentation." *Annual Review of Immunology*, vol. 11, pp. 403-50. 1993.

Geysen et al. *Journal of Immunology Methods*, vol. 102, p. 259-274. 1987.

Good et al. "Construction of synthetic immunogen: use of new T-helper epitope on malaria circumsporozoite protein." *Science*, vol. 235, p. 1059-1062. 1987.

Splitter et al. "Isolation and continuous cultivation of Trypanosoma theileri in media containing tissue culture fluids." *Experimental Parasitology*, vol. 21, pp. 137-148. 1967.

Delbecq et al. "Babesia divergens: cloning and biochemical characterization of Bd37." *Parasitology*, vol. 125, pp. 305-312. 2002.

Hadj-Kaddour et al. "Recombinant protein Bd37 protected gerbils against heterologous challenges with isolates of Babesia divergens polymorphic for the Bd37 gene." *Parasitology*, vol. 134, pp. 187-196. 2007.

Blundell et al. "Targeting of exogenous DNA into Trypanosoma brucei requires a high degree of homology between donor and target DNA." *Molecular & Biochemical Parasitology*, vol. 76, pp. 215-229. 1996.

Martinez-Calvillo et al. "pRIBOTEX expression vector: a pTEX derivative for a rapid selection of Trypanosoma cruzi transfectants." *Gene*, vol. 199, p. 71-76. 1997.

Irmer et al. "Degradation of the unstable EP1 mRNA in Trypanosoma brucei involves initial destruction of the 3'-untranslated region." *Nucleic Acids Research*, vol. 29, pp. 4707-4715. 2001.

Kimura et al. *Biochim. Biophys. Acta*, vol. 1219, p. 653-659. 1994.

Bangs et al. "A soluble secretory reporter system in Trypanosoma brucei. Studies on endoplasmic reticulum targeting." *Journal of Biological Chemistry*, vol. 271, pp. 18387-18393. 1996.

Canfield et al. "Association of thrombospondin-1 with osteogenic differentiation of retinal pericytes in vitro." *Journal of Cell Science*, vol. 109, pp. 343-353. 1996.

Precigout et al. "Association between sequence polymorphism in an epitope of Babesia divergens Bd37 exoantigen and protection induced by passive transfer." *International Journal for Parasitology*, vol. 34, pp. 585-593. 2004.

Matthews, K., et al., "Molecular regulation of the life cycle of African trypanosomes", *Trends in Parasitology*, Jan. 2004, vol. 20 No. 1, pp. 40-47.

Turner, C., et al., "The Use of Experimental Artefacts in African Trypanosome Research", *Parasitology Today*, 1990, vol. 6 No. 1, pp. 14-17.

Turner, C. et al., "Replication, differentiation, growth and the virulence of Trypanosoma brucei infections" *Parasitology*, 1995 vol. 111, pp. 289-300.

International Search Report of International Application No. PCT/GB2011/001154, prepared by the International Search Authority, dated Sep. 30, 2011, 4 pages.

Mott et al., "Targeting Cattle-Borne Zoonoses and Cattle Pathogens Using a Novel Trypanosomatid-Based Delivery System", PLOS Pathogens, Oct. 2011, 7(10):1-9.

SEQUENCE LISTING

```
<160> NUMBER OF SEQ ID NOS: 80

<210> SEQ ID NO 1
<211> LENGTH: 6009
<212> TYPE: DNA
<213> ORGANISM: Artificial Sequence
<220> FEATURE:
<223> OTHER INFORMATION: Transfervector pabCTBba
<220> FEATURE:
<221> NAME/KEY: misc_feature
<222> LOCATION: (1)..(2966)
<223> OTHER INFORMATION: pGEMTeasy plasmid backbone
<220> FEATURE:
<221> NAME/KEY: misc_feature
<222> LOCATION: (3026)..(3581)
<223> OTHER INFORMATION: alpha-beta Tubulin IR
<220> FEATURE:
<221> NAME/KEY: misc_feature
<222> LOCATION: (3590)..(4249)
<223> OTHER INFORMATION: CAT gene
<220> FEATURE:
<221> NAME/KEY: misc_feature
<222> LOCATION: (4258)..(4927)
<223> OTHER INFORMATION: beta-alpha Tubulin IR
<220> FEATURE:
<221> NAME/KEY: misc_feature
<222> LOCATION: (4934)..(5326)
<223> OTHER INFORMATION: BSD gene
<220> FEATURE:
<221> NAME/KEY: misc_feature
<222> LOCATION: (5333)..(6002)
<223> OTHER INFORMATION: beta-alpha Tubulin IR

<400> SEQUENCE: 1
atcactagtg aattcgcggc cgcctgcagg tcgaccatat gggagagctc ccaacgcgtt      60
```

-continued

```
ggatgcatag cttgagtatt ctatagtgtc acctaaatag cttggcgtaa tcatggtcat    120
agctgtttcc tgtgtgaaat tgttatccgc tcacaattcc acacaacata cgagccggaa    180
gcataaagtg taaagcctgg ggtgcctaat gagtgagcta actcacatta attgcgttgc    240
gctcactgcc cgctttccag tcgggaaacc tgtcgtgcca gctgcattaa tgaatcggcc    300
aacgcgcggg gagaggcggt ttgcgtattg ggcgctcttc cgcttcctcg ctcactgact    360
cgctgcgctc ggtcgttcgg ctgcggcgag cggtatcagc tcactcaaag gcggtaatac    420
ggttatccac agaatcaggg gataacgcag gaaagaacat gtgagcaaaa ggccagcaaa    480
aggccaggaa ccgtaaaaag gccgcgttgc tggcgttttt ccataggctc cgcccccctg    540
acgagcatca caaaaatcga cgctcaagtc agaggtggcg aaacccgaca ggactataaa    600
gataccaggc gtttccccct ggaagctccc tcgtgcgctc tcctgttccg accctgccgc    660
ttaccggata cctgtccgcc tttctccctt cgggaagcgt ggcgctttct catagctcac    720
gctgtaggta tctcagttcg gtgtaggtcg ttcgctccaa gctgggctgt gtgcacgaac    780
cccccgttca gcccgaccgc tgcgccttat ccggtaacta tcgtcttgag tccaacccgg    840
taagacacga cttatcgcca ctggcagcag ccactggtaa caggattagc agagcgaggt    900
atgtaggcgg tgctacagag ttcttgaagt ggtggcctaa ctacggctac actagaagaa    960
cagtatttgg tatctgcgct ctgctgaagc cagttacctt cggaaaaaga gttggtagct   1020
cttgatccgg caaacaaacc accgctggta gcggtggttt ttttgtttgc aagcagcaga   1080
ttacgcgcag aaaaaaagga tctcaagaag atcctttgat cttttctacg ggtctgacg   1140 ctcagtggaa cgaaaactca cgttaaggga ttttggtcat gagattatca aaaggatct   1200 tcacctagat ccttttaaat taaaaatgaa gttttaaatc aatctaaagt atatatgagt   1260
aaacttggtc tgacagttac caatgcttaa tcagtgaggc acctatctca gcgatctgtc   1320
tatttcgttc atccatagtt gcctgactcc ccgtcgtgta gataactacg atacgggagg   1380
gcttaccatc tggccccagt gctgcaatga taccgcgaga cccacgctca ccggctccag   1440
atttatcagc aataaaccag ccagccggaa gggccgagcg cagaagtggt cctgcaactt   1500
tatccgcctc catccagtct attaattgtt gccgggaagc tagagtaagt agttcgccag   1560
ttaatagttt cgcaacgtt gttgccattg ctacaggcat cgtggtgtca cgctcgtcgt   1620
ttggtatggc ttcattcagc tccggttccc aacgatcaag gcgagttaca tgatccccca   1680
tgttgtgcaa aaaagcggtt agctccttcg gtcctccgat cgttgtcaga agtaagttgg   1740
ccgcagtgtt atcactcatg gttatggcag cactgcataa ttctcttact gtcatgccat   1800
ccgtaagatg cttttctgtg actggtgagt actcaaccaa gtcattctga atagtgta   1860 tgcggcgacc gagttgctct tgcccggcgt caatacggga taataccgcg ccacatagca   1920
gaactttaaa agtgctcatc attggaaaac gttcttcggg gcgaaaactc tcaaggatct   1980
taccgctgtt gagatccagt tcgatgtaac ccactcgtgc acccaactga tcttcagcat   2040
cttttacttt caccagcgtt tctgggtgag caaaaacagg aaggcaaaat gccgcaaaaa   2100
agggaataag ggcgacacgg aaatgttgaa tactcatact cttcctttt caatattatt   2160 gaagcattta tcagggttat tgtctcatga gcggatacat atttgaatgt atttagaaaa   2220
ataaacaaat aggggttccg cgcacatttc cccgaaaagt gccacctgat gcggtgtgaa   2280
ataccgcaca gatgcgtaag gagaaaatac cgcatcagga aattgtaagc gttaatattt   2340
tgttaaaatt cgcgttaaat ttttgttaaa tcagctcatt ttttaaccaa taggccgaaa   2400
```

```
tcggcaaaat cccttataaa tcaaaagaat agaccgagat agggttgagt gttgttccag    2460
tttggaacaa gagtccacta ttaaagaacg tggactccaa cgtcaaaggg cgaaaaaccg    2520
tctatcaggg cgatggccca ctacgtgaac catcacccta atcaagtttt tgggggtcga    2580
ggtgccgtaa agcactaaat cggaaccctaaaggagccccc cgatttaga gcttgacggg    2640 gaaagccggc gaacgtggcg agaaaggaag ggaagaaagc gaaggagcg ggcgctaggg    2700 cgctggcaag tgtagcggtc acgctgcgcg taaccaccac acccgccgcg cttaatgcgc    2760
cgctacaggg cgcgtccatt cgccattcag gctgcgcaac tgttgggaag ggcgatcggt    2820
gcgggcctct tcgctattac gccagctggc gaaaggggga tgtgctgcaa ggcgattaag    2880
ttgggtaacg ccagggtttt cccagtcacg acgttgtaaa acgacggcca gtgaattgta    2940
atacgactca ctatagggcg aattgggccc gacgtcgcat gctcccggcc gccatggcgg    3000
ccgcgggaat tcgattgcgg ccgctagata tgtagagcta ccccaggttt tctccctatt    3060
tttctttttt ccgcgggatg ggcgggttag ggagctgtgt gcgcatgttc gtgatgtggt    3120
agagagaaag cacactgctg tatggggagg gggaagggg aactggcgtt gtagcaactg     3180
caactggagg agtgtggtga tgggtggtac acatgtatca ggcgctgacg ccccttggcc    3240
tcatttcatt ttctctcatt tcttgttcca ctctagctgg tctgttgttc ccatctcgct    3300
atgtgcttct tttcccattt ttttttttctt ttgttgacca tcgttcaccg tgcgggtaca    3360
tatgactgtc tctctgtttt tttttttctc tcttttttttt ttcttctttt ttctatttct    3420 ctttcttttcc cctttgtttg tgtttgcttt gaccgctcat gtgtgtcgtg ctgtcatcgc    3480
atgcgccata actataccgt gaaagaaaaa aacagaatag aagaacctca agaagagatt    3540
caatcgaaca acaattactg aataacagtt gaagagaaat ggccggccat ggagaaaaaa    3600
atcactggat ataccaccgt tgatatatcc caatggcatc gtaaagaaca ttttgaggca    3660
tttcagtcag ttgctcaatg tacctataac cagaccgttc agctggatat tacggccttt    3720
ttaaagaccg taaagaaaaa taagcacaag ttttatccgg cctttattca cattcttgcc    3780
cgcctgatga atgctcatcc ggaattccgt atggcaatga agacggtga gctggtgata    3840 tgggatagtg ttcacccttg ttacaccgtt tccatgagc aaactgaaac gttttcatcg    3900
ctctggagtg aataccacga cgatttccgg cagtttctac acatatattc gcaagatgtg    3960
gcgtgttacg gtgaaaacct ggcctatttc cctaaaggt ttattgagaa tatgttttc     4020 gtctcagcca atccctgggt gagtttcacc agttttgatt taaacgtggc caatatggac    4080
aacttcttcg ccccgtttt caccatgggc aaatattata cgcaaggcga caaggtgctg    4140
atgccgctgg cgattcaggt tcatcatgcc gtctgtgatg cttccatgt cggcagaatg    4200 cttaatgaat tacaacagta ctgcgatgag tggcagggcg ggcgtaagg cgcgcctaaa    4260 tgggatacat gggggtgcag tagcaacgac agcagcagtg ttgtggtctg ggagggcat    4320 gtgaggacag caagaaatag gacatccgac cccgattctc ttcgcctgtt tgtgcttttt    4380 gttttttcctt cgttttatga caaatctttt ttttccgggg gttagggact gagagaatga    4440
ttttgtgctc aggcgtccgt ttattataga gctcaggagg agaacagcat tgttaggag    4500 aacggcagca aggtcatagc cggacgttag ccgcggaggg gattgagaga gagagaaga    4560 agaagagaga aagaaagtag gataggatag agaggaggtg tttctcttct ttactgtctg    4620
actcgttatc tctctgttct tttttctcct tctttcactg atgtaatcga ttttctcttg    4680
taccccttct tcttttcatc tgttgtgtat gtatgtatgc atgtttgtgc gtgtgttttt    4740
gttctgtgct gtgccattgt taccgcccta caccttttgtt gctccttttt tgttcctctt    4800
```

```
tttttttttt ttcccttacc gcctgtgttc ttctccgtgc acatccactt ctttggtcgc    4860
ggttagtttt agctaagctt tcgagctctt cttcaaacac tttacaagtt ttttcttttt    4920
ttcaacggta ccatgccttt gtctcaagaa gaatccaccc tcattgaaag agcaacggct    4980
acaatcaaca gcatccccat ctctgaagac tacagcgtcg ccagcgcagc tctctctagc    5040
gacggccgca tcttcactgg tgtcaatgta tatcatttta ctgggggacc ttgtgcagaa    5100
ctcgtggtgc tgggcactgc tgctgctgcg gcagctggca acctgacttg tatcgtcgcg    5160
atcggaaatg agaacagggg catcttgagc ccctgcggac ggtgtcgaca ggtgcttctc    5220
gatctgcatc ctgggatcaa agcgatagtg aaggacagtg atggacagcc gacggcagtt    5280
gggattcgtg aattgctgcc ctctggttat gtgtgggagg ctaaagatc  ttaaatggga    5340 tacatggggg tgcagtagca acgacagcag cagtgttgtg gtctggggag ggcatgtgag    5400
gacagcaaga aataggacat ccgaccccga ttctcttcgc ctgtttgtgc ttttttgtttt   5460 tccttcgttt tatgacaaat ctttttttt  ccggggttag ggactgagag aatgattttg    5520
tgctcaggcg tccgtttatt atagagctca ggaggagaac agcatttgtt aggagaacgg    5580
cagcaaggtc atagccggac gttagccgcg gaggggattg agagagagag aaagaagaag    5640
agagaaagaa agtaggatag gatagagagg aggtgtttct cttctttact gtctgactcg    5700
ttatctctct gttctttttt ctccttcttt cactgatgta atcgattttc tcttgtaccc    5760
cttcttcttt tcatctgttg tgtatgtatg tatgcatgtt tgtgcgtgtg ttttgttct    5820 gtgctgtgcc attgttaccg ccctacacct ttgttgctcc tttttgttc  ctcttttttt    5880 ttttttcc  ttaccgcctg tgttcttctc cgtgcacatc cacttctttg gtcgcggtta    5940
gttttagcta agctttcgag ctcttcttca aacactttac aagtttttc  tttttttcaa    6000 cttaattaa                                                            6009
```

<210> SEQ ID NO 2
<211> LENGTH: 11747
<212> TYPE: DNA
<213> ORGANISM: Artificial Sequence
<220> FEATURE:
<223> OTHER INFORMATION: Transfervector p53BBTandemXma
<220> FEATURE:
<221> NAME/KEY: misc_feature
<222> LOCATION: (1)..(2937)
<223> OTHER INFORMATION: pGEMTeasy plasmid backbone
<220> FEATURE:
<221> NAME/KEY: misc_feature
<222> LOCATION: (2943)..(3801)
<223> OTHER INFORMATION: 5' end of 18S SSU rRNA gene
<220> FEATURE:
<221> NAME/KEY: misc_feature
<222> LOCATION: (3808)..(3940)
<223> OTHER INFORMATION: Actin IR splice leader acceptor sequence
<220> FEATURE:
<221> NAME/KEY: misc_feature
<222> LOCATION: (3949)..(5193)
<223> OTHER INFORMATION: BiP N-terminal fragment
<220> FEATURE:
<221> NAME/KEY: misc_feature
<222> LOCATION: (5200)..(6222)
<223> OTHER INFORMATION: Bd37 gene
<220> FEATURE:
<221> NAME/KEY: misc_feature
<222> LOCATION: (6231)..(6900)
<223> OTHER INFORMATION: beta-alpha Tubulin IR
<220> FEATURE:
<221> NAME/KEY: misc_feature
<222> LOCATION: (6917)..(8161)
<223> OTHER INFORMATION: BiP N-terminal fragment
<220> FEATURE:

```
<221> NAME/KEY: misc_feature
<222> LOCATION: (8168)..(9190)
<223> OTHER INFORMATION: Bd37 gene
<220> FEATURE:
<221> NAME/KEY: misc_feature
<222> LOCATION: (9199)..(9868)
<223> OTHER INFORMATION: beta-alpha Tubulin IR
<220> FEATURE:
<221> NAME/KEY: misc_feature
<222> LOCATION: (9875)..(10267)
<223> OTHER INFORMATION: BSD gene
<220> FEATURE:
<221> NAME/KEY: misc_feature
<222> LOCATION: (10274)..(10943)
<223> OTHER INFORMATION: beta-alpha Tubulin IR
<220> FEATURE:
<221> NAME/KEY: misc_feature
<222> LOCATION: (10952)..(11736)
<223> OTHER INFORMATION: 3' end of 18S SSU rRNA gene

<400> SEQUENCE: 2
```

| | | | | | |
|---|---|---|---|---|---|
| ggtcgaccat | atgggagagc | tcccaacgcg | ttggatgcat | agcttgagta | ttctatagtg | 60 |
| tcacctaaat | agcttggcgt | aatcatggtc | atagctgttt | cctgtgtgaa | attgttatcc | 120 |
| gctcacaatt | ccacacaaca | tacgagccgg | aagcataaag | tgtaaagcct | ggggtgccta | 180 |
| atgagtgagc | taactcacat | taattgcgtt | gcgctcactg | cccgctttcc | agtcgggaaa | 240 |
| cctgtcgtgc | cagctgcatt | aatgaatcgg | ccaacgcgcg | gggagaggcg | gtttgcgtat | 300 |
| tgggcgctct | tccgcttcct | cgctcactga | ctcgctgcgc | tcggtcgttc | ggctgcggcg | 360 |
| agcggtatca | gctcactcaa | aggcggtaat | acggttatcc | acagaatcag | gggataacgc | 420 |
| aggaaagaac | atgtgagcaa | aaggccagca | aaaggccagg | aaccgtaaaa | aggccgcgtt | 480 |
| gctggcgttt | ttccataggc | tccgcccccc | tgacgagcat | cacaaaaatc | gacgctcaag | 540 |
| tcagaggtgg | cgaaacccga | caggactata | aagataccag | gcgtttcccc | ctggaagctc | 600 |
| cctcgtgcgc | tctcctgttc | cgaccctgcc | gcttaccgga | tacctgtccg | cctttctccc | 660 |
| ttcgggaagc | gtggcgcttt | ctcatagctc | acgctgtagg | tatctcagtt | cggtgtaggt | 720 |
| cgttcgctcc | aagctgggct | gtgtgcacga | accccccgtt | cagcccgacc | gctgcgcctt | 780 |
| atccggtaac | tatcgtcttg | agtccaaccc | ggtaagacac | gacttatcgc | cactggcagc | 840 |
| agccactggt | aacaggatta | gcagagcgag | gtatgtaggc | ggtgctacag | agttcttgaa | 900 |
| gtggtggcct | aactacggct | acactagaag | aacagtattt | ggtatctgcg | ctctgctgaa | 960 |
| gccagttacc | ttcggaaaaa | gagttggtag | ctcttgatcc | ggcaaacaaa | ccaccgctgg | 1020 |
| tagcggtggt | ttttttgttt | gcaagcagca | gattacgcgc | agaaaaaaag | gatctcaaga | 1080 |
| agatcctttg | atcttttcta | cggggtctga | cgctcagtgg | aacgaaaact | cacgttaagg | 1140 |
| gattttggtc | atgagattat | caaaaaggat | cttcacctag | atccttttaa | attaaaaatg | 1200 |
| aagttttaaa | tcaatctaaa | gtatatatga | gtaaacttgg | tctgacagtt | accaatgctt | 1260 |
| aatcagtgag | gcacctatct | cagcgatctg | tctatttcgt | tcatccatag | ttgcctgact | 1320 |
| ccccgtcgtg | tagataacta | cgatacggga | gggcttacca | tctggcccca | gtgctgcaat | 1380 |
| gataccgcga | gacccacgct | caccggctcc | agatttatca | gcaataaacc | agccagccgg | 1440 |
| aagggccgag | cgcagaagtg | gtcctgcaac | tttatccgcc | tccatccagt | ctattaattg | 1500 |
| ttgccgggaa | gctagagtaa | gtagttcgcc | agttaatagt | ttgcgcaacg | ttgttgccat | 1560 |
| tgctacaggc | atcgtggtgt | cacgctcgtc | gtttggtatg | gcttcattca | gctccggttc | 1620 |
| ccaacgatca | aggcgagtta | catgatcccc | catgttgtgc | aaaaaagcgg | ttagctcctt | 1680 |
| cggtcctccg | atcgttgtca | gaagtaagtt | ggccgcagtg | ttatcactca | tggttatggc | 1740 |

```
agcactgcat aattctctta ctgtcatgcc atccgtaaga tgcttttctg tgactggtga    1800
gtactcaacc aagtcattct gagaatagtg tatgcggcga ccgagttgct cttgcccggc    1860
gtcaatacgg gataataccg cgccacatag cagaacttta aaagtgctca tcattggaaa    1920
acgttcttcg gggcgaaaac tctcaaggat cttaccgctg ttgagatcca gttcgatgta    1980
acccactcgt gcacccaact gatcttcagc atcttttact ttcaccagcg tttctgggtg    2040
agcaaaaaca ggaaggcaaa atgccgcaaa aaagggaata agggcgacac ggaaatgttg    2100
aatactcata ctcttccttt ttcaatatta ttgaagcatt tatcagggtt attgtctcat    2160
gagcggatac atatttgaat gtatttagaa aaataaacaa ataggggttc cgcgcacatt    2220
tccccgaaaa gtgccacctg atgcggtgtg aaataccgca cagatgcgta aggagaaaat    2280
accgcatcag gaaattgtaa gcgttaatat tttgttaaaa ttcgcgttaa attttgttta    2340
aatcagctca tttttaacc aataggccga atcggcaaa atcccttata atcaaaaga     2400
atagaccgag ataggttga gtgttgttcc agtttggaac aagagtccac tattaaagaa    2460
cgtggactcc aacgtcaaag ggcgaaaaac cgtctatcag ggcgatggcc cactacgtga    2520
accatcaccc taatcaagtt ttttggggtc gaggtgccgt aaagcactaa atcggaaccc    2580
taaagggagc ccccgattta gagcttgacg gggaaagccg gcgaacgtgg cgagaaagga    2640
agggaagaaa gcgaaaggag cgggcgctag ggcgctggca agtgtagcgg tcacgctgcg    2700
cgtaaccacc acacccgccg cgcttaatgc gccgctacag ggcgcgtcca ttcgccattc    2760
aggctgcgca actgttggga agggcgatcg gtgcgggcct cttcgctatt acgccagctg    2820
gcgaaagggg gatgtgctgc aaggcgatta agttgggtaa cgccagggtt ttcccagtca    2880
cgacgttgta aaacgacggc cagtgaattg taatacgact cactataggg cgaattgggc    2940
ccgcatggct cattacatca gacgtaatct gccgcaaaaa tcttgcggtt ccgcaacat     3000
tggataactt ggcgaaacgc caagctaata catgaaccaa agggacgttc tctgttccgg    3060
cggtggggca actcactgtc atgggcgtc cagcgaatga atgaaattaa aaccaatgcc     3120
ttcaccggca gtaacaccca gaagtgttga ctcaattcat tccgtgcgaa agctggattt    3180
cttatccggc gtcttttgac gaacaactgc cctatcagcc agtgatggcc gtgtagtgga    3240
ctgccatggc gttgacggga gcggggatt agggttcgat tccggagagg gagcctgaga    3300
aatagctacc acttctacgg agggcagcag gcgcgcaaat tgcccaatgt caaaaaaaaa    3360
cgatgaggca gcgaaaagaa atagagccga cagtgcctag tgcattgtcg ttttcaatgg    3420
gggatattta aacccatcca aaatcgagta acaattggag gacaagtctg gtgccagcac    3480
ccgcggtaat tccagctcca aaagcgtata ttaatgctgt tgctgttaaa gggttcgtag    3540
ttgaattgtg ggccttgag gcgcaatggt ttgtcccgtc cacctcggat tggtgaccca     3600
tgcccttgag gtccgtgaac aatcagaaac aaaaaacacg ggagcggttc cttcctgatt    3660
ttcgcatgtc atgcatgcca gggggcgtcc gtgattttta ctgtgactaa aaagtgtga    3720
ccaaagcagt cattcgactt gaattagaaa gcatgggata acaaaggagc agcctatggg    3780
ctaccgtttc ggcttttgtt gcctagggtc gttgttatcg ttgtacgttg caatgtacga    3840
agcttgtctc gaaaaattca tatttttt cttcttttcc actctttgt ttttattatt       3900
tgatttatgt agttcgtttt gcatatcgag ttactatttc ggccggccat gtcgaggatg    3960
tggctgacca ctgcagcggt gttcctgact gtgacggttg cagccgtctc agcagcaccc    4020
gaaagtggcg gcaaggtgga agcaccatgc gtgggcatcg acctcggcac aacatactcc    4080
```

```
gttgtgggtg tgtggcagaa gggtgatgtg catatcatcc cgaacgagat gggtaaccgc    4140
atcacacctt ccgtcgtcgc ctttaccgac acagagcggc tgatcggtga cggtgcgagg    4200
aatcagcttc cacagaatcc gcataataca atctacacca tcaagaggct gattggccgc    4260
aagtacacgg atgcggcagt gcaggctgac aagaaactgc tgtcgtatga ggtcattgcg    4320
gaccgcgacg ggaagccgaa ggtacaagtg atggtgggtg ggaaaaagaa acagttcaca    4380
ccagaagaga tcagtgccat ggtgctgcag aagatgaagg aaattgcaga aacgtacctt    4440
ggcgagaaag tgaaaaacgc tgttgtaacg gtacctgcgt acttcaatga cgcacaacgg    4500
cagtcgacaa aggatgctgg gaccatcgcc ggtttgaacg tagtgcgcat catcaatgag    4560
cccaccgcag ccgccatcgc atatgggcta acaaagccg gtgagaagaa tatcctggtg    4620
ttcgatcttg gtggtggtac ctttgatgtg tcactgctga caatcgatga gggcttcttc    4680
gaagttgtgg cgacaaacgg tgatacgcac cttggtggtg aggactttga taacaacatg    4740
atgcgacact ttgtggacat gctgaagaag aaaaagaatg ttgacatcag taaggaccaa    4800
aaggcactgg cacgtcttcg caaggcatgt gaggctgcga agcgacagct gtcgtctcat    4860
cccgaggcgc gtgtggaggt ggacagcctt acggagggct tcgatttcag cgagaaaatc    4920
acacgtgcga agtttgagga gctgaacatg gacctcttca aggggacact cgtgcccgtg    4980
caacgtgtgc tggaggatgc gaagctgaag aagagtgaca tccacgagat tgtgctcgtt    5040
ggtggatcca cacgtgtgcc gaaggtacaa caactgatca gtgacttctt cggtgggaag    5100
gaactgaacc gtggtattaa ccccgatgaa gccgtagcat atggtgccgc tgtgcaagct    5160
gcggtgctaa ccggtgaaag cgaggttggc gggcctagga aaaccagtaa gattctcaac    5220
actgctgcta tctgcctcct ggctatgggt ttcaatggca ataatgtgag ctgcaccaat    5280
ctcaatggct cacaggagcc agcagcggct aaccctgttg tttcaactcc tgggaatgat    5340
gcgcagcagg ctggtacgca gcaaggtggt gcgaactcaa agtccgttcc agagcagcag    5400
ccacagcagg ctgccggcga aaccactgct acggtcgtgg taaagactct agatgtgctc    5460
cgtggggaac tcaggggggca gcgtgaggct ttcctttcag agataattaa atcggatggt    5520
ccattcacta ttttgcagtt ggttggctac cttcgtgttg tcgacacaga tcttctcctg    5580
aaagttgatt ccacgaaggt tgatgaagcc ggcaagaagg tcaaggccta ccttgaaaaa    5640
attggaataa ggggtgacag tgttgaagca gcgcttgaca atcttatgat aaaggtttat    5700
gaaatcacca aaggtactgt ggaaagttca gcacaaggta ctgacagtga ggagctgaag    5760
actttgttat aaagttcag cgaagatctc aaggctgagc aagaacttca tagtgaagcc    5820
aagggcggtg aggccttgct ttctagcatg aagacgcagc atgatgaact acttaagaag    5880
tttgctgccc ttaccectac tttcttaacc tcagaggata tatctggcta ccttaccgtg    5940
ccggaatacg gtgcccctat gaatgctgcg aagtggaaaa aggtggaagg aatgatccat    6000
ggaaagctcg agtcttccga agtaccagct aatctcaaag ctctggttgc agagttaatt    6060
gagttgcgtg aacagatgat ggatttgcta tacggcccta ttggtcatca cgattgtgct    6120
gcaggatcag gtcagggatc tagtcctaag aagccatcct tcgctgctgt accttcttct    6180
ttgtctgcca ttgtcttcgg tatcattgta tcaatgttct aaggcgcgcc taaatgggat    6240
acatggggt gcagtagcaa cgacagcagc agtgttgtgg tctggggagg gcatgtgagg    6300
acagcaagaa ataggacatc cgaccccgat tctcttcgcc tgtttgtgct ttttgttttt    6360
ccttcgtttt atgacaaatc ttttttttc cggggtagg gactgagaga atgattttgt    6420
gctcaggcgt ccgtttatta tagagctcag gaggagaaca gcatttgtta ggagaacggc    6480
```

```
agcaaggtca tagccggacg ttagccgcgg aggggattga gagagagaga aagaagaaga    6540
gagaaagaaa gtaggatagg atagagagga ggtgtttctc ttctttactg tctgactcgt    6600
tatctctctg ttcttttttc tccttctttc actgatgtaa tcgattttct cttgtacccc    6660
ttcttctttt catctgttgt gtatgtatgt atgcatgttt gtgcgtgtgt ttttgttctg    6720
tgctgtgcca ttgttaccgc cctacacctt tgttgctcct ttttgttcc tcttttttt    6780 tttttccct taccgcctgt gttcttctcc gtgcacatcc acttctttgg tcgcggttag    6840
ttttagctaa gctttcgagc tcttcttcaa acactttaca agttttttct ttttttcaac    6900
ggtaccaatc actagtatgt cgaggatgtg gctgaccact gcagcggtgt tcctgactgt    6960
gacggttgca gccgtctcag cagcacccga aagtggcggc aaggtggaag caccatgcgt    7020
gggcatcgac ctcggcacaa catactccgt tgtgggtgtg tggcagaagg gtgatgtgca    7080
tatcatcccg aacgagatgg gtaaccgcat cacaccttcc gtcgtcgcct ttaccgacac    7140
agagcggctg atcggtgacg gtgcgaggaa tcagcttcca cagaatccgc ataatacaat    7200
ctacaccatc aagaggctga ttggccgcaa gtacacggat gcggcagtgc aggctgacaa    7260
gaaactgctg tcgtatgagg tcattgcgga ccgcgacggg aagccgaagg tacaagtgat    7320
ggtgggtggg aaaaagaaac agttcacacc agaagagatc agtgccatgg tgctgcagaa    7380
gatgaaggaa attgcagaaa cgtaccttgg cgagaaagtg aaaaacgctg ttgtaacggt    7440
acctgcgtac ttcaatgacg cacaacggca gtcgacaaag gatgctggga ccatcgccgg    7500
tttgaacgta gtgcgcatca tcaatgagcc caccgcagcc gccatcgcat atgggctaaa    7560
caaagccggt gagaagaata tcctggtgtt cgatcttggt ggtggtacct ttgatgtgtc    7620
actgctgaca atcgatgagg gcttcttcga agttgtggcg acaaacggtg atacgcacct    7680
tggtggtgag gactttgata caacatgat gcgacacttt gtggacatgc tgaagaagaa    7740
aaagaatgtt gacatcagta aggaccaaaa ggcactggca cgtcttcgca aggcatgtga    7800
ggctgcgaag cgacagctgt cgtctcatcc cgaggcgcgt gtggaggtgg acagccttac    7860
ggagggcttc gatttcagcg agaaaatcac acgtgcgaag tttgaggagc tgaacatgga    7920
cctcttcaag gggacactcg tgcccgtgca acgtgtgctg gaggatgcga agctgaagaa    7980
gagtgacatc cacgagattg tgctcgttgg tggatccaca cgtgtgccga aggtacaaca    8040
actgatcagt gacttcttcg gtgggaagga actgaaccgt ggtattaacc ccgatgaagc    8100
cgtagcatat ggtgccgctg tgcaagctgc ggtgctaacc ggtgaaagcg aggttggcgg    8160
gcctaggaaa accagtaaga ttctcaacac tgctgctatc tgcctcctgg ctatgggttt    8220
caatggcaat aatgtgagct gcaccaatct caatggctca caggagccag cagcggctaa    8280
ccctgttgtt tcaactcctg ggaatgatgc gcagcaggct ggtacgcagc aaggtggtgc    8340
gaactcaaag tccgttccag agcagcagcc acagcaggct gccggcgaaa ccactgctac    8400
ggtcgtggta aagactctag atgtgctccg tggggaactc aggggcagc gtgaggcttt    8460 cctttcagag ataattaaat cggatggtcc attcactatt ttgcagttgg ttggctacct    8520
tcgtgttgtc gacacagatc ttctcctgaa agttgattcc acgaaggttg atgaagccgg    8580
caagaaggtc aaggcctacc ttgaaaaaat tggaataagg ggtgacagtg ttgaagcagc    8640
gcttgacaat cttatgataa aggtttatga aatcaccaaa ggtactgtgg aaagttcagc    8700
acaaggtact gacagtgagg agctgaagac tttgttatta aagttcagcg aagatctcaa    8760
ggctgagcaa gaacttcata gtgaagccaa gggcggtgag gccttgcttt ctagcatgaa    8820
```

```
gacgcagcat gatgaactac ttaagaagtt tgctgcccct acccctactt tcttaacctc    8880
agaggatata tctggctacc ttaccgtgcc ggaatacggt gccccctatga atgctgcgaa   8940 gtggaaaaag gtggaaggaa tgatccatgg aaagctcgag tcttccgaag taccagctaa   9000
tctcaaagct ctggttgcag agttaattga gttgcgtgaa cagatgatgg atttgctata   9060
cggccctatt ggtcatcacg attgtgctgc aggatcaggt cagggatcta gtcctaagaa   9120
gccatccttc gctgctgtac cttcttcttt gtctgccatt gtcttcggta tcattgtatc   9180
aatgttctaa ggcgcgccta aatgggatac atggggggtgc agtagcaacg acagcagcag  9240
tgttgtggtc tggggagggc atgtgaggac agcaagaaat aggacatccg accccgattc   9300
tcttcgcctg tttgtgcttt tgtttttcc ttcgttttat gacaaatctt ttttttttccg   9360 gggttaggga ctgagagaat gatttttgtgc tcaggcgtcc gtttattata gagctcagga   9420
ggagaacagc atttgttagg agaacggcag caaggtcata gccggacgtt agccgcggag   9480
gggattgaga gagagagaaa gaagaagaga gaaagaaagt aggataggat agagaggagg   9540
tgtttctctt ctttactgtc tgactcgtta tctctctgtt ctttttttctc cttctttcac   9600 tgatgtaatc gattttctct tgtaccccctt cttcttttca tctgttgtgt atgtatgtat   9660
gcatgtttgt gcgtgtgttt tgttctgtg ctgtgccatt gttaccgccc tacaccctttg    9720 ttgctccttt tttgttcctc ttttttttttt ttttcccctta ccgcctgtgt tcttctccgt   9780
gcacatccac ttctttggtc gcggttagtt ttagctaagc tttcgagctc ttcttcaaac    9840
actttacaag tttttttcttt ttttcaacgg taccatgcct ttgtctcaag aagaatccac   9900
cctcattgaa agagcaacgg ctacaatcaa cagcatcccc atctctgaag actacagcgt   9960
cgccagcgca gctctctcta gcgacggccg catcttcact ggtgtcaatg tatatcattt    10020
tactggggga ccttgtgcag aactcgtggt gctgggcact gctgctgctg cggcagctgg   10080
caacctgact tgtatcgtcg cgatcggaaa tgagaacagg ggcatcttga gccctgcgg    10140 acggtgtcga caggtgcttc tcgatctgca tcctgggatc aaagcgatag tgaaggacag   10200
tgatggacag ccgacggcag ttgggattcg tgaattgctg ccctctggtt atgtgtggga   10260
gggctaaaga tcttaaatgg gatacatggg ggtgcagtag caacgacagc agcagtgttg   10320
tggtctgggg agggcatgtg aggacagcaa gaaataggac atccgacccc gattctcttc   10380
gcctgtttgt gctttttgtt ttccttcgt tttatgacaa atctttttttt ttccgggggtt   10440 agggactgag agaatgattt tgtgctcagg cgtccgttta ttatagagct caggaggaga   10500
acagcatttg ttaggagaac ggcagcaagg tcatagccgg acgttagccg cggaggggat   10560
tgagagagag agaaagaaga agagagaaag aaagtaggat aggatagaga ggaggtgttt   10620
ctcttcttta ctgtctgact cgttatctct ctgttctttt ttctccttct ttcactgatg   10680
taatcgattt tctcttgtac cccttcttct tttcatctgt tgtgtatgta tgtatgcatg   10740
tttgtgcgtg tgttttgtt ctgtgctgtg ccattgttac cgccctacac ctttgttgct    10800
ccttttttgt tcctcttttt ttttttttc ccttaccgcc tgtgttcttc tccgtgcaca    10860
tccacttctt tggtcgcggt tagttttagc taagctttcg agctcttctt caaacacttt   10920
acaagttttt tcttttttc aacttaatta atcctcagc acgtttctta cttctttacg     10980
cgaaagcttt gaggttacag tctcaggggg gagtacgttc gcaagagtga aacttaaaga   11040
aattgacgga atggcaccac aagacgtgga gcgtgcggtt taattgact caacacgggg    11100 aactttacca gatccggaca gggtgaggat tgacagattg agtgttcttt ctcgatcccc   11160
tgaatggtgg tgcatggccg cttttggtcg gtggagtgat ttgtttggtt gattccgtca   11220
```

```
acggacgaga tccaagctgc ccagtaggat tcagaattgc ccataggata gcaatcccct    11280
ccgcgggttt tcccaagga ggggcgatat tcgtttgtat ccttctctgc gggattcctt    11340
gttttgcgca aggtgagatt ttgggcaaca gcaggtctgt gatgctcctc aatgttctgg    11400
gcgacacgcg cactacaatg tcagtgagaa caagaaaaac gacttttgtc ggacctactt    11460
gatcaaaaga gtgggaaaac cccggaatca catagaccca cttgggaccg agtattgcaa    11520
ttatcggtcg cgcaacgagg aatgtctcgt aggcgcagct catcaaactg tgccgattac    11580
gtccctgcca tttgtacaca ccgcccgtcg ttgtttccga tgatggtgca atacaggtga    11640
acggacagtc gaacgtttcg tttgaccgaa agttcaccga tatttcttca atagaggaag    11700
caaaagtcgt aacaaggtag ctgtaggtga acctgccccg ggctgca                 11747
```

```
<210> SEQ ID NO 3
<211> LENGTH: 32
<212> TYPE: DNA
<213> ORGANISM: Artificial Sequence
<220> FEATURE:
<223> OTHER INFORMATION: degenerated cloning primer
<220> FEATURE:
<221> NAME/KEY: misc_feature
<222> LOCATION: (15)..(15)
<223> OTHER INFORMATION: n=inosine
<220> FEATURE:
<221> NAME/KEY: misc_feature
<222> LOCATION: (27)..(27)
<223> OTHER INFORMATION: n=inosine
<220> FEATURE:
<221> NAME/KEY: misc_feature
<222> LOCATION: (30)..(30)
<223> OTHER INFORMATION: n=inosine

<400> SEQUENCE: 3
cccaaraart traangcrtc rtcytcntcn cc                                  32

<210> SEQ ID NO 4
<211> LENGTH: 29
<212> TYPE: DNA
<213> ORGANISM: Artificial Sequence
<220> FEATURE:
<223> OTHER INFORMATION: degenerated cloning primer
<220> FEATURE:
<221> NAME/KEY: misc_feature
<222> LOCATION: (3)..(3)
<223> OTHER INFORMATION: n=inosine
<220> FEATURE:
<221> NAME/KEY: misc_feature
<222> LOCATION: (24)..(24)
<223> OTHER INFORMATION: n=inosine

<400> SEQUENCE: 4
ggnatggayg aratggartt yacngargc                                      29

<210> SEQ ID NO 5
<211> LENGTH: 35
<212> TYPE: DNA
<213> ORGANISM: Artificial Sequence
<220> FEATURE:
<223> OTHER INFORMATION: degenerated cloning primer
<220> FEATURE:
<221> NAME/KEY: misc_feature
<222> LOCATION: (6)..(6)
<223> OTHER INFORMATION: n=inosine
<220> FEATURE:
<221> NAME/KEY: misc_feature
<222> LOCATION: (9)..(9)
<223> OTHER INFORMATION: n=inosine
<220> FEATURE:
```

```
<221> NAME/KEY: misc_feature
<222> LOCATION: (12)..(12)
<223> OTHER INFORMATION: n=inosine
<220> FEATURE:
<221> NAME/KEY: misc_feature
<222> LOCATION: (18)..(18)
<223> OTHER INFORMATION: n=inosine
<220> FEATURE:
<221> NAME/KEY: misc_feature
<222> LOCATION: (21)..(21)
<223> OTHER INFORMATION: n=inosine
<220> FEATURE:
<221> NAME/KEY: misc_feature
<222> LOCATION: (24)..(24)
<223> OTHER INFORMATION: n=inosine
<220> FEATURE:
<221> NAME/KEY: misc_feature
<222> LOCATION: (33)..(33)
<223> OTHER INFORMATION: n=inosine

<400> SEQUENCE: 5
cccgcnaaag tncarmgngc ngtntgyatg atngc                              35

<210> SEQ ID NO 6
<211> LENGTH: 30
<212> TYPE: DNA
<213> ORGANISM: Artificial Sequence
<220> FEATURE:
<223> OTHER INFORMATION: degenerated cloning primer
<220> FEATURE:
<221> NAME/KEY: misc_feature
<222> LOCATION: (4)..(4)
<223> OTHER INFORMATION: n=inosine
<220> FEATURE:
<221> NAME/KEY: misc_feature
<222> LOCATION: (7)..(7)
<223> OTHER INFORMATION: n=inosine
<220> FEATURE:
<221> NAME/KEY: misc_feature
<222> LOCATION: (16)..(16)
<223> OTHER INFORMATION: n=inosine
<220> FEATURE:
<221> NAME/KEY: misc_feature
<222> LOCATION: (19)..(19)
<223> OTHER INFORMATION: n=inosine
<220> FEATURE:
<221> NAME/KEY: misc_feature
<222> LOCATION: (21)..(21)
<223> OTHER INFORMATION: n=inosine
<220> FEATURE:
<221> NAME/KEY: misc_feature
<222> LOCATION: (22)..(22)
<223> OTHER INFORMATION: n=inosine
<220> FEATURE:
<221> NAME/KEY: misc_feature
<222> LOCATION: (25)..(25)
<223> OTHER INFORMATION: n=inosine
<220> FEATURE:
<221> NAME/KEY: misc_feature
<222> LOCATION: (28)..(28)
<223> OTHER INFORMATION: n=inosine

<400> SEQUENCE: 6
cccnaangtc atcatnatnc nntcnggnta                                    30

<210> SEQ ID NO 7
<211> LENGTH: 33
<212> TYPE: DNA
<213> ORGANISM: Artificial Sequence
<220> FEATURE:
<223> OTHER INFORMATION: degenerated cloning primer
<220> FEATURE:
<221> NAME/KEY: misc_feature
<222> LOCATION: (18)..(18)
<223> OTHER INFORMATION: n=inosine
```

```
<220> FEATURE:
<221> NAME/KEY: misc_feature
<222> LOCATION: (24)..(24)
<223> OTHER INFORMATION: n=inosine
<220> FEATURE:
<221> NAME/KEY: misc_feature
<222> LOCATION: (27)..(27)
<223> OTHER INFORMATION: n=inosine
<220> FEATURE:
<221> NAME/KEY: misc_feature
<222> LOCATION: (30)..(30)
<223> OTHER INFORMATION: n=inosine

<400> SEQUENCE: 7
gggaarcarg argargtnaa ratngcngcn gar                                   33

<210> SEQ ID NO 8
<211> LENGTH: 33
<212> TYPE: DNA
<213> ORGANISM: Artificial Sequence
<220> FEATURE:
<223> OTHER INFORMATION: degenerated cloning primer
<220> FEATURE:
<221> NAME/KEY: misc_feature
<222> LOCATION: (10)..(10)
<223> OTHER INFORMATION: n=inosine
<220> FEATURE:
<221> NAME/KEY: misc_feature
<222> LOCATION: (22)..(22)
<223> OTHER INFORMATION: n=inosine
<220> FEATURE:
<221> NAME/KEY: misc_feature
<222> LOCATION: (25)..(25)
<223> OTHER INFORMATION: n=inosine
<220> FEATURE:
<221> NAME/KEY: misc_feature
<222> LOCATION: (28)..(28)
<223> OTHER INFORMATION: n=inosine

<400> SEQUENCE: 8
gggrttrtgn atyttytgyt tnckngcngc ytc                                   33

<210> SEQ ID NO 9
<211> LENGTH: 21
<212> TYPE: DNA
<213> ORGANISM: Artificial Sequence
<220> FEATURE:
<223> OTHER INFORMATION: cloning primer

<400> SEQUENCE: 9
ggagtactag atatgtagag c                                                21

<210> SEQ ID NO 10
<211> LENGTH: 22
<212> TYPE: DNA
<213> ORGANISM: Artificial Sequence
<220> FEATURE:
<223> OTHER INFORMATION: cloning primer

<400> SEQUENCE: 10
ccctgaacac acacaatctc gc                                               22

<210> SEQ ID NO 11
<211> LENGTH: 670
<212> TYPE: DNA
<213> ORGANISM: Trypanosoma theileri

<400> SEQUENCE: 11
taaatgggat acatgggggt gcagtagcaa cgacagcagc agtgttgtgg tctggggagg      60
```

```
gcatgtgagg acagcaagaa ataggacatc cgaccccgat tctcttcgcc tgtttgtgct      120
ttttgttttt ccttcgtttt atgacaaatc ttttttttc cggggttagg gactgagaga      180
atgattttgt gctcaggcgt ccgtttatta tagagctcag gaggagaaca gcatttgtta      240
ggagaacggc agcaaggtca tagccggacg ttagccgcgg aggggattga gagagagaga    300
aagaagaaga gagaaagaaa gtaggatagg atagagagga ggtgtttctc ttctttactg    360
tctgactcgt tatctctctg ttcttttttc tccttctttc actgatgtaa tcgattttct    420
cttgtacccc ttcttctttt catctgttgt gtatgtatgt atgcatgttt gtgcgtgtgt    480
ttttgttctg tgctgtgcca ttgttaccgc cctacacctt tgttgctcct tttttgttcc    540 tcttttttt ttttttccct taccgcctgt gttcttctcc gtgcacatcc acttctttgg    600
tcgcggttag ttttagctaa gctttcgagc tcttcttcaa acactttaca agttttttct    660
ttttttcaac                                                             670

<210> SEQ ID NO 12
<211> LENGTH: 551
<212> TYPE: DNA
<213> ORGANISM: Trypanosoma theileri

<400> SEQUENCE: 12
atatgtagag ctaccccagg ttttctccct atttttctttt tttccgcggg atgggcgggt     60
tagggagctg tgtgcgcatg ttcgtgatgt ggtagagaga aagcacactg ctgtatgggg    120 aggggggaaag gggaactggc gttgtagcaa ctgcaactgg aggagtgtgg tgatgggtgg    180
tacacatgta tcaggcgctg acgcccttg gcctcatttc attttctctc atttcttgtt     240
ccactctagc tggtctgttg ttcccatctc gctatgtgct tcttttccca ttttttttttt  300 cttttgttga ccatcgttca ccgtgcgggt acatatgact gtctctctgt ttttttttt    360 ctctcttttt ttttttcttc tttttctatt tctctttctt tccctttgt ttgtgtttgc    420 tttgaccgct catgtgtgtc gtgctgtcat cgcatgcgcc ataactatac cgtgaaagaa    480
aaaaacagaa tagaagaacc tcaagaagag attcaatcga acaacaatta ctgaataaca    540
gttgaagaga a                                                          551

<210> SEQ ID NO 13
<211> LENGTH: 461
<212> TYPE: DNA
<213> ORGANISM: Trypanosoma theileri

<400> SEQUENCE: 13
tgtgtatgtg tgtatgcctg tgagcctctt tatcaccata accgctttca gtcccctctc     60
tttctcatcc tttttatgtt tcctattcca aatgatgta tcattgctat gtattacaga    120
cattgttggg ctacacgggc ttgctaaagt gtgttcctgt ccccccactg tgagtgaagc    180
gggtgggtgc aacacgccct gtgcagccct tgttttttct tttatgccc acaaagcgct    240 ggacttggaa atcagcaatg tatagcctga tgtcaccatg atgaccaagt gactgttttt    300
aaaggtgttc cttgcttta cacacctggc attccgttgt tggacttctt ttctcttcac    360
aaccttctct ttctctctct ctctctctct ctctctctct ttcctcaaaa taaagtgaag    420
tgaagcgcaa cagagcaatc accctcggtt aagaagaaac t                         461

<210> SEQ ID NO 14
<211> LENGTH: 21
<212> TYPE: DNA
<213> ORGANISM: Artificial Sequence
```

```
<220> FEATURE:
<223> OTHER INFORMATION: cloning primer

<400> SEQUENCE: 14
gggtatcgta cacaacaagt g                                            21

<210> SEQ ID NO 15
<211> LENGTH: 22
<212> TYPE: DNA
<213> ORGANISM: Artificial Sequence
<220> FEATURE:
<223> OTHER INFORMATION: cloning primer

<400> SEQUENCE: 15
ccctagcaga ttgctcctcc tc                                           22

<210> SEQ ID NO 16
<211> LENGTH: 31
<212> TYPE: DNA
<213> ORGANISM: Artificial Sequence
<220> FEATURE:
<223> OTHER INFORMATION: cloning primer

<400> SEQUENCE: 16
atagggcccg catggctcat tacatcagac g                                 31

<210> SEQ ID NO 17
<211> LENGTH: 32
<212> TYPE: DNA
<213> ORGANISM: Artificial Sequence
<220> FEATURE:
<223> OTHER INFORMATION: cloning primer

<400> SEQUENCE: 17
agacctaggc aacaaaagcc gaaacggtag cc                                32

<210> SEQ ID NO 18
<211> LENGTH: 33
<212> TYPE: DNA
<213> ORGANISM: Artificial Sequence
<220> FEATURE:
<223> OTHER INFORMATION: cloning primer

<400> SEQUENCE: 18
gggttaatta aatcctcagc acgtttctta ctt                               33

<210> SEQ ID NO 19
<211> LENGTH: 24
<212> TYPE: DNA
<213> ORGANISM: Artificial Sequence
<220> FEATURE:
<223> OTHER INFORMATION: cloning primer

<400> SEQUENCE: 19
atacccgggc tgcaggcagg ttca                                         24

<210> SEQ ID NO 20
<211> LENGTH: 392
<212> TYPE: DNA
<213> ORGANISM: Trypanosoma theileri

<400> SEQUENCE: 20
tggcttgtgt ttatctattt caatgctctc gagttgtgcc gtgttcaaag taaacattca   60
tagttcttag gtggcgcaaa gtcgcagtct cttctctttc caccgtagta gcggggaaag  120
```

```
ttttatggga aaagttttt tttttgcaat ttagatttt tcatgtatta gcctctttta      180
ttaaatatta ttgaggcact gactactagg gataatagaa cacgaactt ccactgcttt      240 ctgaacgtta tcgctgtcgt tgttatcgtt gtacgttgca atgtacgaag cttgtctcga     300
aaaattcata tattttttct tcttttccac tcttttgttt ttattatttg atttatgtag     360
ttcgttttgc atatcgagtt actatttcaa ca                                   392

<210> SEQ ID NO 21
<211> LENGTH: 133
<212> TYPE: DNA
<213> ORGANISM: Trypanosoma theileri

<400> SEQUENCE: 21
gtcgttgtta tcgttgtacg ttgcaatgta cgaagcttgt ctcgaaaaat tcatatattt      60
tttcttcttt tccactcttt tgtttttatt atttgattta tgtagttcgt tttgcatatc    120
gagttactat ttc                                                       133

<210> SEQ ID NO 22
<211> LENGTH: 859
<212> TYPE: DNA
<213> ORGANISM: Trypanosoma theileri

<400> SEQUENCE: 22
gcatggctca ttacatcaga cgtaatctgc cgcaaaaatc ttgcggtttc cgcaacattg      60
gataacttgg cgaaacgcca agctaataca tgaaccaaag ggacgttctc tgttccggcg    120
gtggggcaac tcactgtcat ggggcgtcca gcgaatgaat gaaattaaaa ccaatgcctt    180
caccggcagt aacacccaga agtgttgact caattcattc cgtgcgaaag ctggatttct    240
tatccggcgt cttttgacga acaactgccc tatcagccag tgatggccgt gtagtggact    300
gccatggcgt tgacgggagc gggggattag ggttcgattc cggagaggga gcctgagaaa    360
tagctaccac ttctacggag ggcagcaggc gcgcaaattg cccaatgtca aaaaaaaacg    420
atgaggcagc gaaagaaat agagccgaca gtgcctagtg cattgtcgtt tcaatggggg     480
gatatttaaa cccatccaaa atcgagtaac aattggagga caagtctggt gccagcaccc    540
gcggtaattc cagctccaaa agcgtatatt aatgctgttg ctgttaaagg gttcgtagtt    600
gaattgtggg cctttgaggc gcaatggttt gtcccgtcca cctcggattg gtgacccatg    660
cccttgaggt ccgtgaacaa tcagaaacaa aaaacacggg agcggttcct tcctgatttt    720
cgcatgtcat gcatgccagg gggcgtccgt gattttact gtgactaaaa aagtgtgacc      780
aaagcagtca ttcgacttga attagaaagc atgggataac aaaggagcag cctatgggct    840
accgtttcgg cttttgttg                                                 859

<210> SEQ ID NO 23
<211> LENGTH: 785
<212> TYPE: DNA
<213> ORGANISM: Trypanosoma theileri

<400> SEQUENCE: 23
atcctcagca cgtttcttac ttctttacgc gaaagctttg aggttacagt ctcaggggg      60 agtacgttcg caagagtgaa acttaaagaa attgacggaa tggcaccaca agacgtggag    120
cgtgcggttt aatttgactc aacacgggga actttaccag atccggacag ggtgaggatt    180
gacagattga gtgttctttc tcgatcccct gaatggtggt gcatggccgc ttttggtcgg    240
tggagtgatt tgtttggttg attccgtcaa cggacgagat ccaagctgcc cagtaggatt    300
```

-continued

```
cagaattgcc cataggatag caatcccctc cgcgggtttt tcccaaggag gggcgatatt    360
cgtttgtatc cttctctgcg ggattccttg ttttgcgcaa ggtgagattt tgggcaacag    420
caggtctgtg atgctcctca atgttctggg cgacacgcgc actacaatgt cagtgagaac    480
aagaaaaacg acttttgtcg gacctacttg atcaaaagag tgggaaaacc ccggaatcac    540
atagacccac ttgggaccga gtattgcaat tatcggtcgc gcaacgagga atgtctcgta    600
ggcgcagctc atcaaactgt gccgattacg tccctgccat tgtacacac cgcccgtcgt    660 tgtttccgat gatggtgcaa tacaggtgaa cggacagtcg aacgtttcgt ttgaccgaaa    720
gttcaccgat atttcttcaa tagaggaagc aaaagtcgta acaaggtagc tgtaggtgaa    780
cctgc                                                                785
```

```
<210> SEQ ID NO 24
<211> LENGTH: 31
<212> TYPE: DNA
<213> ORGANISM: Artificial Sequence
<220> FEATURE:
<223> OTHER INFORMATION: cloning primer

<400> SEQUENCE: 24
aaagcggccg ctagatatgt agagctaccc c                                    31

<210> SEQ ID NO 25
<211> LENGTH: 33
<212> TYPE: DNA
<213> ORGANISM: Artificial Sequence
<220> FEATURE:
<223> OTHER INFORMATION: cloning primer

<400> SEQUENCE: 25
cccggccggc catttctctt cagactgtta ttc                                  33

<210> SEQ ID NO 26
<211> LENGTH: 31
<212> TYPE: DNA
<213> ORGANISM: Artificial Sequence
<220> FEATURE:
<223> OTHER INFORMATION: cloning primers

<400> SEQUENCE: 26
gggagatctt aaatgggata catgggggtg c                                    31

<210> SEQ ID NO 27
<211> LENGTH: 33
<212> TYPE: DNA
<213> ORGANISM: Artificial Sequence
<220> FEATURE:
<223> OTHER INFORMATION: cloning primer

<400> SEQUENCE: 27
gggttaatta agttgaaaaa agaaaaaaac ttg                                  33

<210> SEQ ID NO 28
<211> LENGTH: 31
<212> TYPE: DNA
<213> ORGANISM: Artificial Sequence
<220> FEATURE:
<223> OTHER INFORMATION: cloning primer

<400> SEQUENCE: 28
atagggcccg catggctcat tacatcagac g                                    31
```

<210> SEQ ID NO 29
<211> LENGTH: 32
<212> TYPE: DNA
<213> ORGANISM: Artificial Sequence
<220> FEATURE:
<223> OTHER INFORMATION: cloning primer

<400> SEQUENCE: 29
agacctaggc aacaaaagcc gaaacggtag cc                                    32

<210> SEQ ID NO 30
<211> LENGTH: 33
<212> TYPE: DNA
<213> ORGANISM: Artificial Sequence
<220> FEATURE:
<223> OTHER INFORMATION: cloning primer

<400> SEQUENCE: 30
gggttaatta aatcctcagc acgtttctta ctt                                   33

<210> SEQ ID NO 31
<211> LENGTH: 24
<212> TYPE: DNA
<213> ORGANISM: Artificial Sequence
<220> FEATURE:
<223> OTHER INFORMATION: cloning primer

<400> SEQUENCE: 31
atacccgggc tgcaggcagg ttca                                             24

<210> SEQ ID NO 32
<211> LENGTH: 32
<212> TYPE: DNA
<213> ORGANISM: Artificial Sequence
<220> FEATURE:
<223> OTHER INFORMATION: cloning primer

<400> SEQUENCE: 32
gggggcgcgc ctggcttgtg tttatctatt tc                                    32

<210> SEQ ID NO 33
<211> LENGTH: 27
<212> TYPE: DNA
<213> ORGANISM: Artificial Sequence
<220> FEATURE:
<223> OTHER INFORMATION: cloning primer

<400> SEQUENCE: 33
cccggtacct gttgaaatag taactcg                                          27

<210> SEQ ID NO 34
<211> LENGTH: 29
<212> TYPE: DNA
<213> ORGANISM: Artificial Sequence
<220> FEATURE:
<223> OTHER INFORMATION: cloning primer

<400> SEQUENCE: 34
ggaggcgcgc caaatgggat acatggggg                                        29

<210> SEQ ID NO 35
<211> LENGTH: 31
<212> TYPE: DNA
<213> ORGANISM: Artificial Sequence
<220> FEATURE:
<223> OTHER INFORMATION: cloning primer

<400> SEQUENCE: 35
ggaggtaccg ttgaaaaaaa gaaaaaactt g                                    31

<210> SEQ ID NO 36
<211> LENGTH: 29
<212> TYPE: DNA
<213> ORGANISM: Artificial Sequence
<220> FEATURE:
<223> OTHER INFORMATION: cloning primer

<400> SEQUENCE: 36
gggcctaggg tcgttgttat cgttgtacg                                       29

<210> SEQ ID NO 37
<211> LENGTH: 31
<212> TYPE: DNA
<213> ORGANISM: Artificial Sequence
<220> FEATURE:
<223> OTHER INFORMATION: cloning primer

<400> SEQUENCE: 37
gacggccggc cgaaatagta actcgatatg c                                    31

<210> SEQ ID NO 38
<211> LENGTH: 30
<212> TYPE: DNA
<213> ORGANISM: Artificial Sequence
<220> FEATURE:
<223> OTHER INFORMATION: cloning primer

<400> SEQUENCE: 38
cccggtacca tggccaagcc tttgtctcaa                                      30

<210> SEQ ID NO 39
<211> LENGTH: 32
<212> TYPE: DNA
<213> ORGANISM: Artificial Sequence
<220> FEATURE:
<223> OTHER INFORMATION: cloning primer

<400> SEQUENCE: 39
cccagatctt tagccctccc acacataacc ag                                   32

<210> SEQ ID NO 40
<211> LENGTH: 32
<212> TYPE: DNA
<213> ORGANISM: Artificial Sequence
<220> FEATURE:
<223> OTHER INFORMATION: cloning primer

<400> SEQUENCE: 40
ataggccggc catggccaag cctttgtctc aa                                   32

<210> SEQ ID NO 41
<211> LENGTH: 34
<212> TYPE: DNA
<213> ORGANISM: Artificial Sequence
<220> FEATURE:
<223> OTHER INFORMATION: cloning primer

<400> SEQUENCE: 41
ataggcgcgc cttagccctc ccacacataa ccag                                 34

<210> SEQ ID NO 42

<211> LENGTH: 32
<212> TYPE: DNA
<213> ORGANISM: Artificial Sequence
<220> FEATURE:
<223> OTHER INFORMATION: cloning primer

<400> SEQUENCE: 42
agaggccggc catgtcgagg atgtggctga cc                                    32

<210> SEQ ID NO 43
<211> LENGTH: 31
<212> TYPE: DNA
<213> ORGANISM: Artificial Sequence
<220> FEATURE:
<223> OTHER INFORMATION: cloning primer

<400> SEQUENCE: 43
gggctcgagc ccgccaacct cgctttcacc g                                     31

<210> SEQ ID NO 44
<211> LENGTH: 30
<212> TYPE: DNA
<213> ORGANISM: Artificial Sequence
<220> FEATURE:
<223> OTHER INFORMATION: cloning primer

<400> SEQUENCE: 44
ataggtacca tgtcgaggat gtggctgacc                                       30

<210> SEQ ID NO 45
<211> LENGTH: 38
<212> TYPE: DNA
<213> ORGANISM: Artificial Sequence
<220> FEATURE:
<223> OTHER INFORMATION: cloning primer

<400> SEQUENCE: 45
ataggccggc cactagtatg tcgaggatgt ggctgacc                              38

<210> SEQ ID NO 46
<211> LENGTH: 30
<212> TYPE: DNA
<213> ORGANISM: Artificial Sequence
<220> FEATURE:
<223> OTHER INFORMATION: cloning primer

<400> SEQUENCE: 46
ataagatctt tagaatgcgg caacgagagc                                       30

<210> SEQ ID NO 47
<211> LENGTH: 31
<212> TYPE: DNA
<213> ORGANISM: Artificial Sequence
<220> FEATURE:
<223> OTHER INFORMATION: cloning primer

<400> SEQUENCE: 47
atatctagac ctgaacctgg tgctgcaacg c                                     31

<210> SEQ ID NO 48
<211> LENGTH: 32
<212> TYPE: DNA
<213> ORGANISM: Artificial Sequence
<220> FEATURE:
<223> OTHER INFORMATION: cloning primer

<400> SEQUENCE: 48
ataggcgcgc cttagaatgc ggcaacgaga gc                      32

<210> SEQ ID NO 49
<211> LENGTH: 31
<212> TYPE: DNA
<213> ORGANISM: Artificial Sequence
<220> FEATURE:
<223> OTHER INFORMATION: cloning primer

<400> SEQUENCE: 49
ataaagcttc ctgaacctgg tgctgcaacg c                       31

<210> SEQ ID NO 50
<211> LENGTH: 38
<212> TYPE: DNA
<213> ORGANISM: Artificial Sequence
<220> FEATURE:
<223> OTHER INFORMATION: cloning primer

<400> SEQUENCE: 50
ataggccggc catgttcaat ggcaataatg tgagctgc                38

<210> SEQ ID NO 51
<211> LENGTH: 38
<212> TYPE: DNA
<213> ORGANISM: Artificial Sequence
<220> FEATURE:
<223> OTHER INFORMATION: cloning primer

<400> SEQUENCE: 51
ataggcgcgc cttatccctg acctgatcct gcagcaca                38

<210> SEQ ID NO 52
<211> LENGTH: 33
<212> TYPE: DNA
<213> ORGANISM: Artificial Sequence
<220> FEATURE:
<223> OTHER INFORMATION: cloning primer

<400> SEQUENCE: 52
atacctaggt tcaatggcaa taatgtgagc tgc                     33

<210> SEQ ID NO 53
<211> LENGTH: 33
<212> TYPE: DNA
<213> ORGANISM: Artificial Sequence
<220> FEATURE:
<223> OTHER INFORMATION: cloning primer

<400> SEQUENCE: 53
ataaagcttt ccctgacctg atcctgcagc aca                     33

<210> SEQ ID NO 54
<211> LENGTH: 33
<212> TYPE: DNA
<213> ORGANISM: Artificial Sequence
<220> FEATURE:
<223> OTHER INFORMATION: cloning primer

<400> SEQUENCE: 54
ggaggccggc catgagtcca ctttgaagga aag                     33

<210> SEQ ID NO 55
<211> LENGTH: 33
<212> TYPE: DNA

```
<213> ORGANISM: Artificial Sequence
<220> FEATURE:
<223> OTHER INFORMATION: cloning primer

<400> SEQUENCE: 55
ataggcgcgc ctcgcttgtg cttctcggtt ctc                                33

<210> SEQ ID NO 56
<211> LENGTH: 32
<212> TYPE: DNA
<213> ORGANISM: Artificial Sequence
<220> FEATURE:
<223> OTHER INFORMATION: cloning primer

<400> SEQUENCE: 56
ggaggtacca tgagagtcca ctttgaagga aa                                 32

<210> SEQ ID NO 57
<211> LENGTH: 28
<212> TYPE: DNA
<213> ORGANISM: Artificial Sequence
<220> FEATURE:
<223> OTHER INFORMATION: cloning primer

<400> SEQUENCE: 57
gggagatctc tattcgcttg tgctactc                                      28

<210> SEQ ID NO 58
<211> LENGTH: 30
<212> TYPE: DNA
<213> ORGANISM: Artificial Sequence
<220> FEATURE:
<223> OTHER INFORMATION: cloning primer

<400> SEQUENCE: 58
gggggccggc catggtgagc aagggcgagg                                    30

<210> SEQ ID NO 59
<211> LENGTH: 30
<212> TYPE: DNA
<213> ORGANISM: Artificial Sequence
<220> FEATURE:
<223> OTHER INFORMATION: cloning primer

<400> SEQUENCE: 59
gggggcgcgc cttacttgta cagctcgtcc                                    30

<210> SEQ ID NO 60
<211> LENGTH: 35
<212> TYPE: DNA
<213> ORGANISM: Artificial Sequence
<220> FEATURE:
<223> OTHER INFORMATION: cloning primer

<400> SEQUENCE: 60
ataggccggc catggagaaa aaaatcactg gatat                              35

<210> SEQ ID NO 61
<211> LENGTH: 27
<212> TYPE: DNA
<213> ORGANISM: Artificial Sequence
<220> FEATURE:
<223> OTHER INFORMATION: cloning primer

<400> SEQUENCE: 61
ataggcgcgc cttacgcccc gccctgc                                       27
```

<210> SEQ ID NO 62
<211> LENGTH: 33
<212> TYPE: DNA
<213> ORGANISM: Artificial Sequence
<220> FEATURE:
<223> OTHER INFORMATION: cloning primer

<400> SEQUENCE: 62
gggctcgagg agaaaaaaat cactggatat acc                33

<210> SEQ ID NO 63
<211> LENGTH: 24
<212> TYPE: DNA
<213> ORGANISM: Artificial Sequence
<220> FEATURE:
<223> OTHER INFORMATION: cloning primer

<400> SEQUENCE: 63
atatctagac gccccgccct gcca                24

<210> SEQ ID NO 64
<211> LENGTH: 33
<212> TYPE: DNA
<213> ORGANISM: Artificial Sequence
<220> FEATURE:
<223> OTHER INFORMATION: cloning primer

<400> SEQUENCE: 64
ataggtacca tggagaaaaa aatcactgga tat                33

<210> SEQ ID NO 65
<211> LENGTH: 25
<212> TYPE: DNA
<213> ORGANISM: Artificial Sequence
<220> FEATURE:
<223> OTHER INFORMATION: cloning primer

<400> SEQUENCE: 65
ataagatctt tacgccccgc cctgc                25

<210> SEQ ID NO 66
<211> LENGTH: 35
<212> TYPE: DNA
<213> ORGANISM: Artificial Sequence
<220> FEATURE:
<223> OTHER INFORMATION: cloning primer

<400> SEQUENCE: 66
ataggccggc catggagaaa aaatcactg gatat                35

<210> SEQ ID NO 67
<211> LENGTH: 20
<212> TYPE: DNA
<213> ORGANISM: Artificial Sequence
<220> FEATURE:
<223> OTHER INFORMATION: blotting probe primer

<400> SEQUENCE: 67
acgcagcaag gtggtgcgaa                20

<210> SEQ ID NO 68
<211> LENGTH: 22
<212> TYPE: DNA
<213> ORGANISM: Artificial Sequence
<220> FEATURE:

<223> OTHER INFORMATION: blotting probe primer

<400> SEQUENCE: 68
gcgctgcttc aacactgtca cc                                              22

<210> SEQ ID NO 69
<211> LENGTH: 21
<212> TYPE: DNA
<213> ORGANISM: Artificial Sequence
<220> FEATURE:
<223> OTHER INFORMATION: nested PCR primer

<400> SEQUENCE: 69
agtagcaacg acagcagcag t                                               21

<210> SEQ ID NO 70
<211> LENGTH: 24
<212> TYPE: DNA
<213> ORGANISM: Artificial Sequence
<220> FEATURE:
<223> OTHER INFORMATION: nested PCR primer

<400> SEQUENCE: 70
gtaaagtgtt tgaagaagag ctcg                                            24

<210> SEQ ID NO 71
<211> LENGTH: 21
<212> TYPE: DNA
<213> ORGANISM: Artificial Sequence
<220> FEATURE:
<223> OTHER INFORMATION: nested PCR primer

<400> SEQUENCE: 71
cgattctctt cgcctgtttg t                                               21

<210> SEQ ID NO 72
<211> LENGTH: 21
<212> TYPE: DNA
<213> ORGANISM: Artificial Sequence
<220> FEATURE:
<223> OTHER INFORMATION: nested PCR primer

<400> SEQUENCE: 72
actaaccgcg accaaagaag t                                               21

<210> SEQ ID NO 73
<211> LENGTH: 24
<212> TYPE: DNA
<213> ORGANISM: Artificial Sequence
<220> FEATURE:
<223> OTHER INFORMATION: nested PCR primer

<400> SEQUENCE: 73
atgaaaacca gtaagattct caac                                            24

<210> SEQ ID NO 74
<211> LENGTH: 24
<212> TYPE: DNA
<213> ORGANISM: Artificial Sequence
<220> FEATURE:
<223> OTHER INFORMATION: nested PCR primer

<400> SEQUENCE: 74
tgataccgaa gacaatggca gaca                                            24
<210> SEQ ID NO 75
<211> LENGTH: 24
<212> TYPE: DNA
<213> ORGANISM: Artificial Sequence
<220> FEATURE:
<223> OTHER INFORMATION: nested PCR primer

<400> SEQUENCE: 75
agcgaaggat ggcttcttag gact 24

<210> SEQ ID NO 76
<211> LENGTH: 24
<212> TYPE: DNA
<213> ORGANISM: Artificial Sequence
<220> FEATURE:
<223> OTHER INFORMATION: nested PCR primer

<400> SEQUENCE: 76
tcaacactgc tgctatctgc ctcc 24

<210> SEQ ID NO 77
<211> LENGTH: 798
<212> TYPE: DNA
<213> ORGANISM: Artificial Sequence
<220> FEATURE:
<223> OTHER INFORMATION: enhanced GFP gene

<400> SEQUENCE: 77
atggtgagca agggcgagga gctgttcacc ggggtggtgc ccatcctggt cgagctggac 60
ggcgacgtaa acggccacaa gttcagcgtg tccggcgagg gcgagggcga tgccacctac 120
ggcaagctga ccctgaagtt catctgcacc accggcaagc tgcccgtgcc ctggcccacc 180
ctcgtgacca ccctgaccta cggcgtgcag tgcttcagcc gctaccccga ccacatgaag 240
cagcacgact tcttcaagtc cgccatgccc gaaggctacg tccaggagcg caccatcttc 300
ttcaaggacg acggcaacta caagacccgc gccgaggtga agttcgaggg cgacaccctg 360
gtgaaccgca tcgagctgaa gggcatcgac ttcaaggagg acggcaacat cctggggcac 420
aagctggagt acaactacaa cagccacaac gtctatatca tggccgacaa gcagaagaac 480
ggcatcaagg tgaacttcaa gatccgccac aacatcgagg acggcagcgt gcagctcgcc 540
gaccactacc agcagaacac ccccatcggc gacggccccg tgctgctgcc cgacaaccac 600
tacctgagca cccagtccgc cctgagcaaa gaccccaacg agaagcgcga tcacatggtc 660
ctgctggagt tcgtgaccgc cgccgggatc actctcggca tggacgagct gtacaagtcc 720
ggactcagat ctcgagctca agcttcgaat tctgcagtcg acggtaccgc gggcccggga 780
tccaccggat ctagataa 798

<210> SEQ ID NO 78
<211> LENGTH: 2694
<212> TYPE: DNA
<213> ORGANISM: Dictyocaulus viviparus
<220> FEATURE:
<221> NAME/KEY: misc_feature
<222> LOCATION: (1)..(2694)
<223> OTHER INFORMATION: acetylcholinesterase-1 gene

<400> SEQUENCE: 78
gagattaaag ctgaaattgt catcacatat caccaaaaaa ctcaacgagg gtgttttttt 60
taacgacgtg atctaataga gtacatttgc tatgtgcacg aattagatgc attattgatt 120
gatatgctgt ttgcattgtt tttaagcgca ttaatactgc agtcattaac aatcgatttg 180

```
atctatctac atgatggttc gccacttttt ggtgaagaaa ttctatcacc aaacgggaaa    240
cgcctaacac aattccttgg aattccgttc gctgaacctc ctataggaaa tttgagattt    300
cgaaaaccaa aaccgaaaca gccgtggaga atgccattaa acgccacgat tttaccgaat    360
tcatgcatac agagtttcga cacatatttc ggtgaatttt atggagcgac aatgtggaat    420
ccgaatacac caacatcgga ggattgcctc tatatgaata tcttcgtacc tgggaaaatt    480
gatccgataa aacgtttggc agttatggta tgggtatacg gtggtggatt ctggtccggt    540
acgtcgactt tagatgtata cgatggacga attctaccag tggaagaaaa cgtcattcta    600
gtatcaatga actatcgcgt atcaatgctc ggatttctgt atcttggaag acgtgaagct    660
cctggcaata tgggcctctg ggatcaacag ttagctttga aatgggtcca caaaaatatt    720
gatctgtttg gtggtgatcc agatcgaata tcgcttttcg gggagtcggc aggtgctgcc    780
tctgtaacca tgcacatgtt gagcgctcac agtactccat acttccagag agcgattata    840
caatctggat ctgcaacagc cccttgggct attgaacctc gtgatgtggc attggcacgt    900
acagttatac tctataatgc gatgaaatgt ggcaacatga gtcttcaaaa tccgactat    960 gataagattt tggactgttt tcaacaagct gacgcagatc ttatacgtga aaatgaatgg   1020
gcacctgttc gtgagtttgc tgattttcca tgggttccag ttgtggacgg tgatttcctt   1080
gtagaaagtg ctcagacatc attgaggcaa ggaaacttta aacacacaca acttcttgct   1140
ggaagtaatc ttgacgaaag catgtacttc atcatttatc aacttacgaa tatattccca   1200
gtgaaagatt ttttcacaaa aagagatttt gttccggata gacatacatg gctcagggca   1260
atatcggatc ttcttccacg acaaatgatt aaaagtcaat tagcattagc agcaatacta   1320
cacgagtacg agccagctaa tcttccagtt caagcaaatg attggatgga ttcaatggaa   1380
aaaatgttag gcgattatca ctttacttgt aatgtaaatg aaatggcact tgctcatagt   1440
aaacatggtg gtgatactta ctattattat tttactcata gagcaacagc gcaaacgtgg   1500
ccagaatgga tgggttgttt acatggctat gaaatcaatt ttattttgg tgaaccattc   1560 aataagaaat caactatac taatgaggaa aaagagctta gtagcagatt tatgcgatac   1620
tgggcaaatt tcgctcgaac tggtgatcca aataaaaacg aagatggtac atacacagca   1680
gatgtatggc caaaatacaa ttcacagtca atggagtaca tgaatatgac gattgagtca   1740
gcatatccta atgctcgacg tacaggtcat ggtccacgac gaaagcattg cgcattttgg   1800
aaagcttact taccaaatct tatggcggct gttgctgatg ttggcgatcc atttttactc   1860
tggaaacaac aaatggataa gtggcaaaat gaatacatta cggactggca gtatcatttt   1920
gagcagtaca aaaaatatca gacgtatcga cacctagatt ccgattcatg cagtggatcc   1980
tgaatagaaa aaaacgaca aagttatcaa aaatatcgcc tggtctcacg aaaatatgag   2040
gtggacaagt tcaattaaaa acaaaagaag acgttatata aagatcaag gattcacatc   2100 ttattttcat atgaggaatc gagtgtgttg tttgttttta atgttattga aatgtattca   2160
ttattgattg atttacacaa tatcttctct gctttaccag atttgtcatg cgttaataag   2220
ccacttaata ttcacatttt ctcttattta gagcgaccaa tcaattgtac ctgatcctct   2280
atcttctcgg ttttttcctcc catttctaat actaatgttg ttttccttat tttatttct   2340 gtaaacttgc gttttattaa tcgagtgtca tgtgaacggt atctgtacga acacgatcat   2400
ttatgaatcg gactacattc cagacgggca ttttcatt tacaattcga aaatttgcta   2460
gagaaatgtt atgttgagtg aaacaaaaaa cgatcaccta aatagaacag gtcttattac   2520
gacattcaat attatatagg aatgggtatt gaaaaatata cgtgccctct tcctttttcc   2580
```

```
tctttaaaat ttcattttat tcaaaaaata tttgtttatt acttttccgt tatcattttt    2640
tatttgtttg tatataaaag tgtttataag aaaaaaaaaa aaaaaaaaaa aaaa          2694

<210> SEQ ID NO 79
<211> LENGTH: 81
<212> TYPE: DNA
<213> ORGANISM: Trypanosoma brucei
<220> FEATURE:
<221> NAME/KEY: misc_feature
<222> LOCATION: (1)..(81)
<223> OTHER INFORMATION: GPI anchor

<400> SEQUENCE: 79
cctgaacctg gtgctgcaac gctgaaatcc gttgcacttc cgttcgcaat cgcggctgct    60
gctctcgttg ccgcattcta a                                              81

<210> SEQ ID NO 80
<211> LENGTH: 887
<212> TYPE: DNA
<213> ORGANISM: Babesia divergens
<220> FEATURE:
<221> NAME/KEY: misc_feature
<222> LOCATION: (1)..(887)
<223> OTHER INFORMATION: Bd37 gene core

<400> SEQUENCE: 80
atggcaataa tgtgagctgc accaatctca atggctcaca ggagccagca gcggctaacc    60
ctgttgtttc aactcctggg aatgatgcgc agcaggctgg tacgcagcaa ggtggtgcga    120
actcaaagtc cgttccagag cagcagccac agcaggctgc cggcgaaacc actgctacgg    180
tcgtggtaaa gactctagat gtgctccgtg gggaactcag ggggcagcgt gaggctttcc    240
tttcagagat aattaaatcg gatggtccat tcactatttt gcagttggtt ggctaccttc    300
gtgttgtcga cacagatctt ctcctgaaag ttgattccac gaaggttgat gaagccggca    360
agaaggtcaa ggcctacctt gaaaaaattg gaataagggg tgacagtgtt gaagcagcgc    420
ttgacaatct tatgataaag gtttatgaaa tcaccaaagg tactgtggaa agttcagcac    480
aaggtactga cagtgaggag ctgaagactt tgttattaaa gttcagcgaa gatctcaagg    540
ctgagcaaga acttcatagt gaagccaagg gcggtgaggc cttgctttct agcatgaaga    600
cgcagcatga tgaactactt aagaagtttg ctgcccttac ccctactttc ttaacctcag    660
aggatatatc tggctacctt accgtgccgg aatacggtgc ccctatgaat gctgcgaagt    720
ggaaaaaggt ggaaggaatg atccatggaa agctcgagtc ttccgaagta ccagctaatc    780
tcaaagctct ggttgcagag ttaattgagt tgcgtgaaca gatgatggat ttgctatacg    840
gccctattgg tcatcacgat tgtgctgcag gatcaggtca gggataa                 887
```

RECOMBINANT TRYPANOSOMA THEILERI PARASITE

CROSS REFERENCE TO RELATED APPLICATIONS

This application is a United States Application under 35 U.S.C. 371 claiming benefit of PCT Application No. PCT/GB2011/001154, filed on Jul. 29, 2011, which claims the benefit of European Application No.: 10171304.8, filed on Jul. 29, 2010, as well as U.S. Provisional Application No. 61/370,223, filed Aug. 3, 2010, the contents of each of which are incorporated herein by reference.

The present invention relates to the field of the veterinary medicine of bovine animals. In particular the invention relates to a recombinant *Trypanosoma theileri* parasite, preferably comprising a heterologous nucleic acid sequence that is capable of encoding a protein for instance an antigen, a cytokine, a hormone, an antimicrobial protein, or an antibody. Also disclosed are uses of and methods for making and using the recombinant *T. theileri* parasite in medical or non-curative treatments; in particular as a sustained delivery vector for proteins to bovine animals, e.g. as a vaccine.

Bovine animals are of global social and economic importance, as they are an important source of food (meat and milk), as well as of hides, labour and manure. Consequently, the veterinary medicine of bovine animals is well developed, both for economic, and for health reasons. The health aspect primarily regards the bovine health, but human health is also involved, as zoonoses from bovines to the human species are known; e.g. cross-species infections with bacteria such as Tuberculosis or *E. coli* O157, with Rabies virus, or *Cryptosporidium* parasites. Possible treatments of bovines therefore can be aimed at the prevention of infection or disease, e.g. by vaccination. Alternatively treatment for the improvement of the bovine's production parameters is known, e.g. relating to the quantity and/or quality of meat, milk or offspring. For all these kinds of treatments, the administration of protein is a common practice, such as the application of hormones or the inoculation with a subunit vaccines; this usually requires the addition of an adjuvant to stimulate the animals' immune response.

An alternative route for the delivery of such a protein is via the use of a live micro-organism which has been genetically manipulated to express the desired protein within the target host. Such application route does usually not require an adjuvant. Several live recombinant carrier micro-organisms (LRCM's) are known and can for instance be bacteria (e.g. *Escherichia coli* or *Salmonella* sp. [Roland et al., 2005, Curr. Opin. Mol. Ther., vol. 7, p. 62-72]); or viruses (e.g. vaccinia virus [Panicali et al. 1982, PNAS USA, vol. 79, p. 4927]; or Herpesvirus [EP 0473210-A2]). Also parasites have been described as LRCM (Vermeulen et al., Int. Journ. Parasitol. 1998, vol. 28, p. 1121-1130).

*Trypanosoma theileri* (further: *T. theileri*) is a unicellular and uniflagellated protozoan parasite, which in one phase of its life-cycle (the blood-stream form) lives free in the bloodstream of bovine animals, hence its indication as a haemoflagellate, or a haemoparasite. In the other phase of its lifecycle the parasite replicates in an arthropod vector. *T. theileri* exclusively infects bovine animals, of all age groups, and occurs world-wide. Reports on trypanosomatid infection of deer and antelope relate to separate "*T. theileri*-like" species (Böse et al., 1993, Parasitology vol. 107, p. 55-61; Rodrigues et al., 2006, Parasitology vol. 132, p. 215-224).

The determination of the *T. theileri* species and its developmental stages is commonly done by morphology, observed by light microscopy. Characterising features are its relatively large size, as well as morphometrics of the flagellum: the size, shape and emergence-point of the flagellum, as well as the location of the intracellular kinetoplast in relation to the cells' nucleus and the posterior end of the cell body.

The parasite's insect vectors are Tabanidae; biting flies such as horse flies (Böse et al., 1987, Parasitology Research, vol. 73, p. 421-424). Some reports also describe a role for ticks in the transfer and development of *T. theileri* parasites (Morzaria et al., 1986, Vet. Parasitol., vol. 19, p. 13-21). Seasonal variation of the insect vector occurs, with highest prevalence numbers occurring in the summer season.

The number of animals carrying *T. theileri* parasites is generally high, for cattle this can be up to 90%. However, the high prevalence is matched by very low parasitaemia of *T. theileri* in infected bovines, at an average number of 10-100 parasites per ml of blood. The true numbers of *T. theileri* incidences are not always reliably determined by way of light microscopy of Giemsa-stained blood smears. Therefore isolation by culturing is commonly applied; either by direct culture of a blood sample, or (more effectively) by cultivation of peripheral blood lymphocytes after isolation of a buffy coat.

The only 'parasitic effect' of a *T. theileri* infection in a bovine host seems to be its energy consumption; the bloodstream form of the parasite is believed to survive on the abundant glucose in the blood, and employs an inefficient glucose-only type metabolism (reviewed by Tielens & van Hellemond, 2009, Trends in Paras., vol. 25, p. 482-490). However, the relatively low numbers at which *T. theileri* occurs in the host in practice makes this a negligible effect.

Therefore, *T. theileri* is generally considered not to be pathogenic. In fact the few cases where *T. theileri* has been suspected to be involved in a case of bovine disease are so rare that they warranted specific case reports. Generally these cases involved animals already severely ill or immunocompromised (Lamy et al., 1967, Bull. Acad. Vet. Fr., vol. 40, p. 323-325; and Ward et al., 1984, Aust. Vet. J., vol. 61, p. 324). Alternatively these could be a case of misdiagnosis of infection with a pathogenic species of *Trypanosoma* infecting cattle, such as *T. brucei* (Doherty et al., 1993, Vet. Rec., vol. 132, p. 653-656). A consequence is that no treatments using drugs or vaccines have been developed for *T. theileri*, and very little interest exists in the field for this micro-organism. Given its ubiquitous presence in bovines, at low numbers, its non-pathogenic nature, and its long-term co-existence with its bovine host, *T. theileri* is considered to be a bovine commensal micro-organism (Rodrigues et al., 2006, Parasitology, vol. 132, p. 215-224).

*T. theileri* is also referred to as "*T. (Megatrypanum) theileri* (Laveran, 1902)", indicating its first description in 1902, and its taxonomic placing in the subgenus *Megatrypanum*, of which it is the type-species. The subgenus *Megatrypanum* is an obscure subgroup of relatively large *Trypanosoma* parasites, containing a number of species that are infectious to a wide variety of mammals. Most of these have not been studied in any detail (Böse et al., 1993, Parasitology vol. 107, p. 55-61). The *Trypanosoma* are further classified into two sections, whereby the *Megatrypanum* trypanosomes are placed in the *Stercoraria*. This is a grouping of diverse species of *Trypanosoma* which share the way their infection is transferred: in the insect-bound stage of the parasite lifecycle, these parasites replicate in the insects' midgut and hindgut, and infection occurs by 'stercorarian' route: faecal material from the insect vector containing infectious metacyclic stage parasites contaminates the bite-wound or the oral mucosa of the host.

The best known of the stercorarian trypanosomes is *T. cruzi*, which causes Chagas' disease in humans. Unlike *T. theileri*, *T. cruzi* is highly pathogenic, and is transferred by a different type of vector (reduviid bugs). Further differences are that *T. cruzi* causes high parasitaemia, mainly infects humans, and occurs only in Central- and Southern America. Significant difference to *T. theileri* is also that in its host, *T. cruzi* exclusively replicates intracellularly.

The other section of the *Trypanosoma* classification contains the so-called Salivarian trypanosomes, for which the epimastigote forms gather in the insect's salivary glands, then generate infectious metacyclic forms, which are transferred upon the bite of the insect vector. This taxonomic section contains most of the well-known and pathogenic species of *Trypanosoma*, such as *T. brucei*, of which two subspecies (*T. br. rhodesiense* and *T. br. gambiense*) cause human African trypanosomiasis, or: sleeping disease. African trypanosomiasis of animals (also called: Nagana when occurring in cattle) is caused by al three subspecies of *T. brucei* and by the salivarian Trypanosome species *T. congolense* and *T. vivax*.

While these last two species have not been studied as much, *T. brucei* is the most studied trypanosome of all. *T. brucei* parasites do live free in the bloodstream, like *T. theileri*, but there are significant differences to *T. theileri*, for instance:

in their biology: *T. brucei* only occurs in sub-Saharan Africa, and is highly pathogenic. *T. brucei* is transferred by a different vector (tse tse flies), and gives high parasitaemia of over $10^5$ parasites per ml blood.

in their molecular biology: *T. brucei* has developed a highly specialised and complicated system to actively escape the hosts' immune system. This is achieved by periodic change of its outer antigenic coat, formed by the variant surface glycoproteins (VSG's). An additional pool of VSG genes in *T. brucei* is provided by genomic structures called minichromosomes; *T. theileri* does not contain such minichromosomes and it is doubted if *T. theileri* applies any cycling of VSG's at all (Böse et al., 1993, supra).

Even more remotely related to *T. theileri* are the parasites of the genus *Leishmania*. These share with the *Trypanosoma* the presence of a cellular organelle called a kinetoplast, leading to their joined classification in the order of the Kinetoplastida.

*Leishmania* parasites are essentially different from *T. theileri*, mainly because they are generally pathogenic, occur at high parasitaemia levels, are transferred by a different type of vector (sand flies), are inoculated via the byte of the vector, and survive and develop in the target host intracellularly inside macrophages, where they require a special vacuole, and loose their flagellum.

General aspects of Trypanosomatid genome organisation and molecular biology have become known for instance from the 'TriTryp' project, which analyses the genomes from *T. brucei*, *T. cruzi*, and *L. major*. While a general conservation of genome-organisation was observed, substantial species-specific differences were found, linked to the distinct habitats and resulting differences in selection-pressures endured by these different trypanosomatids (Clayton et al., 2000, Mol. & Biochem. Parasitol. vol. 105, p. 163-167; El-Sayed et a, 2005, Science vol. 309, p. 404-409).

Although never described, *T. theileri* is expected to have some of these general features of genome organisation and molecular biology in common with other trypanosomes, mainly: the polycistronic genome organisation, and the fact that gene expression may be primarily regulated at the post-transcriptional level. This means that the amount of RNA and protein in different life cycle stage is regulated by the sequence of the 3' untranslated region of the mRNA. In the genome, these sequences are located in the intergenic untranslated regions, and are highly variable. The resulting level of protein expression is thus a summation of trans-splicing, polyadenylation, and the stability of the mRNA and the protein produced (Palenchar & Bellofatto 2006, Mol. & Biochem. Parasitol., vol. 146, p. 135-141).

The use of *T. brucei* and *T. cruzi* in recombination and expression has been described (Eid & Sollner-Webb, 1991, PNAS USA, vol. 88, p. 2118-2121; Kelly et al., 1992, Nucl. Acids res. vol. 20, p. 3963-3969).

Overall, very little is known of the *T. theileri* genome organisation and molecular biology, and apart from possibly conserved general features, many publications describe explicit differences that exist between the Trypanosomatids in general, and between *T. cruzi*, *T. brucei* and *T. theileri* in particular: the low degree of sequence conservation, particular in the intergenic regions (Clayton, El-Sayed et al., both supra), and the significant differences in metabolism (Tielens & van Hellemond, 2009, Trends in Parasitol., vol. 25, p. 482-490).

The little sequence-information that is available for *T. theileri* in public databases such as Genbank®, is derived from studies into species determination using gene-sequences from GAPDH, and rRNA genes (Rodrigues et al., 2010, Parasitology vol. 137, p. 111-122).

*T. theileri* is unique in being a bovine commensal parasite with global presence, but it is unknown how *T. theileri* manages to sustain such a commensal status in a way that it can survive for years in its bovine host. There have been reports of the detection of an antibody response against *T. theileri* in naturally infected bovines, but this is of relatively low level, and does not seem to be correlated to parasitaemia levels. Cellular immunity against *T. theileri* has also been described, in the form of antibody dependent cytotoxicity, mainly by polymorphonuclear leucocytes (Townsend & Duffus, 1982, Clin. Exp. Immunol., vol. 48, p. 289-299). Clearly neither of these immune responses precludes the parasite's sustained existence.

It is therefore expected that *T. theileri* has developed some way to overcome the hosts' immune response, for instance by inducing immune-tolerance or immune-suppression in the host, or by applying immune-evasion mechanisms, but it is not known how this is accomplished, and for none of these routes there are clear indications: induction of immune-tolerance or -suppression is not likely as bovine carriers do not show any signs of such effect. Similarly, the absence of minichromosomes in *T. theileri* indicates that in *T. theileri* the mechanism of VSG change is not as important as in *T. brucei*, if it occurs at all. Neither does *T. theileri* use the escape-route applied by *T. cruzi*, by hiding within the hosts' cells.

Consequently, *T. theileri* has developed a unique biology of commensalism with its specific host, the bovine animal, which is unlike that of any other known protozoan parasite.

In has now surprisingly been found that a recombinant *T. theileri* parasite could still survive in its bovine host.

Such a recombinant *T. theileri* parasite has advantageously been used to comprise a heterologous nucleic acid, which was capable of encoding a heterologous protein. The recombinant *T. theileri* parasite was used as a sustained delivery vector for heterologous proteins to bovine animals.

Therefore the invention relates to a recombinant *Trypanosoma theileri* parasite.

The term "recombinant" relates to a *T. theileri* parasite of which the genetic material has been mutated by deliberate genetic modification and human intervention.

For the invention; the mutation of the genetic information of *T. theileri* is a substitution, a deletion, or an addition of a nucleic acid sequence, or combinations thereof.

A wildtype *T. theileri* parasite for use in the invention can readily be obtained, for instance from the collection of the American type culture collection (ATCC) (Manassas, Va., USA), under ATCC number 30017. Alternatively, a wild type *T. theileri* parasite may be obtained by isolation from the blood of a bovine animal, using methods as described herein. As most of the commercial cattle are positive for *T. theileri*, a positive sample is easily obtained. Techniques described herein then allow its cultivation, and standard techniques allow a person skilled in the art to make the positive identification as a *T. theileri* parasite.

It will be understood by a skilled person that while the parasite that is used for the invention is currently named *T. theileri*, this is a taxonomic classification which may be subject to change as new insights could lead to reclassification into a new or other taxonomic group. However, as this does not change the micro-organism involved or its characterising features, only its name or classification, such re-classified organisms are considered to remain within the scope of the invention.

For the invention, a "bovine animal" relates to domestic (taurine) cattle, but also to bison, buffalo, zebu, and yak.

The recombinant *T. theileri* parasite according to the invention is preferably alive. This has advantageously allowed the parasite to replicate after inoculation into a bovine animal. Its sustained presence then provided expression and delivery to a bovine animal of a protein over an extended period of time.

Therefore in a preferred embodiment, the invention relates to a recombinant *T. theileri* parasite according to the invention, wherein the parasite is alive.

The use of a live *T. theileri* parasite according to the invention as a live recombinant carrier micro-organism for the expression and delivery of a protein, has several specific advantages over the use of other LRCM's, an inactivated micro-organism, or a subunit protein. For instance:

*T. theileri* is naturally restricted to a single species of host animals, therefore a spread or cross-over infection to other species, e.g. to humans, is highly unlikely.

When applied in its live infectious state, only low doses of the recombinant parasite are required to inoculate the host animal, as the parasite will replicate itself and so populate the target.

The infection with a *T. theileri* parasite as such does not noticeably affect the hosts' health or performance. Also, because of the natural non-pathogenic character of the *T. theileri* parasite, there is no need for complex measures for its attenuation, and there is no chance of any back-mutation to a pathogenic state, even upon its prolonged existence in the host.

In addition, the low replication rate reduces the relevance of any selection pressure against the recombinant parasites carrying a mutation, by any co-infecting non-recombinant *T. theileri* parasites that could otherwise be replicating faster and thus could overgrow the recombinant.

In that respect, the inventors were surprised to note that the inoculation and establishment of an effective infection and the heterologous gene-expression by a recombinant *T. theileri* could still be effected in a bovine animal that was already infected with *T. theileri*, whereas a *T. theileri* negative animal did not suffer any pathology from infection with the recombinant *T. theileri*.

A favourable consequence is that it does not matter whether the bovine animal to which the recombinant *T. theileri* according to the invention is administered, is already positive or is negative for the *T. theileri* parasite. Because most bovines will indeed be carriers, this makes commercial veterinary application to the general bovine population possible.

Materials and methods to make a wildtype *T. theileri* parasite into a recombinant are described herein, and for instance employ the transfection with a DNA molecule, the homologous recombination between the parasite's genome and the DNA molecule, and the selection of recombinant *T. theileri* parasites. With the details described herein these can be readily applied by a person skilled in the art.

This way the inventors have been able to generate for the first time a recombinant *T. theileri* parasite according to the invention wherein the mutation is the addition of a nucleic acid sequence, for instance a restriction enzyme recognition-site. An other example is an immunostimulatory nucleic acid, e.g. carrying a CpG motif.

Therefore in a preferred embodiment of the recombinant *T. theileri* parasite according to the invention, the recombinant comprises an additional nucleic acid sequence.

An "additional" nucleic acid sequence is a nucleic acid sequence that is added to the genome of the *T. theileri* parasite that is used as starting isolate. The addition may be by insertion and/or (partial) replacement of existing genomic nucleic acids. The additional nucleic acid sequence may be a foreign sequence, or an additional copy of a sequence already occurring in the *T. theileri* parasite genome.

In order for the additional nucleic acid sequence to provide a useful function, said sequence needs to be of a certain length; the minimal length for providing an additional function, is that of a restriction enzyme recognition-site of 4 nucleotides.

Therefore, the additional nucleic acid sequence in a recombinant *T. theileri* parasite according to the invention, is minimally 4 nucleotides long; longer sequences can also be used advantageously.

In a more preferred embodiment, the additional nucleic acid sequence, is a sequence that occurs originally in the genome of the wild type *T. theileri* isolate, but that is provided in one or more additional copies. For example this allows the over expression of certain advantageous features.

In an alternate more preferred embodiment, the added nucleic acid sequence is a heterologous nucleic acid sequence, which provides the recombinant *T. theileri* parasite according to the invention with an additional function, such as a genetic or biological marker not previously present in the *T. theileri* parasite used to make the recombinant. This can advantageously be used for instance for tracking and studying of the recombinant *T. theileri* parasite itself e.g. in a bovine host animal. However, most favourably this is used for the cloning and manipulation of further *T. theileri* recombinants. Restriction enzyme sites such as: FseI, AscI, XbaI, XhoI, KpnI, BglII, HindIII have been introduced into the genomic DNA of a *T. theileri* parasite in the course of experiments described herein, and these were stably replicated, and transcribed by the recombinant *T. theileri* parasites both in vitro an in vivo. Preferably more than one heterologous nucleic acid sequences were introduced into the *T. theileri* genomic DNA.

Therefore in a more preferred embodiment, the invention relates to the recombinant *T. theileri* parasite according to the invention, comprising at least one heterologous nucleic acid sequence.

The generation of a recombinant *T. theileri* parasite comprising a heterologous nucleic acid sequence according to the invention was possible by using methods and materials described herein.

The term "heterologous" is to be interpreted in relation to the wild type *T. theileri* parenteral isolate. Therefore a heterologous nucleic acid sequence for the invention is a nucleic acid sequence that did not occur in the wildtype *T. theileri* parasite that was used to generate the recombinant *T. theileri* parasite according to the invention.

The heterologous nucleic acid sequence for use in the invention is preferably a DNA molecule. The DNA molecule can be a cDNA or a fragment thereof, or can itself be a recombinant DNA molecule. It may be of natural or artificial origin.

The heterologous nucleic acid sequence for use in the invention is preferably integrated into the genome of the *T. theileri* parasite. The stable integration into the genome of the recombinant *T. theileri* parasite according to the invention has the advantage that there was no need to transfect every time (as in transient transfection), or that no selection pressure needed to be applied to maintain the recombinant phenotype (as in the case of maintaining an episomal element inside the parasite). Exemplary was the finding that a recombinant *T. theileri* expressing a CAT protein as a marker, stably expressed this heterologous protein in an in vitro culture for 55 days without application of any drug-selection.

Therefore in a still more preferred embodiment of the recombinant *T. theileri* parasite comprising a heterologous nucleic acid sequence according to the invention, the nucleic acid sequence is stably integrated into the parasite's genome.

Typically a heterologous nucleic acid sequence for use in the invention can be one or more of: a restriction enzyme recognition sequence; a gene-regulatory sequence such as a promoter, an enhancer, an mRNA stability/instability element, or an operator element; a mobile genetic element e.g. a transposon; a genetic element for site-specific recombination, e.g. a Cre-Lox element; or a nucleic acid sequence capable of encoding a protein, such as an open reading frame, a gene, or a gene-fragment.

One additional advantage of the use of a *T. theileri* parasite as a recombinant vector for heterologous nucleic acid sequence inserts is that because of the mega-base size of the parasite's genome, the size or the number of inserted nucleic acid(s) does not quickly become limiting to the vector's ability to replicate, as compared to LRCM's of much smaller size, such as a small virus.

Preferably the heterologous nucleic acid sequence for use in the invention is capable of encoding a heterologous protein, i.e. a protein not present in, or not encoded by the wildtype *T. theileri* parenteral isolate. In that respect a heterologous protein according to the invention, while heterologous to the recombinant *T. theileri*, can thus be a protein that is homologous to the bovine host.

In this embodiment the recombinant *T. theileri* parasite according to the invention serves as a vector, i.e. an LRCM. This allowed the advantageous expression and the delivery of a desired heterologous protein to a bovine animal.

Therefore in a still more preferred embodiment, the invention relates to a recombinant *T. theileri* parasite comprising a heterologous nucleic acid sequence according to the invention, wherein the heterologous nucleic acid sequence is capable of encoding at least one heterologous protein.

It was totally unexpected that a commensal organism like *T. theileri* could still survive and prosper for a long time in its host even when it expressed a protein that was heterologous to the parasite, especially when that protein was also heterologous to the bovine host.

Apparently, the mechanism of immune evasion that is applied by *T. theileri* for its long-term survival in a bovine host did not prevent it from effectively expressing a heterologous protein, even to concentrations where therapeutic or prophylactic efficacies are reached. At the same time, the expression of a heterologous protein did not cause the recombinant *T. theileri* to become more exposed to the bovine host's immune system, as it did not lead to an enhanced immune-clearance of the parasite.

In one advantageous embodiment the expression of a desired heterologous protein was obtained from more than one copy of a nucleic acid sequence capable of expressing the heterologous protein comprised within the recombinant *T. theileri* parasite according to the invention. This way the amount of the heterologous protein expressed was effectively increased over a recombinant expressing only from a single insert.

Preferably, the recombinant *T. theileri* parasite according to the invention is made to express more than one different heterologous proteins. This enables the production of multiple heterologous proteins, which in turn can have an interaction with each other, such as the assembly of a bio-active molecule or -structure, or one protein may be useful to steer or improve the biological effect of an other expressed protein.

The multiple copies of the heterologous nucleic acid, encoding the same or different heterologous protein can be inserted in the same or in separate genetic locations of the recombinant *T. theileri* according to the invention. This provides flexibility in optimising the expression and interaction possibilities. Instructions and details to allow a skilled person to construct a recombinant *T. theileri* parasite according to such a preferred embodiment, are provided herein below.

The concept of a nucleic acid being "capable of encoding a protein" is well known in the art, and relates to the central dogma of molecular biology wherein a DNA is transcribed into RNA, and the RNA is translated into a protein. Typically such a nucleic acid sequence capable of encoding a protein is called an open reading frame (ORF), indicating that no undesired stop-codons are present that would prematurely terminate the translation into protein by a ribosomal structure. Said nucleic acid may be a gene (i.e. an ORF encoding a complete protein), or be a gene-fragment. It may be of natural or artificial origin.

As is also well known in the art, in order for a nucleic acid sequence to actually be capable of encoding a protein, the nucleic acid needs to be provided with the proper regulatory signals, for instance being operatively linked to a promoter and a stop codon when the nucleic acid is a DNA, or to a polyA tail when the nucleic acid is an mRNA. In the context of the recombinant *T. theileri* parasite according to the invention all the necessary signals were provided by the parasite's replicative machinery, e.g. the sequences that flanked the inserted heterologous nucleic acid, as is described herein.

Heterologous nucleic acid sequences capable of encoding a protein according to the invention are well known in the art, or can be obtained through standard molecular biological techniques. Details and examples thereof are provided below.

For the invention a "protein" is a molecular chain of amino acids. A protein is not of a specific length, structure or shape and can, if required, be modified in vivo or in vitro, by, e.g. glycosylation, amidation, carboxylation, phosphorylation, pegylation, or changes in spatial folding. Inter alia, peptides, oligopeptides and polypeptides are included within the definition of protein. A protein can be of biologic or of synthetic origin. The protein can be a native or a mature protein, a pre- or pro-protein, or a functional fragment of a protein.

The encoded heterologous protein according to the invention may in principle be any protein or any type of protein, provided it can be effectively expressed by a recombinant *T. theileri* parasite according to the invention in a bovine host. Consequently, the encoded protein should not significantly interfere with the recombinant parasite's maintenance in vivo.

The protein can for example be an antigen, a hormone, a cytokine, an antibody, an enzyme, a receptor, an antibiotic resistance factor, or a structural- or an antimicrobial protein. Preferably the protein's biologic source is a virus, a bacterium, a parasite (not being the *T. theileri* strain from the starting isolate), or another eukaryotic cell or -organism.

Preferably the heterologous protein encoded according to the invention is an antigen, a cytokine, a hormone, an antimicrobial protein or an antibody.

Therefore in a still even more preferred embodiment of the recombinant *T. theileri* parasite comprising a heterologous nucleic acid sequence, wherein the heterologous nucleic acid sequence is capable of encoding at least one heterologous protein, according to the invention, the heterologous protein is a protein or protein-fragment selected from the group consisting of: an antigen, a cytokine, a hormone, an antimicrobial protein or an antibody.

These types of proteins are all well-known in the art:

An "antigen" is a molecule that is recognised by the immune system and induces an immunological response. The response may originate from the innate or the acquired immune system, and may be of the cellular and/or the humoral type. For the invention, the antigen is a protein.

A "cytokine" comprises i.a. an interleukin, an interferon, a tumour necrosis factor, or a colony stimulating factor.

A "hormone" is a molecule released in one part of a eukaryote's body, affecting cells in other parts which express the required receptor for the hormone. For the invention a hormone is a protein.

An "antimicrobial protein" for the invention is a protein with microbiocidal or microbiostatic activity for e.g. a virus, bacterium, fungus or parasite.

An "antibody" is an immunoglobulin or an immunologically active part thereof, for instance a fragment that still comprises an antigen binding site, such as a single chain antibody or a Fab, Fv, scFv, dAb, Fc or Fd fragment, all well known in the art.

The encoded protein according to the invention was advantageously delivered to the bovine host through expression by the recombinant *T. theileri* parasite according to the invention, which circulated in the hosts' bloodstream. This generated an advantageous biological effect in the bovine host.

The encoded heterologous protein according to the invention is preferably biologically active in the bovine host; for example if it is a hormone or a cytokine. When it is an antibody or fragment thereof, it is preferably active in a bovine animal, either because it is a bovine antibody (fragment) of itself, or because it has been adapted to appear like one, i.e. it was 'bovinised'.

Alternatively, the antigen is preferably an antigen of a bovine pathogen. Suitable and preferable antigens from bovine pathogens are described in detail below.

In addition, any one of the heterologous proteins for use in the invention can itself be effective as an antigen; for instance when the protein is a cytokine, it may have its proper biological activity, but it may also induce an immune response in the bovine host against such as an interferon, causing a reduction to, or a stimulation of, a further immunological effect.

The immune response against a protein for use in the invention may have a prophylactic or therapeutic effect in the bovine host. This relates to the fields of vaccines and pharmaccines, wherein a 'pharmaccine' is known as a therapeutic vaccination. Aspects of both are described in detail below.

In an alternate preferred embodiment the encoded protein has been designed to cause such an immune response, and no longer its proper biological effect, for example a cytokine or hormone genetically manipulated to be biologically inactive as a cytokine or hormone, but still being immunogenic.

The advantageous use, or advantageous effect of that use, of the encoded protein according to the invention is in the manipulation of the bovine hosts' performance, by improving its health and/or its production related output parameters, whereby commonly the health and economic performance are related. Examples are the protection from diseases, and the enhancement of performance related output parameters.

Protection from disease can be achieved by the expression and delivery in a bovine animal of a protein which serves as a protective antigen of a bovine pathogen. This way an effective vaccination is applied. Examples are described below.

Alternatively, performance related output parameters, are for example the quantity and/or quality of meat, milk, or off-spring; feed conversion; growth rate; etc. Milk quality is for instance determined by its composition, and ratio of fat to protein. Similarly meat quality is judged on composition, leanness, tenderness, and fat-ratio.

Similarly, fertility regulation can be achieved by influencing the moment of oestrus, such as by speeding up, delaying, or synchronisation of oestrus. Also immune-castration is an option.

Examples of the use of hormones expressed and delivered by a recombinant *T. theileri* parasite according to the invention are for instance: luteinising hormone and follicle-stimulating hormone, or their releasing hormones (GNRH, or LHRH) for regulation or stimulation of fertility; growth hormone, somatostatin, or somatotropin to regulate growth, and aspects of feed-conversion, meat quantity and -quality; oxytocin for milk-production; leptin for influencing fat levels or feed conversion.

Alternatively, cytokines such as bovine interferons or interleukins can be used to stimulate the animal's immune system, and thereby improve its overall health. This for instance affects the animal's resistance to infections and the consequences thereof.

Examples of expressed proteins that are not themselves a protective antigen from a bovine pathogen but which may still serve as an antigen by causing an immune response, are e.g. gonadotropin-releasing hormone or sperm antigens to induce immune-castration; myostatin to enhance muscle growth; or a bovine cytokine, to reduce an unfavourable activity of the immune-system.

Manipulations to make proteins immunogenic, or more immunogenic then they would otherwise be, are known, and comprise for instance the attachment into a fusion protein of antigenic epitopes, or immune-stimulatory molecules.

A further application is the expression and delivery of antibodies (or fragments thereof) to induce a passive immunity in a bovine animal. This may be very helpful if for any reason the generation of an active immunity (by expression of an antigen) is not possible or not desired. One example is the application as a marker vaccine, when it is required to distinguish infected animals from vaccinated ones; a passively vaccinated bovine would only be positive for the antibody, not for the antigen of the pathogen tested for. Another useful application is the suppression of a biological effect in the bovine animal, to which a proper active immunisation would be unfavourable, for instance because that would generate an anti-self immunity. In stead, the gentle provision of passive immunity can effectively inactivate such a biological effect without negative side effects.

In all these applications an additional advantage of the use of the recombinant *T. theileri* parasite according to the invention is that the treatment of the bovine animal can effectively be terminated when desired, by simply stopping the replication of, or killing, the recombinant *T. theileri* parasites, for instance by administration of an effective dose of an antiparasitic drug for which the recombinant is sensitive, for example Bleomycin (or Phleomycin), Blasticidin, Amphotericine, Puromycin, Neomycin, and/or Hygromycin. Preferred is the use of Bleomycin at 10 mg/kg.

As is well known in the art, for an encoded protein according to the invention to have an advantageous biological effect, the protein or protein-fragment will need to have a minimal size and quality.

For example when a protein is used as an antigen for e.g. vaccination purposes or for raising antibodies, it is not always necessary to use the whole protein, rather it is possible to use an immunogenic fragment of that protein that is capable (as such or coupled to a carrier such as e.g. KLH, tetanus toxin or BSA) of inducing an immune response against that protein.

For the invention an "immunogenic fragment" is understood to be a fragment of a full-length protein that still has retained its capability to induce an immune response in a vertebrate host, i.e. comprises a B- or T-cell epitope. When the fragment represents a linear epitope, the fragment needs to be at least 8 amino acids in length; this because it is well known that, to be properly presented and recognised to the immune system, a peptide needs to be of a minimal length: 8-11 aa for MHC I receptor binding, and 11-15 aa for MHC II receptor binding (e.g. as reviewed by Germain & Margulies, 1993, Annu. Rev. Immunol., vol. 11, p. 403-450).

Several techniques are available for the selection of immunogenic fragments from protein antigens, such as the PEPSCAN technique (Geysen et al., 1987, J. Imm. Meth. vol. 102, p. 259-274). This (empirical) method is especially suitable for the detection of B-cell epitopes. T-cell epitopes can be predicted from the sequence by computer with the aid of Berzofsky's amphiphilicity criterion (1987, Science, vol. 235, p. 1059-1062).

Similarly, for a protein intended to be biologically active as a hormone, enzyme, cytokine, or antimicrobial protein, this protein will need to at least comprise its active centre. Ways to determine such a minimal size are well known in the art, and involve assays detecting biological or biochemical activity.

Similarly, the quality of the encoded protein is well known to be dependent from post-translational processing such as folding and glycosylation. This is advantageously provided by the context of the live recombinant *T. theileri* parasite and its host. Therefore, the recombinant *T. theileri* parasite according to the invention is advantageously used in particular for the expression of mammalian derived proteins, or proteins from a parasitic organism which may be difficult to express in an other recombinant expression system. This advantageously contributes to their biological efficacy in vivo.

Preferably the desired protein quality is achieved by manipulation of the nucleic acid encoding the protein. One advantageous embodiment is the deliberate targeting of the encoded protein to a specific cellular or organismal location. For example the protein encoded by a recombinant *T. theileri* according to the invention can be manipulated to remain inside the parasite cell; to be expressed on the parasite's surface; or may be secreted out of the parasite cell, and into the parasite's surroundings.

As is well known in the art, choosing one or the other route for the encoded protein will determine the way the protein is processed. For instance when the protein remains inside the parasite cell, it will not pass through the Golgi apparatus, and therefore it will not be glycosylated.

By choosing a delivery route for the encoded heterologous protein, it is determined where and how the encoded protein is targeted to the bovine host, and to its immune system, ergo: its biological effect in the bovine animal. For example, targeting the expressed protein to remain within the recombinant *T. theileri* cell, will make that the heterologous protein only becomes biologically available upon the rupture or clearance of the parasite vector, or upon the subsequent presentation to the immune system by antigen presenting cells. Alternatively, targeting for presentation on the parasite surface or for secretion outside of the parasite cell, will make that the heterologous protein is biologically available constantly. Dependent on the type of the heterologous protein, and the biological activity desired, one route is more effective than another.

Molecular signals for the targeting of encoded proteins are well known in the art and can be an N-terminal signal sequence and/or a C-terminal anchor or -hydrophobic region. For example these are reviewed in handbooks such as: "Molecular biology of the cell", B. Alberts ed., Garland Science publishers 2007, ISBN: 0815341067.

Therefore in a further preferred embodiment of the invention, the encoded heterologous protein is targeted to remain inside the parasite cell, or is targeted for secretion outside of the parasite cell.

A very advantageous use of the recombinant *T. theileri* parasite according to the invention is in the use for the expression of a wide variety of proteins (or fragments thereof) and the delivery thereof to a bovine host, to cause a desired (veterinary) effect. In this embodiment the recombinant *T. theileri* parasite according to the invention is a live recombinant carrier micro-organism, for expression and delivery of proteins to its host. However, one additional advantageous aspect of using *T. theileri* as an LRCM is that this makes advantageous use of the sustained presence of *T. theileri* in its host: the expression and delivery of protein by the recombinant *T. theileri* according to the invention continues in a sustained way from the moment of inoculation of the bovine with the recombinant parasite, to as long as the parasite survives; in principle till the end of the life of the bovine host. Expression was demonstrated to extend and accumulate for at least 13 weeks.

Therefore, in a further aspect, the invention relates to a method for sustained delivery of a protein to a bovine animal, comprising the inoculation of said bovine animal with the recombinant *T. theileri* parasite according to the invention.

Alternatively a further aspect of the invention relates to the recombinant *T. theileri* parasite according to the invention, for use as a sustained delivery vector for bovine animals.

And a still further aspect of the invention relates to the use of the recombinant *T. theileri* parasite according to the invention, for the manufacture of a composition comprising a sustained delivery vector for bovine animals.

The "inoculation" of a bovine animal with a recombinant *T. theileri* according to the invention comprises administering a dose of life recombinant *T. theileri* parasites according to the invention to a bovine animal, and thereby initiating the infection of the bovine and the proliferation of the parasite in that bovine. The inoculation can be performed by parenteral route, i.e. through all routes of injection into or through the skin, for example: intramuscular, intravenous, intraperitoneal, intradermal, submucosal, or subcutaneous. Alternatively, inoculation may be by direct application to mucosal epithelium e.g. of the eye, nose, mouth, anus, or vagina, as a drop, spray, gel or ointment.

Preferred application routes are intramuscular or subcutaneous injection, or application to the oral mucosa. Preferably the vaccine is in the form of an injectable liquid.

Details of dosing- and application schedules are described below.

The sustained delivery vector according to the method and its use for the invention makes advantageous use of the prolonged, stable expression and presentation to the bovine host by the recombinant *T. theileri* according to the invention, as it survives as a commensal micro-organism in a bovine host animal.

Although the naturally low parasitaemia of a *T. theileri* parasite causes the amount of protein that is presented to a host to be relatively low when compared to for instance a common dose of subunit vaccine, or a hormone treatment. However, the parasite's life-long presence in the bovine host provides a continuous daily expression of protein, which accumulates to a total production level over time, that is considerably higher then repeated doses of a sub-unit protein administration as commonly applied.

The constant systemic expression and presentation of the protein to the host for instance mimics the natural way hormones have their effect. Alternatively, a broad and long-lasting systemic immune-response can be reached by steering the way the protein is presented to the hosts' immune system, e.g. secreted, on the surface of the parasite, or internally in the parasite. The prolonged expression then provides an enduring immune-stimulation which surpasses any regular method of protein administration for instance by a formulation providing a depot function, or a slow-release implant.

As there is no mutual competition between *T. theileri* parasites in a bovine host, either recombinant or not, one advantageous use is the simultaneous use or administration of more than one recombinant *T. theileri* parasite according to the invention to a bovine host. This allows combinations of proteins to be encoded and presented, which can then interact to initiate or inhibit a certain biological function, for example an antigen and a chaperonin to assist in the proper processing and folding of the antigen. An other example is the separate expression of subunits from a heterodimeric protein consisting of e.g. an alpha and a beta subunit, which can then assemble into an active multi-meric molecule only in the bovine host, whereas for example the expression of the complete protein would be inefficient, or would be toxic to the recombinant *T. theileri* parasite.

Therefore, in a preferred embodiment of the sustained delivery vector according to the method and the use of the invention, the method or the use comprises the simultaneous use of two or more different recombinant *T. theileri* parasites according to the invention.

The "simultaneous" use for the invention can follow from simultaneous inoculation, but a second or further recombinant *T. theileri* can also be applied later than a previous one. This is because the parasites survive for a very long time, therefore the combined presence can also be applied (long) after an earlier inoculation. Consequently, a simultaneous use for the invention relates to a combined presence at some time in a bovine host's lifetime of more than one recombinant *T. theileri* parasites according to the invention.

A still further aspect of the invention relates to a composition for the sustained delivery of a protein to a bovine animal, comprising the recombinant *T. theileri* parasite according to the invention and a pharmaceutically acceptable carrier.

A "composition for the sustained delivery" for the invention, is a pharmaceutical composition suitable for the administration and inoculation of a recombinant *T. theileri* parasite according to the invention to a bovine animal. The manufacture of such a composition for the invention can be done by methods well known in the art, and comprises the admixing of a recombinant *T. theileri* parasite according to the invention, with a pharmaceutically acceptable carrier.

The composition is advantageously used for the expression and the delivery of a protein to a bovine host as described.

Therefore, in a further aspect the invention relates to a method for the preparation of a sustained delivery composition for bovine animals, comprising the admixing of the recombinant *T. theileri* parasite according to the invention, and a pharmaceutically acceptable carrier.

A "pharmaceutically acceptable carrier" is intended to aid in the effective administration of a compound, without causing (severe) adverse effects to the health of the animal to which it is administered. A pharmaceutically acceptable carrier can for instance be sterile water or a sterile physiological salt solution. In a more complex form the carrier can e.g. be a buffer, which can comprise further additives, such as stabilisers or conservatives. Details and examples are for instance described in well-known handbooks e.g.: such as: "Remington: the science and practice of pharmacy" (2000, Lippincot, USA, ISBN: 683306472), and: "Veterinary vaccinology" (P. Pastoret et al. ed., 1997, Elsevier, Amsterdam, ISBN 0444819681).

The use of the recombinant *T. theileri* parasite according to the invention as a sustained delivery vector in a bovine host animal, allows the expression and the delivery of a wide variety of proteins (and fragments thereof) to the bovine host. The inventors were the first to implement this into an advantageous medical use, by inducing a veterinary medical effect in a bovine host.

Consequently, in a further aspect the invention relates to the recombinant *T. theileri* parasite according to the invention for use as a medicament for bovine animals.

For the invention, a "medicament" is substance that is useful in the cure, treatment, amelioration, or prevention of a disease, or of the consequences of such a disease. Equally, a medicament can prevent or reduce the spread of a pathogen through a population or to the environment.

Several embodiments of this aspect have already been described above regarding the enhancement of the bovine's health and/or its production parameters by the sustained delivery.

A preferred embodiment of the use as a medicament according to the invention, is the use as a vaccine for bovine animals.

The advantageous effect is that when a bovine animal was vaccinated by the expression and delivery of a protein by a recombinant *T. theileri* parasite according to the invention, this lead to a safe and efficacious immune protection.

Therefore in a further aspect the invention relates to the recombinant *T. theileri* parasite according to the invention for use as a vaccine for bovine animals.

Also, in a further aspect the invention relates to the use of the recombinant *T. theileri* parasite according to the invention for the manufacture of a vaccine for bovine animals.

And in still a further aspect, the invention relates to a vaccine comprising the recombinant *T. theileri* parasite according to the invention and a pharmaceutically acceptable carrier.

The vaccine, and the use as a vaccine according to the invention provide the host's immune system with a sustained expression and presentation of protein, which provides constant stimulation of the immune system and generation of memory cells. This keeps the immune-surveillance to the expressed protein at high alert level, and provides a life long immunity to a bovine animal.

Further advantageous effects of the expression and delivery according to the invention are that the post-translational processing of the protein provided by the recombinant *T. theileri* in a bovine host is more natural than that protein expressed from an in vitro expression system such as by *E. coli* or by baculovirus and insect cells.

The invention is especially advantageous for generating and keeping up an immune surveillance against 'hidden antigens' of endo- and ecto-parasites. These are antigens from internal organs of a parasite, such as from the gut of a nematode, a fly or a tick, that are not commonly 'seen' by the bovine immune system. However when antibodies against such hidden antigens are present in the blood of a bovine host, then the parasite ingests them whenever it feeds on the bovine's blood.

Bovine pathogens from which antigens can be expressed and delivered by the recombinant *T. theileri* parasites according to the invention are for example:
  viruses: bovine viral diarrhoea virus (BVDV), Rift valley fever virus, bovine herpes virus, blue tongue virus, Rabies virus, foot and mouth disease virus, bovine respiratory syncitial virus (BRSV), epizootic hemorrhagic disease virus, parainfluenza type 3 virus, bovine paramyxovirus;
  bacteria: *Mannheimia, Pasteurella, Clostridia, Escherichia, Staphylococcus, Mannheimia, Mycobacterium, Brucella, Anaplasma, Streptococcus, Mycoplasma, Enterobacter, Klebsiella, Citrobacter, Salmonella* and *Streptococcus;*
  parasites: endoparasites such as: *Ostertagia, Haemonchus, Dictyocaulus, Cryptosporidium, Theileria, Babesia, Neospora,* and *Trypanosoma*. But also ectoparasites such as: tabanid flies (*Hybomitra, Haematopota,* and *Tabanus*) and ticks (e.g. *Boophilus, Dermacentor, Ixodes, Rhipicephalus,* and *Amblyomma*);
  fungi, yeasts; and
  the relevant pathogens of complex diseases e.g. "shipping fever" (bovine respiratory disease complex).

Preferred heterologous proteins for expression and delivery in the recombinant *T. theileri* parasite according to invention are: BVDV E2, Rabies G, BRSV F, *Mannheimia haemolytica* leukotoxin, *Ostertagia ostertagi* Asp 1 or 2, *Cryptosporidium parvum* cp15, gp40, or gp900, *Dictyocaulus viviparus* ACE, *Boophilus* (*Rhipicephalus*) microplus Bm86, *Ixodes* spec. Subolisin, *Babesia divergens* Bd37, and the human Apolipoprotein L1 (also known as trypanosome lytic factor) for use as an antimicrobial protein against *T. brucei*.

All these antigens are well known in the art, and nucleotide sequences of their encoding genes are known and available, for example from the scientific literature and from Genbank.

The vaccine according to the invention can be manufactured by methods as described herein, which are then readily applicable to a person skilled in the art. For example, the recombinant *T. theileri* according to the invention is constructed by transfection and recombination and the desired recombinant *T. theileri* is selected as described herein. Next the recombinant *T. theileri* is cultured in an in vitro system.

The bloodstream form of *T. theileri* can be amplified in an in vitro cell-culture set-up as described herein. Prior art describes the requirement for the addition of a feeder cell-layer or blood or blood-coagulant (Splitter & Soulsby, 1967, Exp. Parasitol. vol. 21, p. 137-148). The inventors have however developed a convenient and continuous cell culture system wherein no feeder cell-layer or blood(-coagulant) was needed.

Therefore, in a further aspect the invention relates to a method of culturing *T. theileri* in vitro, wherein a part of the medium used for said culture is a culture medium that had been conditioned by the culture of eukaryotic cells.

The eukaryotic cells for conditioning are preferably bovine cells, more preferably bovine epithelial cells, bovine kidney cells, and MDBK cells (in that order of preference).

Preferably, the part of conditioned medium is between 10 and 90% of the final *T. theileri* cell-culture medium, more preferably 50%.

This method of culturing according to the invention overcomes the unfavourable interference of feeder cells with an efficient monitoring and isolation of (recombinant) *T. theileri*. In particular, the feeder cell-layer will not function properly when a drug-selection mechanism is applied for the selection of recombinant *T. theileri* after recombination, or the subsequent amplification of a recombinant *T. theileri*. Instead, by the use of 50% v/v of a conditioned medium, a feeder cell-layer was no longer required, while excellent growth of the (recombinant) *T. theileri* was observed, and selective drug-concentrations could conveniently be used in the culture medium when appropriate.

*T. theileri* parasite cell-cultures can be scaled up conveniently, in containers of various sizes, such as plates, flasks, roller bottles, or fermentors. Techniques and equipment for cell-culture technology at any scale is well known and readily available from commercial suppliers.

Cell-densities of (recombinant) *T. theileri* up to $1 \times 10^6$/ml were routinely obtained. To maintain optimal viability, cultures were split when $5 \times 10^5$/ml parasites were reached.

*T. theileri* parasites were stored in a glycerol based storage medium at −80° C. or in liquid nitrogen. Vaccine was prepared by taking up the desired number of recombinant *T. theileri* parasites into an appropriate physiological buffer, and administering these to a bovine host by an appropriate route.

Titration and counting of (recombinant) *T. theileri* parasites can conveniently be done using a counting chamber or automatic cell-counting device.

Using the *T. theileri* culture medium as described, there was no need for adaptation to in vitro culture, e.g. by applying a number of passages, before newly obtained *T. theileri* parasites, e.g. freshly (re-)isolated from a bovine host, could be used in transfections or assays.

A vaccine for the invention, is prepared from live recombinant *T. theileri* parasites according to the invention. The parasites are produced industrially in smaller or larger volumes. Although production in host animals is possible, proliferation in in vitro cultures is preferred. After harvesting a suspension comprising the micro-organism, this suspension is formulated into a vaccine and the final product is packaged. After extensive testing for quality, quantity and sterility such vaccine products are released for sale.

General techniques and considerations that apply to vaccinology are well known in the art and are described for instance in governmental regulations and in handbooks such as: "Veterinary vaccinology" and: "Remington" (both supra).

Efficacy as a vaccine of the embodiments of the invention was demonstrated by the animal experiments described, in which cattle was inoculated with a recombinant *T. theileri* parasite according to the invention, which contained and expressed a vaccine-antigen from *Babesia divergens*, a bovine Piroplasmid (Apicomplexan) parasite (Delbecq et al., 2002, Parasitology, vol. 125, p. 305-312).

The Bd37 antigen was effectively expressed in the inoculated bovines, and generated an immune response which continuously increased up until the end of the experiment at 13 weeks after the 1$^{st}$ inoculation. This led to the production of highly specific antibodies, at a level that was previously demonstrated to be protective for *B. divergens*; this is corroborated by the fact that the antibodies produced were able to compete for the binding of immobilised Bd37 protein with a monoclonal antibody that is specific for Bd37, and that was shown to inhibit the infection of animals with *B. divergens* (Hadj-Kaddour et al., 2007, Parasitology vol. 134, p. 187-196).

It is within reach of a skilled person to further optimise the vaccine of the invention. Generally this involves the fine-tuning of the efficacy of the vaccine, so that it provides sufficient protection. This can be done by adapting the vaccine dose, or by using the vaccine in another form or formulation, or by adapting the other constituents of the vaccine (e.g. the stabiliser or the adjuvant), or by application via a different route. The safety of a vaccine according to the invention is not expected to be an issue, as the *T. theileri* parasite itself does not generate any vaccination response, and can be applied without an adjuvant. However a vaccination reaction could result from other constituents of the vaccine composition.

The vaccine may additionally comprise other compounds, such as an adjuvant, an additional antigen, a cytokine, etc.

The vaccine according to the invention can be used both for prophylactic and for therapeutic treatment, and so interferes either with the establishment and/or with the progression of an infection or its clinical symptoms of disease.

The term "vaccine" implies the presence of an immunologically effective amount of the recombinant *T. theileri* parasite according to the invention, and the presence of a pharmaceutically acceptable carrier.

What constitutes an "immunologically effective amount" for the vaccine according to the invention is dependent on the desired effect and on the specific characteristics of the recombinant *T. theileri* parasite that is being used. Determination of the effective amount is well within the skills of the routine practitioner, for instance by monitoring the immunological response following vaccination, or after a challenge infection, e.g. by monitoring the targets' clinical signs of disease, serological parameters, or by re-isolation of the pathogen, and comparing these to responses seen in unvaccinated animals.

In general a vaccine induces an immune response that aids in preventing, ameliorating, reducing sensitivity for, or treatment of a disease or disorder resulting from infection with a micro-organism. The protection is achieved as a result of administering (a composition containing) one ore more antigens derived from that micro-organism, such as an attenuated or killed micro-organism and/or a subunit thereof. This will cause the target animal to show a reduction in the number, or the intensity of clinical signs caused by the micro-organism. This may be the result of a reduced colonization or of a reduced infection rate by the micro-organism, leading to a reduction in the number or the severity of lesions and effects that are caused by the micro-organism or by the target's response thereto.

The exact amount of recombinant *T. theileri* parasites according to the invention in a vaccine dose is not as critical as it would be for a classical subunit type vaccine, because the parasite will replicate itself and thus multiply in the host up to a level of parasitaemia that is biologically sustainable. The vaccine dose only needs to be sufficient to generate a productive infection. A higher inoculum dose shortens the time it takes to reach the optimal parasitaemia in the host, but this is only a gain of time of a few days. Even higher doses are not effective in that the parasitaemia that establishes cannot be higher than the natural optimum, in addition such a very high inoculum dose is not attractive for economic reasons.

A preferred inoculum dose is therefore between $1 \times 10^2$ and $1 \times 10^8$ live parasites per animal-dose, more preferably between $1 \times 10^3$ and $1 \times 10^7$/dose, even more preferably between $1 \times 10^4$ and $1 \times 10^6$/dose. Live *T. theileri* parasites can easily be distinguished from dead or dying parasites by light microscopy, as live parasites are actively swimming in the upper layers of the culture medium, whereas sick or dying cells tend to slow down, and begin to clump prior to sinking to the bottom of the culture.

The dosing scheme for applying the vaccine according to the invention to a target organism can be in single or multiple doses, which may be given at the same time or sequentially, in a manner compatible with the formulation of the vaccine, and in such an amount as will be immunologically effective.

The vaccine according to the invention is advantageously used as a 'marker vaccine'. A marker vaccine is known as a vaccine that allows the discrimination between vaccinated and field-infected subjects. This is determined e.g. by detection of a vaccine-characteristic antibody panel, that is different from the antibody panel induced by infection with the wild type infectious agent. Such difference is for instance obtained when an immunogenic protein present in or on a wild type micro-organism is not present in the vaccine. This can conveniently be detected by a serological assay such as an ELISA or immuno-fluorescence assay.

Therefore, in a preferred embodiment, the vaccine according to the invention is a marker vaccine.

The composition for sustained delivery, or the vaccine, both according to the invention, may contain one or more components that aid the viability and quality of the recombinant *T. theileri* parasite according to the invention, thereby promoting the productive replication and establishment as a commensal infection in the bovine host.

In a preferred embodiment, the compounds used for the production of the vaccine according to the invention are serum free (without animal serum); protein free (without animal protein, but may contain other animal derived components), animal compound free (ACF; not containing any component derived from an animal); or even 'chemically defined', in that order of preference.

In a further preferred embodiment the vaccine according to the invention additionally comprises a stabiliser.

Stabilisers are compounds that stabilise the quantity and the quality of the recombinant parasite according to the invention during storage, handling, and inoculation, such as by injection or ingestion. Generally these are large molecules of high molecular weight, such as lipids, carbohydrates, or proteins; for instance milk-powder, gelatine, serum albumin, sorbitol, trehalose, spermidine, Dextrane or polyvinyl pyrrolidone.

Also preservatives may be added, such as thimerosal, merthiolate, phenolic compounds, or gentamicin.

It goes without saying that admixing other compounds, such as carriers, diluents, emulsions, and the like to vaccines according to the invention are also within the scope of the invention. Such additives are described in well-known handbooks such as: "Remington", and "Veterinary Vaccinology" (both supra).

In addition, the composition or the vaccine, both according to the invention, can advantageously be combined with a pharmaceutical component such as an antibiotic, a hormone, or an anti-inflammatory drug. Evidently, this combination must not interfere in a negative sense with the efficient establishment of a commensal infection by the recombinant T. theileri parasite according to the invention in a bovine host animal, or the sustained expression and delivery of a protein.

It is highly efficient to formulate the vaccine according to the invention as a combination-vaccine, as in this way multiple immunologic agents can be administered at once, providing reduction of time- and labour costs, as well as reduction of discomfort to the vaccinated target animals. A combination vaccine comprises in addition to the vaccine according to the invention, another antigenic compound. In general this can be any live or killed micro-organisms or subunit product.

Alternatively, the vaccine according to the invention, may itself be added to a vaccine.

Therefore, in a further preferred embodiment, the vaccine according to the invention is characterised in that the vaccine comprises one or more additional immunoactive component(s).

In a more preferred embodiment the vaccine according to the invention is a combination vaccine, comprising at least one additional micro-organism of bovine animals. The additional immunoactive component(s) may be an antigen, an immune enhancing substance, and/or a vaccine, again with the proviso that there is no significant interference with the establishment of a commensal infection.

The preferred bovine target animals for the application of the composition for sustained delivery, or the vaccine, both according to the invention, is cattle, more preferably: beef cattle or milk cattle.

The vaccine according to the invention may effectively serve as a priming vaccination, which can later be followed and amplified by a booster vaccination, for instance with a classical inactivated-adjuvanted vaccine.

The protocol for the administration of the vaccine according to the invention ideally is integrated into existing vaccination schedules of other vaccines.

An advantageous method of inoculation is by a method of mass application such as by combining with the feed or drinking water; this will require the use of an appropriate buffer or stabiliser.

Therefore, in a further aspect, the invention relates to a method for the vaccination of a bovine animal, comprising the step of inoculating said bovine animal with a vaccine according to the invention.

The age, weight, sex, immunological status, and other parameters of the bovines to be vaccinated are not critical, although it is evidently favourable to vaccinate healthy targets, and to vaccinate as early as possible to prevent any field infection. As an infection of T. theileri can be established already at very young age, therefore the vaccine according to the invention can be applied from birth onwards, preferably within the first 2 weeks after birth; any colostral antibodies from the mother will not significantly interfere with the establishment of an infection in the calf.

The considerations regarding the composition and use of a vaccine according to the invention, apply mutatis mutandis also to the composition according to the invention.

The composition for sustained delivery, and the vaccine, both according to the invention, in principle will only need to be applied to a bovine target once in its lifetime. This is because once the recombinant T. theileri parasite had established itself as a commensal infection, no booster was necessary or effective. However, other circumstances may cause the death or a reduced replication of the recombinant T. theileri parasite in its bovine host, for example the treatment of the bovine with antiparasitic drugs to overcome a pathogenic parasite infection. In that case a re-application of the composition or vaccine according to the invention is necessary to re-establish the sustained expression and delivery of protein according to the invention. An efficient PCR assay such as described herein below can conveniently be used to confirm if any rec. T. theileri is still present in the bovine host.

The composition for sustained delivery, or the vaccine, both according to the invention, when applied in liquid form and administered to an individual animal, can be administered in a volume of between 0.1 and 10 ml per animal, preferably between 0.25-5 ml, 0.5-3 ml, or 1-2 ml per animal, in that order of preference. The determination, and the optimisation of the dosage level of other application forms or -routes is well within the capability of the skilled artisan.

A vaccine according to the invention may take any form that is suitable for administration to bovine animals, and that matches the desired route of application and the desired effect.

The preparation of a vaccine according to the invention is carried out by means well known to the skilled person. Preferably the vaccine according to the invention is formulated in a form suitable for injection, such as a suspension, solution, dispersion, or emulsion. Commonly such vaccines are prepared in a sterile way.

Therefore, in a further aspect, the invention relates to a method for the preparation of the vaccine, or the composition, both according to the invention, the method comprising the admixing of the recombinant T. theileri parasite according to the invention and a pharmaceutically acceptable carrier.

Some of the embodiments of the use of the recombinant T. theileri parasite according to the invention, or the effects of such a use, may be considered—in specific jurisdictions—to be non-curative, or may not be considered to be of a therapeutic nature, or not a treatment as such. Which uses would be within that category differs for the various patenting authorities and systems of national law. For those situations, the invention relates to a non-curative treatment.

Therefore, the invention in a further aspect relates to the use of the recombinant *T. theileri* parasite according to the invention for a non-curative treatment of bovine animals.

Such non-therapeutic treatments of bovine animals are typically directed at stimulating or improving production related output parameters, such as the quantity and/or the quality of meat, milk, or off-spring.

Therefore, in a preferred embodiment, a non-curative treatment according to the invention relates to a treatment selected from the group consisting of: growth promotion, improvement of feed-conversion, manipulation of fertility, improvement of milk quantity or milk quality, and improvement of meat quantity or meat quality.

To obtain a recombinant *T. theileri* parasite according to the invention, the inventors could not straightforwardly apply the techniques of the prior art. This describes recombination of Trypanosomatid parasites, for instance in: WO 98/11245, WO 00/32796, WO 01/32896, WO 2004/044184, or WO 2004/054969, and: Blundell et al., 1996, Mol. & Biochem. Parasitol. vol. 76, p. 215-229), and E1-Sayed and Tielens & van Hellemond (both supra).

These methods were not directly applicable in the case of *T. theileri* amongst others because of differences in lifecycle and biological behaviour, but also because of significant differences in genomic sequences. All these variations required specialised modifications and adaptations.

For example, in spite of several attempts, the inventors have never succeeded in obtaining recombinant *T. theileri* parasites from transient transfections, and episomal expression of a heterologous nucleic acid, whereas episomal expression is well established for *T. cruzi* (Martinez-Calvillo et al., 1997, Gene, vol. 199, p. 71-76). Similarly, the inventors were surprised to find that exchange of the flanking signals for RNA processing (in the IR sequences) only had little effect on the level of RNA transcription, or translation. For example, recombinant *T. theileri* expressing both Blasticidin resistance and a CAT gene, showed essentially the same production of CAT-activity (as measured by Elisa) irrespective of the order of the two genes, or the choice of flanking intergenic regions, when this was varied between the IR from actin, PFR or Tubulin; see FIG. 1, constructs of number 2. This was unexpected because in *T. brucei* such changes caused major differences to mRNA stability and hence the level of expression (Irmer & Clayton, 2001, Nucl. Acids Res. vol. 29, p. 4707-4715).

Without wishing to be bound to theory, the inventors concluded that *T. theileri* takes an intermediary evolutionary position, in-between the intracellular *T. cruzi* and the extra cellular *T. brucei*. This, in combination with its characteristics as a non-pathogenic parasite, and its commensal lifestyle, exclusively in bovines, makes that *T. theileri* has unique properties that necessitated dedicated methods and materials for its handling and manipulation.

The inventors have therefore developed and optimised the many tools and methods that were required to arrive at an efficient protocol for the transfection and use of recombinant *T. theileri*. These comprise: the conditions for long-term in vitro culturing of *T. theileri* parasites; PCR primers for cloning, mutation, and for detection and verification of recombination; a PCR for detection of the parasite in an infected bovine; a method of transfection with a heterologous nucleic acid; a method of homologous recombination, which includes the selection of appropriate overlapping sequences, and the selection of integration regions for stable insertion into the genome; the construction of the integration cassettes to be inserted into the genome; the selection and use of the intergenic regions for providing the signals for RNA processing; a method of selection of recombinant *T. theileri* parasites; etcetera. All these are described herein in detail, and can now be applied, and expanded upon by a person skilled in the art.

Therefore, in a further aspect the invention relates to a method for the generation of a recombinant *T. theileri* parasite according to, and for use in, the various embodiments of the invention.

In a preferred embodiment the invention relates to a method for the preparation of the recombinant *T. theileri* parasite according to the invention, comprising the mutation of the genomic DNA of a *T. theileri* parasite.

Such a method for the preparation of a recombinant *T. theileri* parasite (also: a method of recombination of a *T. theileri* parasite) allows the generation of a recombinant *T. theileri* providing the advantageous uses as described herein.

Methods and materials for the mutation of the genomic DNA of a *T. theileri* parasite are described below, and detailed examples are enclosed.

In a more preferred embodiment of the method for the preparation of the recombinant *T. theileri* parasite according to the invention, the mutation comprises the addition of a nucleic acid, in the form of the insertion into the genomic DNA of a *T. theileri* parasite of a heterologous nucleic acid sequence that is capable of encoding at least one heterologous protein.

By this type of recombination the method generates a recombinant *T. theileri* that is capable of expressing a heterologous gene according to the invention, for example allowing the use of the recombinant *T. theileri* generated, as a sustained delivery vehicle for bovine animals as described.

In an even more preferred embodiment of the method for the preparation of the recombinant *T. theileri* parasite according to the invention, the method comprises the steps of:
a. transfection of a *T. theileri* parasite with a DNA molecule comprising a heterologous nucleic acid sequence capable of encoding at least one heterologous protein,
b. allowing homologous recombination between said DNA molecule and the genomic DNA of said *T. theileri* parasite, and
c. selection of the desired recombinant *T. theileri* parasite.

This method conveniently provides recombinant *T. theileri* parasites according to the invention. Subsequently, these recombinant *T. theileri* parasites were tested, amplified and used in vitro and in vivo. Details and examples are described below.

The "transfection" of a micro-organism is a well known technique in molecular biology, and comprises the introduction of a nucleic acid into said micro-organism. For the invention this comprises the transfection of a DNA molecule into the *T. theileri* parasite, which DNA molecule comprises the mutation that is to be introduced into the parasite's genome.

Several transfection protocols are known, however these require optimisation on a case-by-case basis. With the details and examples provided herein a skilled person can optimise and vary on the method described.

For the invention, transfection of *T. theileri* parasites with a DNA molecule was conveniently done by electroporation, but other methods are also conceivable, such as chemical transfection using calcium-phosphate and glycerol-shock, or by using cationic liposomes such as Lipofectin® reagent.

Transfection efficiencies of 1:10^5 to 1:10^6 were reached, and these will likely be further optimised in future. The use of a selective criterion such as resistance to a selective drug, can advantageously be used to identify and select for those parasites that have become stably transfected.

The "DNA molecule" for use in the method for the preparation of the recombinant *T. theileri* parasite according to the invention, can in principle be any DNA molecule that provides an efficient integration into the *T. theileri* genome, of the desired mutation, at the intended genomic location. Such a DNA molecule is termed an 'integration cassette'.

In the integration cassette the various parameters for making *T. theileri* recombinants are embedded, with the most important ones being: the selection of the target region of the *T. theileri* genome to integrate into; the mutation to be introduced; and regulatory signals (in case the mutation introduces a DNA sequence that is to be expressed as a protein).

An integration cassette is preferably constructed in, and derived from, a plasmid backbone that aides in the assembly and the amplification of the DNA molecule to be transfected. The combined construct of integration cassette and plasmid backbone is termed a 'transfervector'. Details and examples of *T. theileri* transfervectors for the invention are provided herein.

The "homologous recombination" technique is well known in the art, and is generally used to generate recombinant micro-organisms. Although the exact molecular processes are not known, key to the process is the lining-up and base pairing of homologous regions of nucleic acid, which can then 'cross-over' and so exchange genetic information. For the invention this means that target regions of the *T. theileri* genome where a mutation is to be introduced, are subcloned into an integration cassette and used to direct the integration of the desired mutation to the intended locus on the parasite's genome.

The combined use of an integration cassette, derived from a *T. theileri* transfervector, a method of transfection of that integration cassette into a *T. theileri* parasite, and the homologous recombination technique, allowed the directed mutation of *T. theileri* parasites, which generated the recombinant *T. theileri* parasite according to the invention.

Therefore, in a further aspect the invention relates to the use of a *T. theileri* transfervector for the preparation of a recombinant *T. theileri* parasite according to the invention.

A "*T. theileri* transfervector" for the invention comprises both an integration cassette and a plasmid backbone.

The plasmid backbone, can in principle be any convenient (commercial) cloning plasmid which allows the required manipulations. Examples of suitable plasmids are plasmids of the pBR, pUC, and pGEM series, all available from commercial suppliers. Details are provided of use of the pGEM T Easy® (Promega) plasmid as backbone.

The integration cassettes for use in the invention are described below.

It is preferred not to transfect the whole transfervector into the *T. theileri* parasite, and integrate that into the parasite genome, but only the integration cassette part of the transfervector. For that purpose the transfervector was advantageously constructed to contain unique restriction enzyme sites at beginning and end of the integration cassette, for its easy excision from the vector.

Details and examples of the various cloning and verification experiments involved in the generation of a *T. theileri* transfervector are provided herein, for example: restriction enzyme digestion, gel-electrophoresis, PCR, DNA-ligation, etc. For the more general aspects of these techniques, in principle standard protocols and commercial kits can be employed, these are for instance described in handbooks such as: Sambrook & Russell: "Molecular cloning: a laboratory manual" (2001, CSHL press, ISBN: 0879695773), and: Dieffenbach & Dveksler: "PCR primers: a laboratory manual" (1995, CSHL press, ISBN 0879694473).

A *T. theileri* integration cassette for the invention preferably comprises from outside towards the centre, the following elements:
- at both ends: unique restriction enzyme (RE) recognition sites
- inward from the RE sites, near both ends: flanking target regions from the *T. theileri* genome for homologous recombination,
- internal to the target regions, and flanking the central portion: signal sequences for RNA processing, in case the expression of a heterologous nucleic acid sequence is intended, and
- centrally: the nucleic acid sequence comprising the mutation that is to be introduced.

A graphic representation of examples of integration cassettes for the invention is presented in FIG. 1, and graphs of examples of transfervectors comprising such integration cassettes are given in FIGS. 3-14.

The integration cassette thus comprises at its termini sections of the *T. theileri* genome derived from the target region where the homologous recombination is to occur. The length of these recombination regions is not fixed, but when these are too small, for example smaller than 100 nucleotides each, specific recombination at the desired locus cannot be ensured. Therefore, in a preferred embodiment the recombination regions are each at least 100, 200, 300, 400 or at least 500 nucleotides in length, in that order of preference. Conversely, target regions that are excessively long should also be avoided, as that may introduce instability in the integration cassette itself, for instance from repeated sequences. Therefore, the recombination regions are each preferably not more than 3000 nucleotides long, more preferably not more than 2500, 2000, 1500, or 1000 nucleotides, in that order of preference.

The two flanking sections are of about the same size. Sequence-details are provided below.

The target region on the *T. theileri* genome for the insertion of the mutation of the invention, in principle can be any region of the *T. theileri* genome, provided a viable recombinant parasite can be obtained, and effective expression occurs in the bovine host animal. Therefore the target recombination region is on a section of the parasite's genome that is expressed in the bovine host, and which does not disturb genes that are essential, haplo-insufficient, or critical regulatory areas. Also, genome regions that are unsuitable are the centromers; heterochromatic regions; or regions producing an antisense tRNA transcript.

In addition, because it is expected that *T. theileri* applies a polycistronic replication mode, the recombination must not cause a blockade to the transcription of downstream genes.

Therefore, in a preferred embodiment the target region of the *T. theileri* genome for recombination is selected such that the resulting recombinant *T. theileri* parasite retains its wild-type viability, and allows effective expression of an inserted heterologous gene in a bovine host. Regions of the genome that are highly expressed are more preferred, for example: housekeeping gene regions such as tubulin, actin, and the paraflagellar rod (PFR) genes.

In addition, genes that are haplo-sufficient or are present in multiple copies, such as in tandem gene arrays are more preferred as insertion targets, because in this case a disruption of one gene was found to be without effect on the recombinant parasite. Examples are the gene-clusters for the genes for Tubulin, actin, PFR, calmodulin, histones, and major surface proteins; such genes are mainly driven by the type II RNA polymerase.

Insertions in genomic locations that exist in multiple copies may produce recombinants that present the same mutation, or express the same inserted heterologous nucleic acid, but differ from each other in the exact location of the integration in the gene array. However, such inter-array positional differences are not expected to have effect on expression levels; if differences are observed, the highest expressing recombinants can conveniently be selected.

The different sorts of genes on the genome of *T. theileri* are transcribed by different RNA polymerases. Therefore, in a further preferred embodiment, those regions from *T. theileri* are selected for harbouring and expression of a heterologous gene insert, that are transcribed by RNA polymerase I, as these were found to be more highly expressed than genome regions transcribed by RNA polymerase II.

Examples of RNA pol I transcribed regions of the genome of *T. theileri* are most of the ribosomal RNA (rRNA) genes.

Details are provided of insertions made in the Tubulin gene locus, which is transcribed by RNA pol II, and in the 18S small subunit (SSU) rRNA gene locus, which is transcribed by RNA pol I.

A further aspect of the selection of the insertion region on the genome of *T. theileri*, is the placing of the mutation in respect to transcribed and non-transcribed sections: when the mutation is a substitution or an addition, this can be placed in an ORF of *T. theileri*, or in an intergenic region (IR) between ORF's. When the mutation is a deletion, this can remove all or part of an ORF and/or an IR. Also combinations can be made, for instance when the insertion of a heterologous nucleic acid deletes both (a part of) an ORF and an IR of the *T. theileri* genome. In principle all these conformations can be made and used by a skilled person with the information provided herein, and adaptations and optimisations can conveniently be made. Details are provided below of one insertion of a heterologous nucleic acid sequence in the coding region of an ORF, and of one that is replacing an ORF; the insertion into the 18S SSU rRNA gene locus is an insertion into an ORF, and the insertion in the Tubulin gene locus is an insertion in the intergenic areas before and after a beta-Tubulin gene, thereby replacing that gene by a heterologous one.

The insertion cassette must comprise a further element, in case the mutation of the *T. theileri* genome according to the invention comprises the insertion of a heterologous ORF or gene for expression by the parasite; in that case the integration cassette needs to comprise signalling sequences for RNA processing, which signals flank the nucleic acid sequence to be expressed. Consequently, such signals are situated in the integration cassette at the inside of the targeting regions for genome insertions, but on the outside of the central sequence carrying the mutation to be integrated, which in this case is a heterologous nucleic acid sequence capable of encoding a protein.

The signalling sequences for RNA processing that regulate the level and the timing of protein expression of a heterologous nucleic acid sequence in a live recombinant *T. theileri* parasite are comprised within the IR sequences on the parasite's genome. These signals for RNA-editing are e.g. the poly-Adenylation signal and the splice-leader acceptor site. This way *T. theileri* IR's were found to provide both a poly A function for the gene that is upstream of it, as well as a splice-leader acceptor site for the downstream gene.

In principle most IR's from the *T. theileri* genome can be used to provide RNA processing signals, provided they serve the intended use. Preferred are the IR regions from highly expressed genes as these will be optimal for high level expression of a heterologous protein.

Details are provided of the use of different IR's from *T. theileri*: the alpha-beta Tubulin IR, the beta-alpha Tubulin IR, the PFR IR, and the Actin IR.

NB: the "alpha-beta Tubulin IR" refers to the IR that is in between an alpha Tubulin gene and a beta Tubulin gene; the same applies mutatis mutandis for the "beta-alpha Tubulin IR".

The use of different IR signalling regions will produce RNA transcripts from the inserted heterologous nucleic acid that are of different lengths; this is because the length of the untranslated region prior to the polyA addition site varies in length between these IR sequences. As a result, this may lead to recombinant *T. theileri* parasites that express the same inserted heterologous nucleic acid to a different level, which conveniently allows the most optimally expressing recombinant to be selected.

Therefore in a further aspect the invention relates to the use of a *T. theileri* intergenic region sequence for the construction of a recombinant *T. theileri* parasite according to the invention.

Sequences of *T. theileri* IR's are presented herein, in SEQ ID NO's: 11-13 and 20-21. These IR sequences can advantageously be used in the methods and vectors according to the invention, either as targeting regions, or as flanking regions, wherein one IR sequence is attached at the 5' and one at the 3' end of a nucleic acid that is capable of encoding a protein; this way recombinant *T. theileri* parasites according to the invention can be generated. Both signals may be the same or different.

In a preferred embodiment, an IR for use in the invention is not the complete IR comprising all RNA processing signals, but is a *T. theileri* IR that provides a specific signal function; for example, only the poly A signal, or only the splice leader acceptor site. An example is provided herein for the *T. theileri* actin IR splice-leader acceptor signal (SEQ ID NO: 21) which was attached to the 5' end of a nucleic acid capable of encoding a protein.

The use of shortened IR sequences conveniently minimises the possibility of these sequences competing with the sequences used for genome-integration targeting. In addition this limits the size of the transfervector that is being used.

The central part of the integration cassette for use in the invention is the nucleotide sequence comprising the mutation that is to be introduced into a *T. theileri* parasite. The mutation can be anything from a simple point mutation, or an added restriction site, up to a complex integration cassette comprising multiple heterologous genes. Preferably the mutation is the insertion of a heterologous nucleic acid capable of encoding (one or more) heterologous protein(s). Details and examples of the construction and use of mutation sequences for the invention are provided herein.

It is within the scope of the invention to generate and use recombinant *T. theileri* parasites that comprise more than one mutation. Therefore, preferred integration cassettes for the invention comprise more than one heterologous nucleic acid capable of encoding a protein. For instance a tandem construct of a drug-resistance gene and one or more additional coding region(s). Each of these needs to be properly flanked by RNA processing signals from IR's, as well as be oriented in the direction of the read-through transcription.

Recombinant *T. theileri* parasites expressing more than one heterologous protein can be constructed to have the encoding nucleic acids in the same, or in different locations on the *T. theileri* genome. This provides flexibility in the recombinant manipulations, and allows the selection of the optimal genomic insertion region for each type of encoded protein.

Naturally, these manipulations should not significantly interfere with the viability of the recombinant *T. theileri* parasite, or the efficient in vivo display of the modified genotype.

To generate recombinant *T. theileri* parasites carrying multiple insertions in different genomic locations, the parasite is transfected with different integration cassettes according to the invention, that are aimed for integration in the different genomic locations selected. The transfections can be performed simultaneously, but are preferably done consecutively, to allow for the recovery of the transfected parasites and the individual selection of the stable transfection after each mutation.

As described before, the heterologous nucleic acid for expression by a recombinant *T. theileri* parasite in principle can encode any one of a variety of proteins, dependent on the desired effect that is to be imposed on the bovine host.

In a preferred embodiment, the inserted heterologous nucleic acid (also) encodes a protein that provides resistance to an anti-parasitic drug. Such a recombinant parasite allowed the convenient selection of those parasites that were stably transfected, upon culturing in a medium comprising the antiparasitic drug in selective concentration.

The resistance gene inserted, is preferably selected based on the natural sensitivity profile of the specific wildtype *T. theileri* parental isolate that is being used, to enhance the selective effect. For example, a *T. theileri* isolate that was found to be extremely sensitive for Blasticidin, was conveniently provided with a Blasticidin-resistance gene. The resulting recombinant parasite could survive and proliferate in medium containing 10 µg/ml Blasticidin, whereas unsuccessfully transfected parasites died off within a few days. Details and examples are provided of recombinant *T. theileri* parasites according to the invention that expressed a Blasticidin-resistance gene from the Tubulin IR, or from the 18S SSU rRNA gene.

Examples of other drug-resistances that may be used are for: Bleomycin (or Phleomycin), Blasticidin, Amphotericine, Puromycin, Neomycin, and/or Hygromycin.

Preferred recombinant *T. theileri* parasites according to the invention comprised in addition to the drug-resistance gene, a further heterologous nucleic acid, capable of encoding a protein other than for drug-resistance. This provides a further means to select stably transfected parasites, by testing for RNA or protein derived from this insert.

It is preferred to combine into one insertion cassette both the drug-resistance gene and the additional gene(s). This conformation advantageously provides a straight-forward insurance that next to the drug-resistance gene, also the other encoding sequence is present in the resistant recombinant *T. theileri* parasite, because the display of a drug-resistant genotype was found to be a reliant indicator for the stable integration of the other coding sequence also.

Even more preferred is the use of an integration cassette for expression of an additional gene, where the additional gene is present in more than one copy, for example an integration cassette comprising a drug-resistance gene, and two or more copies of an additional gene. Examples of such an embodiment are the 'tandem' constructs displayed in FIG. 1, constructs 5 and 6, and in FIGS. 9-11 and 13-14. Such constructs advantageously provided enhanced RNA transcription and protein expression levels of the additional gene, as compared to constructs comprising only a single additional gene insert.

In a further preferred embodiment, recombinant *T. theileri* parasites comprising more than one coding sequence other than drug-resistance, are constructed in a way that they comprise more than one insertion cassette, each comprising a drug-resistance gene (preferably different ones) and an additional gene (being the same or different), wherein each insertion cassette is integrated in a different genomic location.

This way multiply drug-resistant *T. theileri* parasites can be generated, and the display of each of the resistance phenotypes is also an indication for the stable insertion of the additional genes.

Details and examples are provided of recombinant *T. theileri* parasites expressing a number of genes, in combination with a drug-resistance gene, from different locations in the *T. theileri* genome.

Expressed genes were: marker genes such as enhanced green fluorescent protein (eGFP), and chloramphenicol acetyl-transferase (CAT); and antigen genes such as: acetylcholinesterase-1 from *Dictyocaulus viviparus* (bovine lungworm, a bovine nematode), and Bd37 from *Babesia divergens* (an apicomplexan Piroplasmid, causing cattle malaria). Sequence-details of these genes are known, for example: eGFP was derived from a pEGFP-C1 plasmid (Clontech laboratories); *E. coli* CAT was described from a pCATR reporter plasmid (Promega), and the Blasticidin resistance gene from *Aspergillus terreus* is described by Kimura et al., in Biochim. Biophys. Acta, 1994, vol. 1219, p. 653-659. Also the antigen genes are known: the secreted form of ACE-1, was from Genbank accession nr. AY546079, and Bd37 was from Genbank accession nr. AJ422214.

Detection of effective expression of the inserted genes (other than the drug resistance gene) was done in a variety of ways. Initially by detection of RNA transcription from recombinant *T. theileri* cultured in vitro, by Northern blotting. The in vitro detection of expression of protein was preferably done for example by immunological techniques such as ELISA or immune-fluorescence, as this incorporates an assessment of the immunological quality of the expressed protein.

Next to successful survival of drug-concentrations by recombinant *T. theileri* parasites (demonstrating stable transfection with the drug-resistance gene), also effective mRNA transcription and protein expression levels in vitro could be measured for other heterologous gene-expression. Details of exemplary embodiments are provided in the examples.

Ultimately, protein expression and -efficacy as a sustained delivery vehicle to a bovine host were tested in vivo, by detection of sero-conversion in cows inoculated with recombinant *T. theileri* parasites according to the invention. For example, calves with or without prior *T. theileri* infection were inoculated with a recombinant *T. theileri* according to the invention, and their seroconversion to an expressed antigenic protein was monitored over time. Survival of the recombinant *T. theileri* parasite over the full duration of the trial was established (both in the wild-type positive as in the -negative animals), and a gradual increase in seroresponse was detected; the level of the seroresponse that was reached had previously been shown to be protective against challenge. Details of an exemplary embodiment are provided in the examples.

In order to be able to detect wildtype and/or recombinant *T. theileri* parasites before and after inoculation in a target animal, sensitive PCR assays were developed that detected either wildtype- or inserted heterologous genes.

A nested PCR assay was developed to detect any *T. theileri*, using the specific *T. theileri* genomic sequence information obtained for the invention. One advantageous set-up allowed the detection of any *T. theileri* in cow's blood. The test was aimed at an alpha-beta Tubulin IR sequence (SEQ ID NO: 12). After optimising both the protocol for extraction of *T. theileri* genomic DNA from bovine blood, and the selection of primers, the optimised assay could detect infection levels as low as 10 *T. theileri* organisms per ml of bovine blood in all cases, and 5 organisms/ml in about half of the samples tested. As this is at the lower end of the naturally occurring infection levels (10-100 parasites/ml blood), this assay can conveniently be used to determine whether a bovine animal carries a *T. theileri* infection, either recombinant or not.

To detect recombinant *T. theileri* against a background of natural infection, a similar assay was developed for recombinant *T. theileri*. Such a test must be able to discriminate between recombinant and non-recombinant *T. theileri*, and can then serve to monitor the establishment and progression of an infection with a recombinant *T. theileri* parasite according to the invention. Also this will serve to confirm a recombinant *T. theileri* is still present in a formerly inoculated animal, or that revaccination is required.

For example a similar nested PCR assay have been developed that targets the Bd37 antigen gene inserted in some of the recombinant *T. theileri* used. Details are provided in the examples. Because the recombinants contained less copies of the Bd37 gene then from the alpha-beta tubulin IR region, the Bd37 PCR usually gave a less strong signal.

In further preferred embodiments, the integration cassette can be made to contain signals for regulateable expression, such as via a conditionally active operator, that can be used to turn expression on or off when appropriate. An example is the Tetracycline operon-repressor system, as described in WO 2004/026903.

Another further modification to the integration cassette can be the incorporation of protein trafficking signals, to allow control over the trafficking of the expressed protein. For example, an N-terminal signal sequence, or a C-terminal transmembrane sequence can be attached—separately or combined—to the nucleic acid capable of encoding a protein. As described, the resulting fusion protein is thus engineered to either remain intracellular, to be bound on the cell-surface, or to be excreted outside of the parasite cell. See FIG. 1, constructs numbered 3-6.

In principle a wide variety of suitable N- or C-terminal signals can be used; for example the N-terminal signal sequence from the *T. brucei* Binding protein (BiPN-term) and the GPI anchor from a *T. brucei* VSG gene (both: Bangs et al., 1996, Journal of Biol. Chem., vol. 271, p. 18387-18393).

Figure 11:
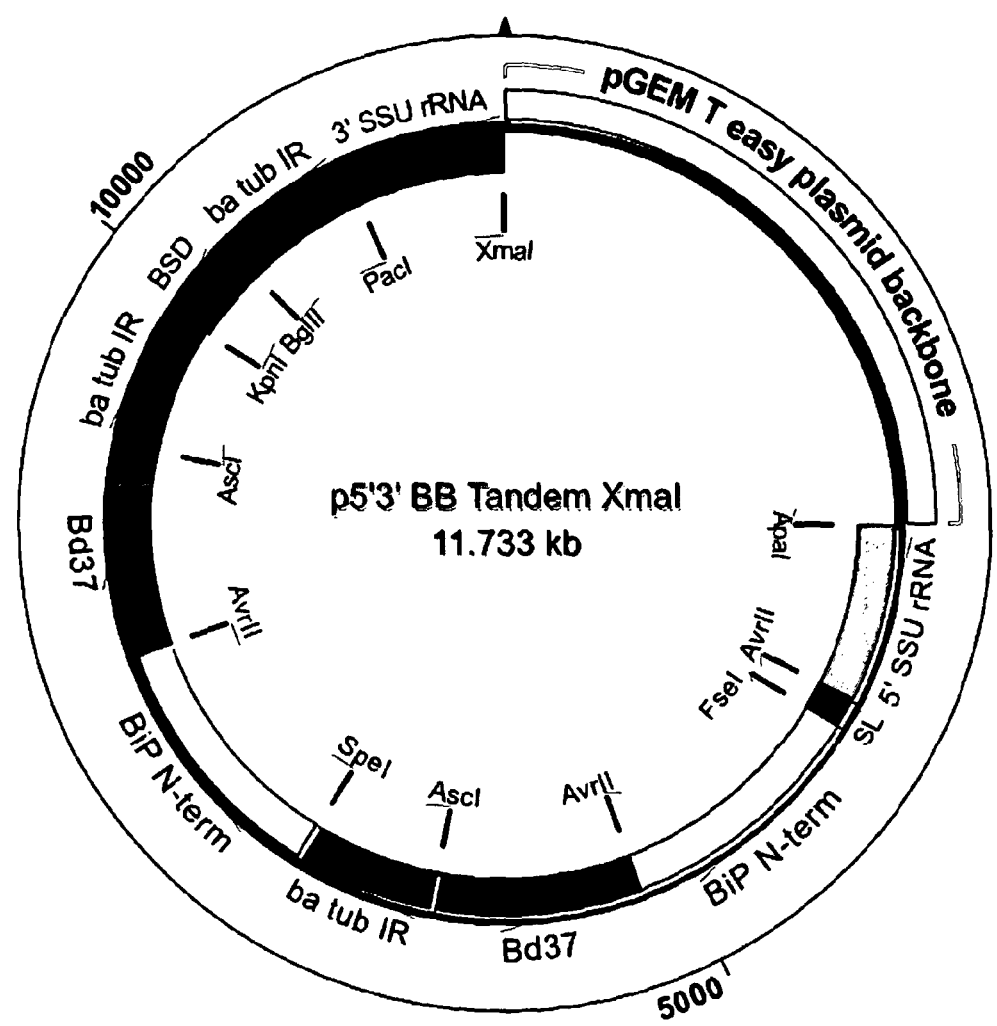
Figure 12:
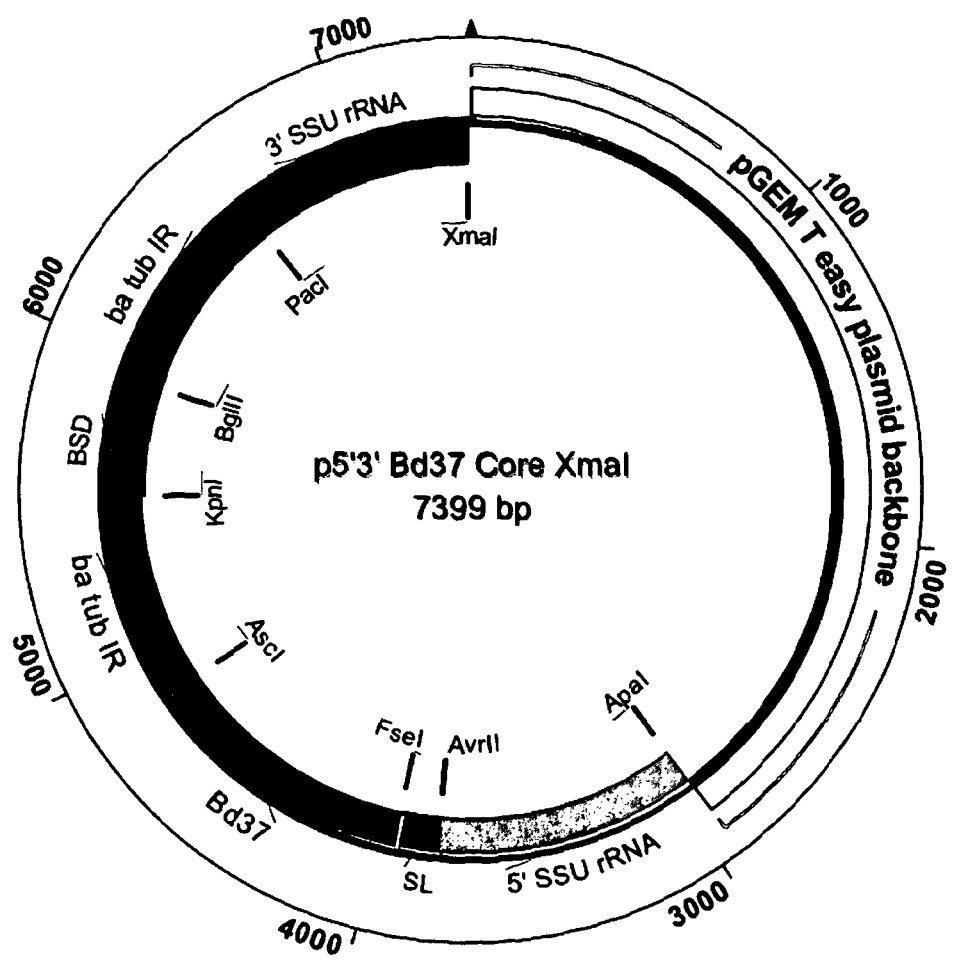
Figure 13:
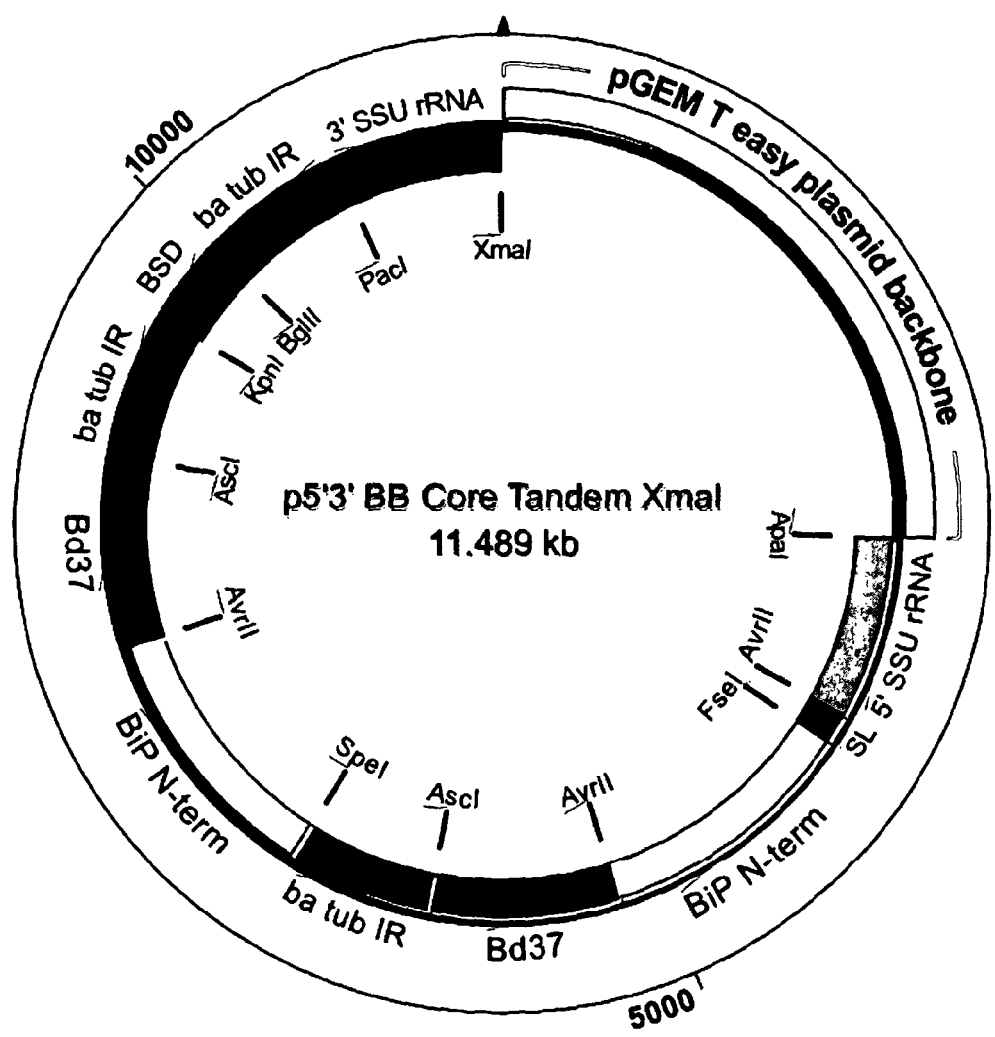
Figure 14:
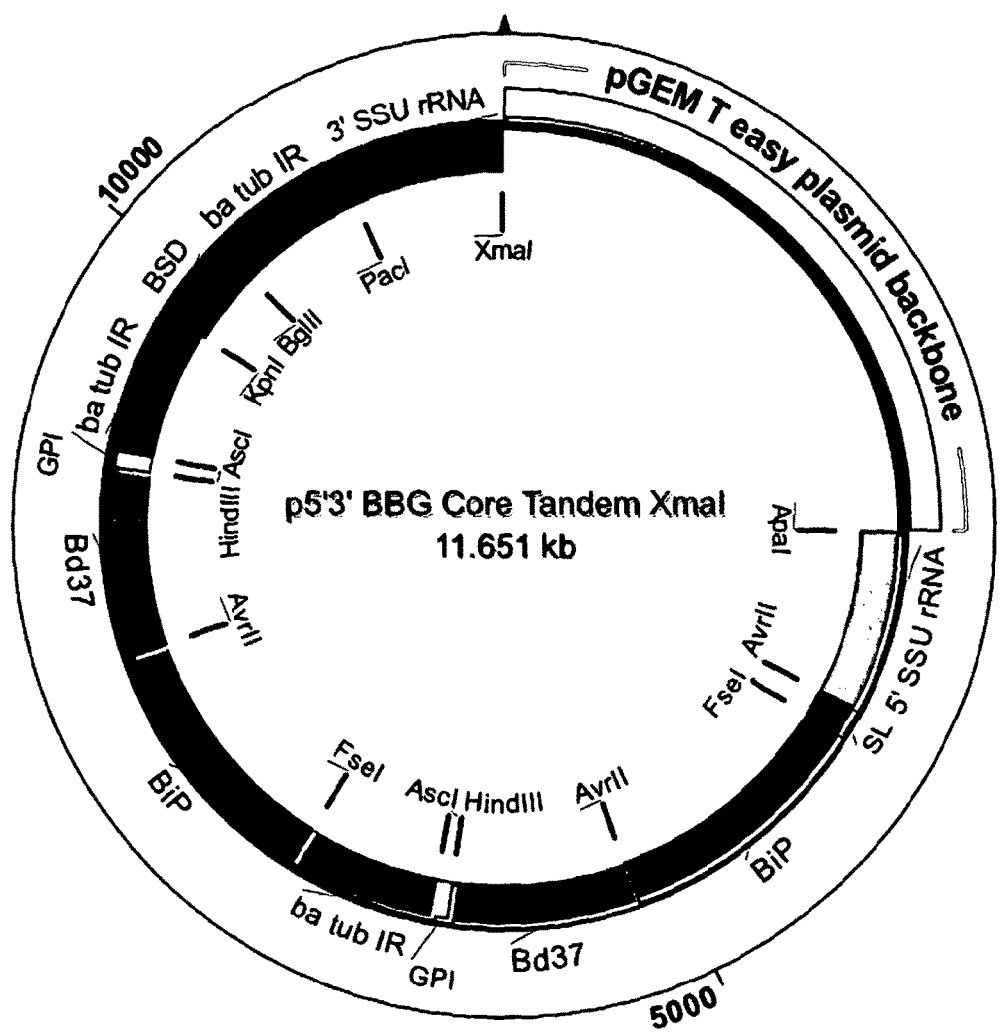
Figure 15:
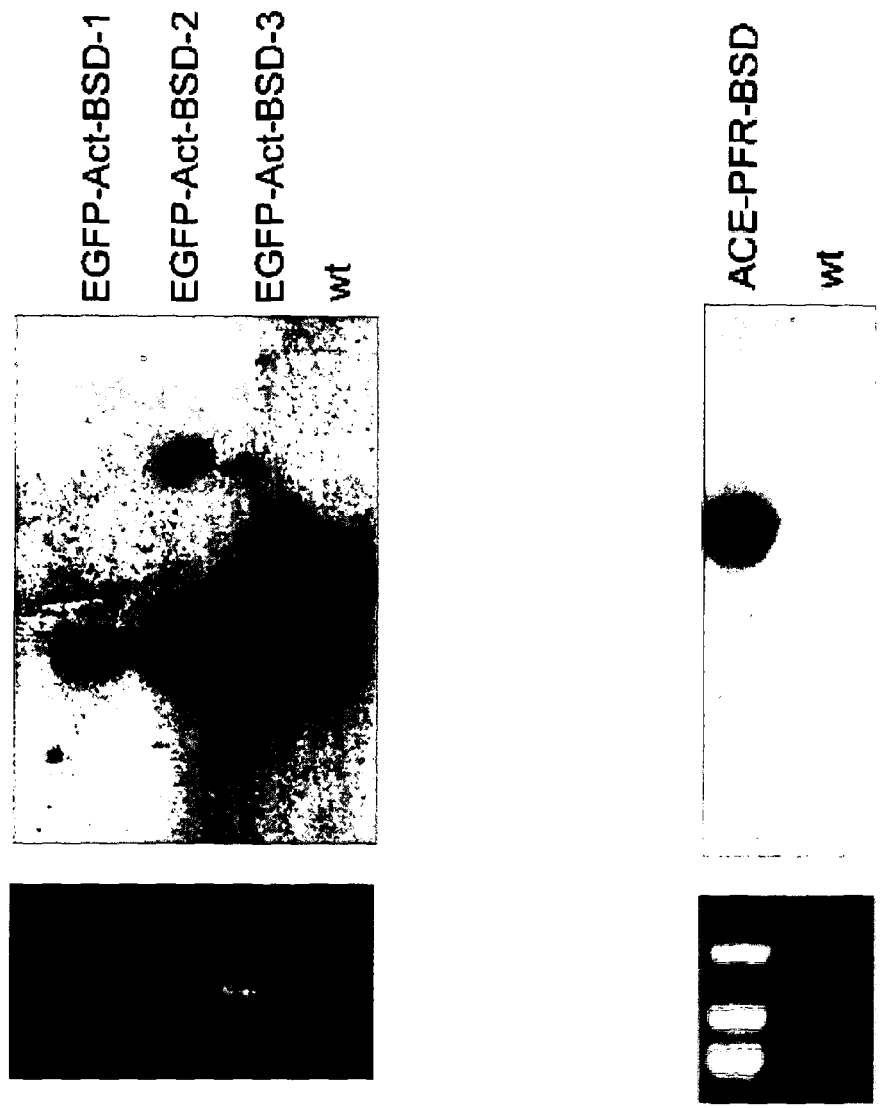
Figure 16:
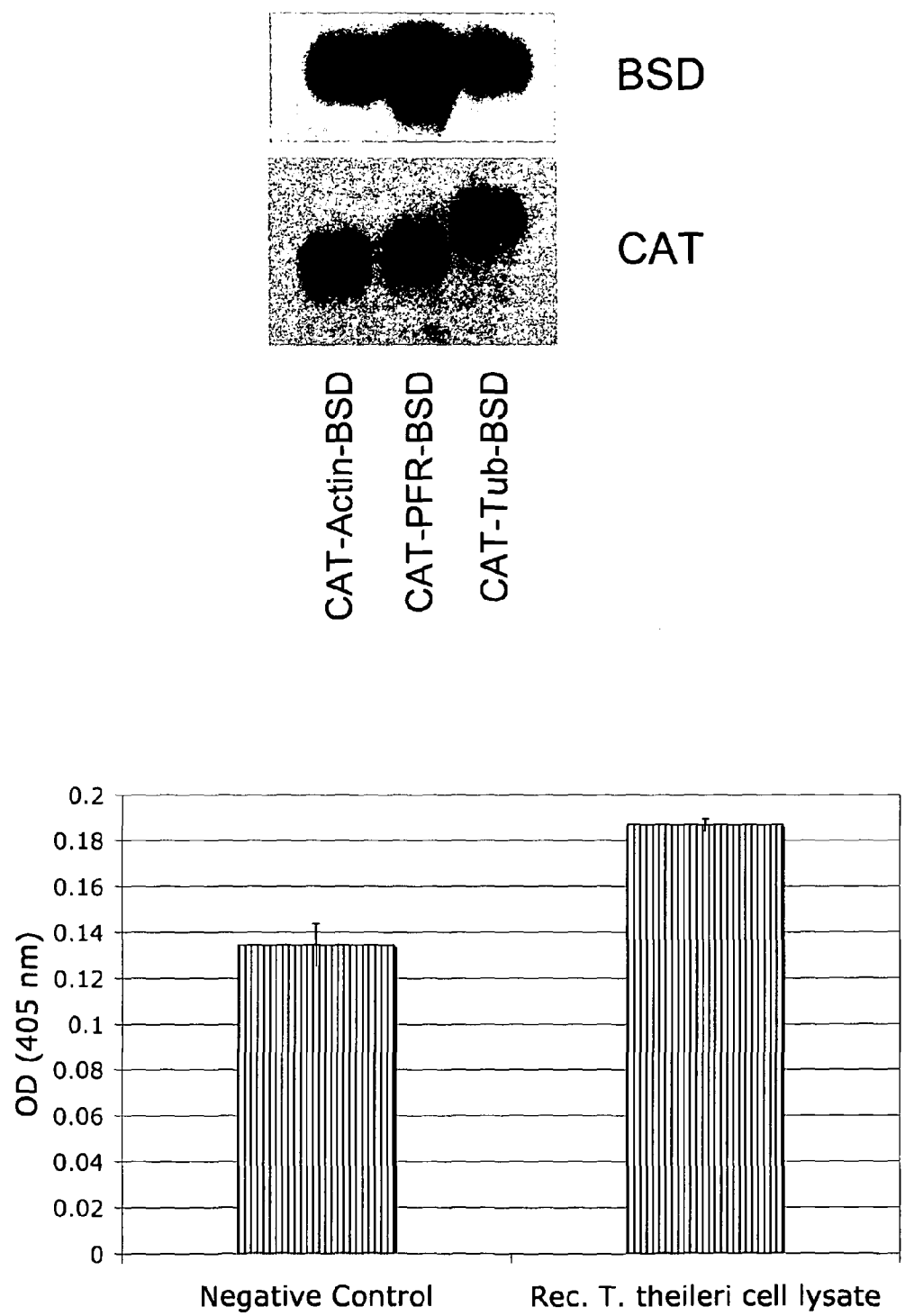

The complete annotated sequences of two exemplary transfervectors are provided; one expressing CAT from the Tubulin IR locus: pabCTBba (SEQ ID NO: 1, FIG. 4), and one expressing a tandem construct of the Bd37 vaccine-antigen from the 18S SSU rRNA gene locus: p53BBTandem (SEQ ID NO: 2, FIG. 11).

The invention will now be further described with reference to the following, non-limiting, examples.

EXAMPLES

1. Basic Methodology of Handling *T. theileri*
1.1. Culturing of *T. theileri* In Vitro
Preparation of *T. theileri* Culture Medium
The base medium used for the culture of *T. theileri* is HMI-9 medium; this can be batch-ordered, e.g. from Invitrogen, and contains: Iscove's Modified Dulbecco's Medium (from powder, Invitrogen 42200-014), with 0.05 mM bathocuproine disulphonic acid, 1.5 mM L-cysteine, 1.0 mM hypoxanthine, 1.0 mM sodium pyruvate and 0.16 mM thymidine.

After receipt, this was dissolved to a liquid medium, supplemented with 3.024 g/l sodium bicarbonate and 14.3 µl/l beta-mercaptoethanol. pH was set to 7.5 with sodium hydroxide, and the HMI-9 medium was stored long-time at 4° C.

Before use (in 500 ml batches) the medium was supplemented additionally with 10% Serum+® (synthetic serum replacement, Sigma, 14008C), 20% Foetal calf serum (FCS) and 1% penicillin-streptomycin solution (Sigma, P0781).

HMI-9 was mixed at 1:1 v/v with freshly harvested MDBK-conditioned medium (see below), and filter sterilised at 0.2 µm to remove any cell debris arising from the MDBK-conditioned medium.

Figure 2:
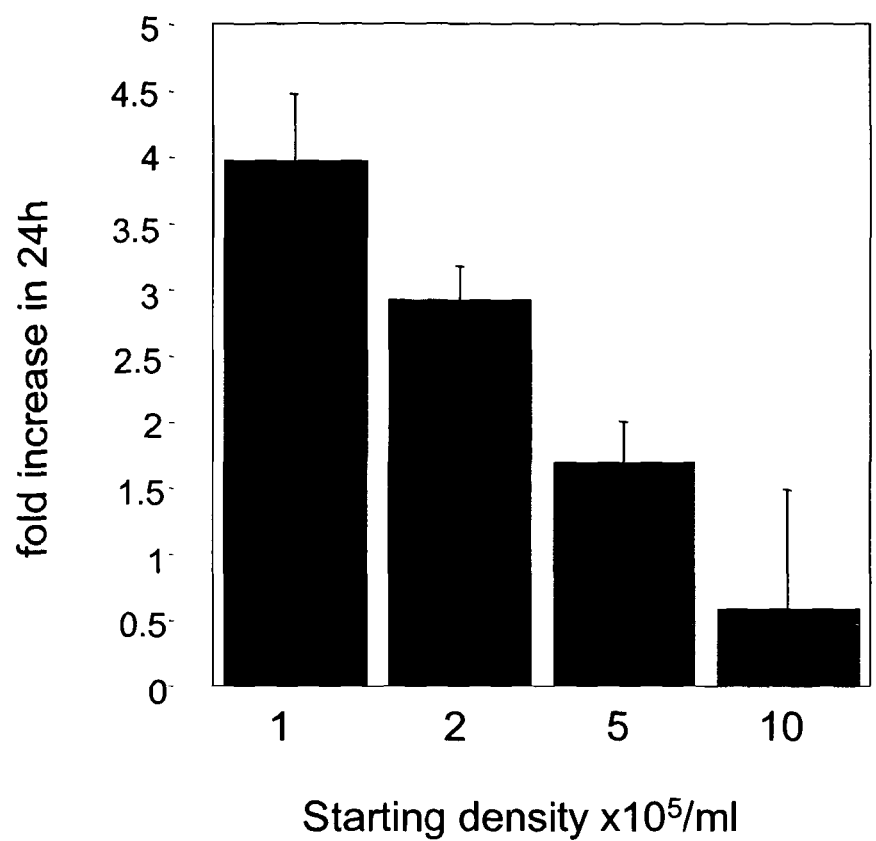
Figure 3:
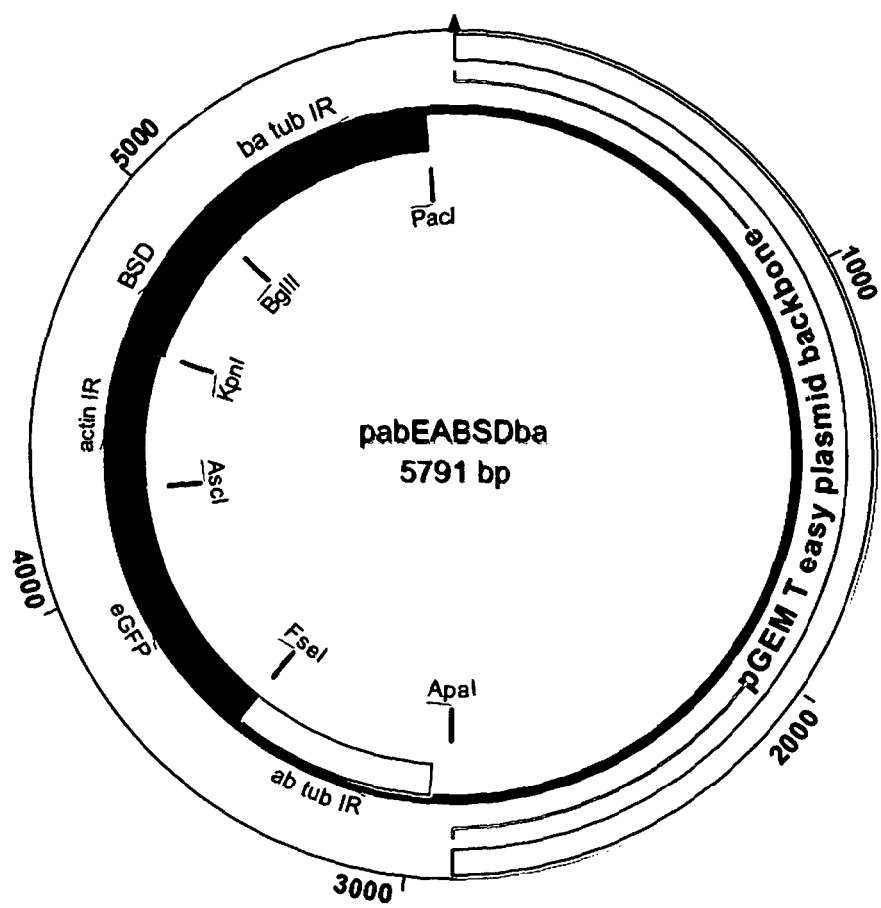

For best results *T. theileri* culture medium was prepared fresh for use the same day. If stored, it was kept at 4° C., and used within 7 days of preparation.
Culturing of *T. theileri* Parasites In FIG. 2, the results are presented from growth of *T. theileri* when sub-passaged at different initial densities: $1\times10^6$/ml; $2\times10^5$/ml; $5\times10^5$/ml and $1\times10^6$/ml. Parasites were diluted every 24 hrs. back to the initial density and the rate of growth was plotted. Optimal proliferation was observed when parasites were seeded at $1\times10^6$/ml; reaching a density of at least $5\times10^5$ cells/ml in one day.

Therefore, cultures of *T. theileri* were routinely examined microscopically and counted every day, and passaged any time that the density exceeds $5\times10^6$ cells/ml. This was because *T. theileri* cultures at densities above $5\times10^6$ cells/ml (or $1\times10^6$ cells/ml for transfectants) start to switch towards the straighter cell morphology with loss of the frilly membrane, and have a lower growth rate, and a higher proportion of aberrant cells.

Counting of *T. theileri* was done using a Z2 Coulter Counter® (Beckman Coulter). Typically 250 µl of cell-culture was diluted in Isoton Diluent® (Beckman Coulter) to a total volume of 10 ml and then measured once.

For practical reasons, cells were routinely passaged only every other day and subcultured when needed.

To start a new culture, a T25 flask with pre-warmed *T. theileri* media was seeded with $4\times10^4$ cells/ml. Seeding should not be below about $1\times10^4$ cells/ml, as lower densities did not always allow for outgrowth of the parasites. All cultures were incubated at 37° C. in 5% $CO_2$.

Continuous in vitro cultures of *T. theileri* parasites in logarithmic growth phase have been maintained for over a year.
1.2. Preparation of Conditioned Medium Conditioned medium was used in *T. theileri* cultures to overcome the requirement for a feeder cell-layer. To prepare appropriate conditioned medium, Madin-Darby bovine kidney (MDBK) epithelial cells were preferred. MDBK cells and components of their culture medium can be obtained from various (non-)commercial sources, for instance from the European cell culture collection (ECACC) as cell line with accession number 90050801.

Preparation of MDBK Culture Medium

The MDBK cell culture base medium was prepared from Eagle's Minimum Essential Medium pre-mixed with Earle's balanced salt solution and sodium bicarbonate (Sigma, M2279). This was supplemented with: 1% MEM non-essential amino acids (Invitrogen, 11140), 1% L-Glutamine solution (from 200 mM solution, Sigma, G7513), and 10% FCS to complete the MDBK-culture medium.

Culturing of MDBK Cells to Produce Conditioned Medium

Actively growing MDBK cells were obtained either from an ongoing culture, or from a frozen stock with some pre-culturing, all using well known techniques.

A culture was started by plating MDBK cells at $4 \times 10^4$ cells/cm$^2$, e.g. by inoculating $3 \times 10^6$ MDBK cells, resuspended and washed with PBS, into a 75 cm$^2$ flask in 15 ml pre-warmed MDBK culture medium. MDBK cells were not seeded below this density as they may not start growing then.

Incubated at 37° C. in 5% $CO_2$ for 2-3 days until cells reached confluency (i.e. there were no gaps left between the cells). Cells were not allowed to overgrow, as that would deplete the medium too much.

The supernatant culture medium was harvested by pipette into a sterile container; since the MDBK cells were adherent, the medium could be removed without many contaminating cells or centrifugation. Any cell debris was removed by filtration later. Preferably the conditioned medium was used for making *T. theileri* culture-medium the same day, but could be kept for up to 7 days, stored at 4° C.

MDBK cell culture could be continued by harvesting and passaging according to well known procedures; in short: a T75 culture flask with confluent MDBK cell layer was decanted, and washed with PBS. The cells were detached using brief exposure to 1 ml of 0.25% trypsin/EDTA followed by brief incubation at 37° C. Next 10 ml of MDBK culture medium was added and detached MDBK cells were harvested, counted, and re-seeded in a new T75 flask with pre-warmed medium in a total volume of 40 ml.

1.3. (Re-)Isolation of *T. theileri* from a Bovine Animal

*T. theileri* parasites could be isolated from bovine blood, to obtain *T. theileri* for recombination, or to re-isolate a recombinant *T. theileri* some time after its inoculation.

A 10 ml sample of bovine blood was collected into an EDTA-containing vacutainer collection tube. The sample was stored at 4° C. and used preferably within one hour, but use up to 24 hrs was possible.

A T25 flask was filled with 8 ml pre-warmed, and freshly prepared *T. theileri* medium. Aseptically add 2 ml of the fresh bovine blood to the T25 flask and incubate for a minimum of 4 hours at 37° C. and 5% $CO_2$ in an incubator, to allow for the coagulation of the blood in the medium.

After incubation and clotting, the supernatant medium was decanted into a new culture flask, being careful not to disturb the solids in the flask. These solids were gently washed once with 3 ml fresh *T. theileri* medium, and this wash medium was also decanted into the new flask. To both flasks the culture medium was filled up to a total volume of about 12 ml. Both flasks were incubated at 37° C. and 5% $CO_2$, and monitored daily by light microscopy for the presence of *T. theileri* at 400× magnification. Parasites were visible within one week of culture in both flasks; the flask with the solids contained more parasites but these were not so easily observed.

The *T. theileri* parasite used by the inventors was obtained using a similar protocol, as a contaminant of a culture of pericytes isolated from retinal microvasculature from a British cow (Canfield, A. E. et al., 1996, J. Cell. Sci., vol. 109, p. 343-353).

1.4. Storage of *T. theileri* Parasites

Cultures of (recombinant) *T. theileri* could be kept at room temperature up to one week, while maintaining viability. However, for long-time storage of *T. theileri* parasites, they were stored frozen, using a freezing medium; this consisted of *T. theileri* culturing medium (incorporating 50% MDBK conditioned medium) and 14% glycerol. The freezing medium was pre-warmed to 37° C. before use.

Next, *T. theileri* cells were harvested from an actively growing culture by centrifugation at 1000×g for 10 minutes at room temperature. Carefully decant the medium supernatant. The *T. theileri* cells were then resuspended in *T. theileri* freezing medium at a concentration of about $2 \times 10^5$ cells/ml. This mixture was aliquoted into appropriate containers for frozen storage, for example into 1 ml cryotubes.

The cryotubes were carefully cooled down at about 1-3° C./min, for instance by placing in a polystyrene box and placing the box at −80° C. overnight. Next day the cooled cryotubes could be placed in long-term frozen storage: at −80° C. for storage of weeks-months, or in liquid nitrogen for storage of years.

Thawing and reviving (recombinant) *T. theileri* parasites from long-term cold storage as frozen stabilates in glycerol could for example be done in the following way: T25 culture flasks with 10 ml of prewarmed and freshly prepared *T. theileri* culture medium were made ready. The ampoule containing the *T. theileri* was removed from cold storage and transported to the laboratory on ice (in less than 5 minutes). The vial was thawed quickly by swirling the bottom of the tube in a water bath at 37° C. for approximately 1 minute, until the frozen content releases from the side of the ampoule. The vial was then disinfected by liberal application of a 70% ethanol solution. To transfer the culture from the tube, 1 ml of pre-warmed *T. theileri* media was pipetted into the ampoule and the whole content was dropped into the T25 culture flask. The culture was then left to recover overnight in an incubator (37° C., 5% $CO_2$). Next day the *T. theileri* parasites were counted and cultured in fresh medium, and in the case of transfected *T. theileri*, the proper amount of a selective drug was added.

2. Obtaining *T. theileri* Genomic Sequence Information

For the construction of the various vectors, cassettes and mutant parasites according to the invention, the inventors had to identify the required genetic information from the genome of *T. theileri*, for use as target region for insertion of a mutation according to the invention, and/or to provide RNA processing signals for the expression of heterologous nucleic acid sequence inserts.

For lack of genetic information from *T. theileri*, the inventors derived consensus sequences for desired genes and untranslated regions of *T. theileri* from corresponding genomic regions from *T. brucei* and *T. cruzi*, using for example Genbank publications NZ_AAHB00000000 and NZ_AAHK00000000 respectively. Next, degenerated PCR primers were designed that incorporated the variations observed, to amplify the desired region of the *T. theileri* genome. The actual cloning and sequencing techniques were based on standard protocols.

To overcome the variation between the IR sequences of *Trypanosoma* species the focus was repeated gene clusters in the *T. theileri* genome. PCR amplification was then started from the more conserved ends of the coding regions, which allowed the PCR to proceed into the unknown IR's.

This approach was applied to obtain the *T. theileri* IR from two regions of the Tubulin gene cluster, and one from the PFR gene region. The degenerated primers used were:

| SEQ ID NO | Primer name | Sequence 5'->3' |
|---|---|---|
| 3 | a-tub rev | cccaaraarttraaigcrtcrtcytcitcicc |
| 4 | b-tub UTR | ggiatggaygaratggarttyacigargc |
| 5 | a-Tubulin F | cccgciaaigticarmgigcigtitgyatgatigc |
| 6 | b-Tubulin R | ccciaaigtcatcatiaticiitciggita |
| 7 | PFR-F | gggaarcargargargtiaaratigcigcigar |
| 8 | PFR-R | gggrttrtgiatyttytgytticki gcigcytc |

The nucleotides of the degenerated primers are represented in standard IUB code, wherein r=a or g, i=inosine, y=c or t, m=a or c, s=c or g and w=a or t.

For the Tubulin alpha-beta IR, after amplification by degenerated primers, a set of regular primers was used to obtain the entire alpha-beta Tubulin IR sequence:

| SEQ ID NO | Primer name | Sequence 5'->3' |
|---|---|---|
| 9 | Tub-UTR for | ggagtactagatatgtagagc |
| 10 | Tub-UTR rev | ccctgaacacacacaatctcgc |

This way a number of IR sequences were determined, which could advantageously be used either as genomic targeting regions for the insertion of a mutation according to the invention, or for providing the required RNA processing signals for expression of an inserted heterologous sequence.

In SEQ ID NO's: 11-13 (and 20) are presented IR sequences (represented from the first nucleotide of the IR after the upstream stop codon, through to the last nucleotide of the IR before the downstream start-codon) from:
SEQ ID NO: 11 beta-alpha Tubulin intergenic region

SEQ ID NO: 12: alpha-beta Tubulin intergenic region

SEQ ID NO: 13: PFR intergenic region

In areas of the *T. theileri* genome that were found to be more conserved, the use of degenerated primers was not necessary, and consensus primers could advantageously be used. This was applied to obtaining the Actin IR and to obtain the 5' en 3' ends of the 18S SSU rRNA genome region of *T. theileri*, by way of the following primers:

| SEQ ID NO | Primer name | Sequence 5'->3' |
|---|---|---|
| 14 | Actin-UTR For | gggtatcgtacacaacaagtg |
| 15 | Actin-UTR Rev | ccctagcagattgctcctcctc |
| 16 | SSU5-ApaI-For | atagggcccgcatggctcattacatcagacg |
| 17 | SSU5-AvrII-Rev | agacctaggcaacaaaagccgaaacggtagcc |

-continued

| SEQ ID NO | Primer name | Sequence 5'->3' |
|---|---|---|
| 18 | SSU3-PacI-For | gggttaattaaatcctcagcacgtttcttactt |
| 19 | SSU3-Rev-For For | atacccgggctgcaggcaggttca |

This way the Actin IR and both ends of the 18S SSU rRNA gene region of the *T. theileri* genome could be determined. All these could conveniently be used as target region for mutation insertion, and the actin IR could serve as RNA processing signal.

For the actin IR (SEQ ID NO: 20), the same sequence of 392 nucleotides was identified from 3 different actin IR's in the Actin tandem gene array, and it is therefore a consensus sequence. The part of the *T. theileri* actin IR that provides the splice-leader acceptor site (SEQ ID NO: 21), was found to be comprised in the 3' part of this actin IR that begins at nucleotide 256 of SEQ ID NO 20.

Further genome targeting regions for use in the invention are the 5' and 3' regions of the *T. theileri* 18s SSU rRNA gene, presented herein as:
SEQ ID NO: 22: 5' end of 18s SSU rRNA
SEQ ID NO: 23: 3' end of 18s SSU rRNA.

3. Construction of Integration Cassettes and Transfer Vectors

The *T. theileri* transfervectors for the invention were assembled in a modular way, so that different elements could conveniently be exchanged, to create different integration cassettes, and thus generate the different recombinant *T. theileri* parasites tested. Graphical representations of a number of exemplary insertion cassettes are represented in FIG. 1, and transfervectors are in FIGS. 3-14.

The plasmid backbone used for all experiments was derived from the pGemT Easy® plasmid (Promega) that was linearised using its PstI and ApaI restriction enzyme recognition sites. The inserts made introduced some modified restriction sites that were convenient for the excision of the integration cassettes; the Tubulin based cassettes used ApaI and PstI restriction sites, and the 18S SSU based cassettes used ApaI and XmaI sites. These manipulations were all done using PCR cloning primers according to standard protocols. The relevant PCR cloning primers used in the course of the construction work are listed below.

For Tubulin IR based insertion cassettes, the targeting sequences used for directing the homologous recombination are two IR sequences from the Tubulin gene region. Each was adapted to have convenient restriction enzyme sites for directional cloning; the alpha-beta Tubulin IR (SEQ ID NO: 12) was adapted to an ApaI-FseI fragment using primers ab-tub NotI and ab-tub FseI (SEQ ID NO's: 24 and 25) (because in this case the ApaI site is derived from the pGEM backbone itself). Similarly, the beta-alpha Tubulin IR (SEQ ID NO: 11) was adapted to a BglII-PacI fragment using primers ba-tub BglII and ba-tub PacI (SEQ ID NO's: 26 and 27).

For 18S SSU rRNA gene based insertion cassettes, the two ends of the gene were incorporated into a transfervector, after adaptation of their end sequences whereby the 5' 18S SSU rRNA gene fragment (SEQ ID NO: 22) was adapted to an ApaI-AvrII fragment using primers SSU5-ApaI-For and SSU5-AvrII-Rev (SEQ ID NO's: 28 and 29); and the 3' 18S SSU rRNA gene fragment (SEQ ID NO: 23) was adapted to a PacI-XmaI fragment using primers SSU3-PacI-For and 3SSU-Rev-XmaI (SEQ ID NO's: 30 and 31).

| SEQ ID NO | Primer name | Sequence 5'->3 |
|---|---|---|
| 24 | ab-tub-NotI | aaagcggccgctagatatgtagagctacccc |
| 25 | ab-tub-FseI | cccggccggccatttctcttcagactgttattc |
| 26 | ba-tub-BglII | gggagatcttaaatgggatacatgggggtgc |
| 27 | ba-tub-PacI | gggttaattaagttgaaaaaaagaaaaaacttg |
| 28 | SSU5-ApaI-For | atagggcccgcatggctcattacatcagacg |
| 29 | SSU5-AvrII-Rev | agacctaggcaacaaaagccgaaacggtagcc |
| 30 | SSU3-PacI-For | gggttaattaaatcctcagcacgtttcttactt |
| 31 | 3SSU-Rev-XmaI | atacccgggctgcaggcaggttca |

Wherein: ab-tub=alpha-beta Tubulin IR; ba-tub=beta-alpha Tubulin IR; SSU5=5' end of 18S SSU rRNA gene; SSU3=3' end of 18S SSU rRNA gene.

Subsequently, a wide variety of other elements has been incorporated in these transfervectors, and was transfected into *T. theileri* parasites. Described here are: the antibiotic resistance gene for Blasticidin (BSD) (nucleotides 4934 through 5326 from SEQ ID NO: 1); marker genes eGFP (SEQ ID NO: 77) and CAT (nucleotides 3590 through 4249 from SEQ ID NO: 1); and antigen genes sACE-1 (SEQ ID NO: 78) and Bd37 (nucleotides 5200 through 6222 from SEQ ID NO: 2).

Each of these was appropriately flanked with RNA processing signals as described above.

Also, the heterologous nucleic acid sequences for expression of a protein could be flanked by trafficking signals: N-terminal BiP fragment (nucleotides 3949 through 5193 from SEQ ID NO: 2), or a GPI anchor (SEQ ID NO: 79).

For the Bd37 gene insert a shortened 'core' version was created (SEQ ID NO: 80), wherein the hydrophobic sequences of the native Bd37 N-terminal signal sequence and C-terminal GPI anchor were deleted, to be able to accurately manipulate its protein-trafficking behaviour.

All these elements were provided with convenient restriction sites by PCR, using PCR cloning primers SEQ ID NO's: 32-66, see Table 1, to allow directional cloning. The specific restriction enzyme sites used varied, dependent on the order in which these elements were incorporated in a particular insertion cassette, and the restriction sites used for the other elements.

Throughout all manipulations, care was taken not to disturb the reading frame by introduction of stop codons: all restriction enzymes used had 6 base recognition sites, therefore only changed or introduced two amino acids but left the reading frame intact. Also, when an N- or C-terminal fusion was introduced, the native start or stop codon was removed, and was provided by the fused sequence. The Bd37 core sequence without trafficking signals was provided with new start and stop signals, also respecting its reading frame.

Transfervectors were constructed and amplified in *E. coli* bacteria according to standard procedures.

TABLE 1

Cloning primers used for the construction of various insertion cassettes and transfervectors for *T. theileri* recombination

| SEQ ID NO | Primer name | Sequence 5'->3 |
|---|---|---|
| 32 | Actin-AscI | ggggcgcgcctggcttgtgtttatctatttc |
| 33 | Actin-KpnI | cccggtacctgttgaaatagtaactcg |
| 34 | ba-tub-AscI-For | ggaggcgcgccaaatgggatacatggggg |
| 35 | ba-tub-KpnI-Rev | ggaggtaccgttgaaaaaaagaaaaaacttg |
| 36 | splice-AvrII-For | gggcctagggtcgttgttatcgttgtacg |
| 37 | splice-FseI-Rev | gacggccggccgaaatagtaactcgatatgc |
| 38 | BSDKpn-F | cccggtaccatggccaagcctttgtctcaa |
| 39 | BSDBgl-R | cccagatctttagccctcccacacataaccag |
| 40 | BSD For FseI | ataggccggccatggccaagcctttgtctcaa |
| 41 | BSD Rev AscI | ataggcgcgccttagccctcccacacataaccag |
| 42 | BiP-For-FseI | agaggccggccatgtcgaggatgtggctgacc |
| 43 | BiP-Rev-XhoI | gggctcgagcccgccaacctcgctttcaccg |
| 44 | BiP-For-KpnI | ataggtaccatgtcgaggatgtggctgacc |
| 45 | BiP-For-FseI-SpeI | ataggccggccactagtatgtcgaggatgtggctgacc |
| 46 | GPI-Rev-BglII | ataagatctttagaatgcggcaacgagagc |
| 47 | GPI-For-XbaI | atatctagacctgaacctggtgctgcaacgc |

TABLE 1-continued

Cloning primers used for the construction of various insertion cassettes and transfervectors for *T. theileri* recombination

| SEQ ID NO | Primer name | Sequence 5'->3 |
|---|---|---|
| 48 | GPI-Rev-AscI | ataggcgcgccttagaatgcggcaacgagagc |
| 49 | GPI-For-HindIII | ataaagcttcctgaacctggtgctgcaacgc |
| 50 | Bd37-Core-F-FseI | ataggccggccatgttcaatggcaataatgtgagc tgc |
| 51 | Bd37-Core-R-AscI | ataggcgcgccttatccctgacctgatcctgcagc aca |
| 52 | Bd37-Core-F-AvrII | atacctaggttcaatggcaataatgtgagctgc |
| 53 | Bd37-Core-R-HindIII | ataaagctttccctgacctgatcctgcagcaca |
| 54 | ACE-full Fse | GGAGGCCGGCCATGAGTCCACTTTGAAGGAAAG |
| 55 | ACE-full Asc | ATAGGCGCGCCTCGCTTGTGCTTCTCGGTTCTC |
| 56 | ACE-Acc65-F | GGAGGTACCATGAGAGTCCACTTTGAAGGAAA |
| 57 | ACE-Bgl-R | GGGAGATCTCTATTCGCTTGTGCTACTC |
| 58 | EGFP-FseI | GGGGGCCGGCCATGGTGAGCAAGGGCGAGG |
| 59 | EGFP-AscI | GGGGGCGCGCCTTACTTGTACAGCTCGTCC |
| 60 | CAT For FseI | ATAGGCCGGCCATGGAGAAAAAAATCACTGGATAT |
| 61 | CAT Rev AscI | ATAGGCGCGCCTTACGCCCCGCCCTGC |
| 62 | CAT For XhoI | GGGCTCGAGGAGAAAAAAATCACTGGATATACC |
| 63 | CAT Rev XbaI | ATATCTAGACGCCCCGCCCTGCCA |
| 64 | CAT For KpnI | ATAGGTACCATGGAGAAAAAAATCACTGGATAT |
| 65 | CAT Rev BgIII | ATAAGATCTTTACGCCCCGCCCTGC |
| 66 | CAT For FseI | ATAGGCCGGCCATGGAGAAAAAAATCACTGGATAT |

Wherein in Table 1:

Actin=actin IR-complete; ba-tub=beta-alpha Tubulin IR; splice=Actin IR-splice leader acceptor site; Bd37-core=Bd37 sequence without hydrophobic sequences at its termini; and ACE full=full length sACE-1 gene from *D. viviparus.*

4. Transfection of *T. theileri*

4.1. Preparation of Cells and Transfection Protocol

From a culture of logarithmically growing *T. theileri* parasites, at least 10 ml of culture at about $5\times10^5$ cells/ml was used for each transfection. The transfections were done as quickly as possible to minimize the amount of time the cells were at room temperature. The cells were pelleted by centrifugation at 1000×g, for 10 minutes at room temperature.

Under sterile conditions, e.g. in a laminar airflow cabinet, the medium supernatant was carefully removed and the *T. theileri* cell pellet was resuspended into 1 ml of sterile PBS to wash the cells. This was re-centrifuged at 1000×g (10 min., room temp.). Meanwhile, T25 culture flasks (1 per transfection) were prepared with 10 ml of pre-warmed *T. theileri* medium.

The PBS supernatant was discarded and the pelleted cells resuspended in 100 μl Ingenio® transfection buffer (Mirus Bio). The vector DNA was prepared as described below, in an amount of at least 7.5 μg of linear DNA to approximately $1\times10^7$ cells, and placed in a cuvette for the Nucleofector II® electroporation device (Lonza).

Transfection was done with Nucleofector program X-001 (recommended for mouse CD8+ T cells). Immediately after the electroporation, the cells were transferred to the pre-prepared culture flask, and incubated for 24 hrs (at 37° C., in 5% $CO_2$).

4.2. Preparation of Transfervector DNA

Transfervectors were constructed and analysed as described above. For transfection, 15 μg of plasmid DNA was digested with an appropriate restriction enzyme to linearise the vector, and to excise the pGEM T Easy® plasmid backbone. Transfervectors for Tubulin IR targeting experiments were digested with the enzymes ApaI and PstI, and transfervectors for targeting to the 18S SSU rRNA gene were digested with ApaI and XmaI.

The digested plasmid fragments were separated by gel electrophoresis on a 1% agarose gel. The resulting bands were visualized on a UV transilluminator and the band corresponding to the integration cassette was excised from the gel, thereby purifying it away from the vector backbone. The linear DNA of the integration cassette was purified using a NucleoSpin® Extract II® kit (Macherey-Nagel) as per manufacturer's instructions except that the elution was done for four consecutive times with 50 μl of the elution buffer provided with the kit, to a total elution volume of 200 microliters. Next the eluted DNA was precipitated with ethanol/acetate at −80° C. After centrifugation, the supernatant was carefully removed, the pellet was air-dried, and resuspended in 5 μl TE buffer (1 mM Tris-HCl (pH 8) and 0.1 mM EDTA).

4.3. Selection of Transfectants

Transfected *T. theileri* parasites are placed under drug selection to select out those cells that were successfully and stably transfected. Therefore, after the initial 24 hour recovery period each transfection was processed: 0.5 ml of each culture is placed in a well of a 24-well plate to act as a 'no drug' control, to which fresh *T. theileri* media is added to a total volume of 2 ml. The remainder of the culture was centrifuged (1000×g, room temp.) for 10 minutes. Cells were resuspended in 10 ml of pre-warmed *T. theileri* culture medium containing the selective drug at the selective concentration. For the transfervectors used in these experiments Blasticidin is the drug for selection, used at a final concentration of 10 µg/ml.

The resuspended cells were aliquotted into 24 well plates at 1:2, 1:10 and 1:20 dilutions in *T. theileri* culture medium and the volume of each well was brought to 2 ml with pre-warmed *T. theileri* media containing the selective drug. The plates were examined daily under the light-microscope. After 5-7 days 1 ml of medium was carefully removed from the top of each well by pipette, and replaced by 1 ml of fresh *T. theileri* culture medium with the selective drug at the appropriate concentration.

Those *T. theileri* cells not effectively transfected, died off within a few days. The cells in the 'no-drug' control well however grew out in any case, indicating that the transfection itself had not damaged the cells. After 10-14 days of incubation, the transfectants surviving the selection became visible, as actively swimming parasites. These were further amplified and either stored as described, or used for analysis of insert and expression (see below).

5. Northern Blot Analysis of Recombinant *T. theileri* mRNA Transcription Levels In vitro mRNA transcription levels were determined from stably transfected recombinant *T. theileri* parasites that incorporated heterologous genes like eGFP, CAT, ACE, and Bd37, either inserted in the Tubulin IR genomic region or in the 18S SSU rRNA gene.

5.1. Harvest of RNA from *T. theileri*

To collect RNA samples, 25 ml cell cultures of logarithmically growing recombinant *T. theileri* parasites were used; these were centrifuged at 1000×g for 10 minutes at room temperature. RNA samples were isolated using the QIAGEN RNEasy® Mini Kit (Qiagen, 74106) as per the manufacturer's instructions, using the optional DNase treatment steps as described. Next RNA samples were stored at −80° C. until processing.

5.2. Preparation of the Riboprobes

The target sequence of the riboprobe reaction is cloned into pGEM T Easy® vector as per the manufacturer's instructions (Promega, A1360). Linear probes were produced via PCR reaction, by way of M13 primed PCR. The PCR labelling reaction components are: 1 µl template DNA (about 100 ng); 5 µl 5×DNA Pol Buffer; 1.25 µl MgCl$_2$ (25 mM); 0.1 µl M13 forward primer (100 µM); 0.1 µl M13 reverse primer (100 µM); 0.25 µl dNTPs (2 mM each); 0.25 µl DNA Pol enzyme (5 U/ml); and 17.05 µl double distilled water up to 25 µl.

Next the PCR was run as follows: start with 5 min. 95° C.; followed by 35 cycles of: 95° C. 45 s., 60° C. 45 s., and 72° C. 1 min. Finally 72° C. for 5 min.

The PCR product was DIG-labelled using the DIG RNA Labelling Kit® (SP6/T7) (Roche, 11175025910) as per the manufacturer's instructions, to produce Dig labelled riboprobes. The probes were stored at −80° C. until use.

5.3. RNA Gel Electrophoresis and Northern Blotting

RNA gel electrophoresis, and the subsequent transfer, and blotting was performed essentially according to the manufacturer's instructions of the DIG Northern Starter Kit® (Roche, 12039672910), with some amendments: Agarose gels contained 1.1% v/v formaldehyde and were run for 2 hours at 150 V. Transfer was to positively-charged Nylon membrane by capillary transfer with 20×SSC overnight. Next the membranes were fixed by UV-cross linking (0.12 joules, 254 nm), and blocking and hybridization steps were done in a hybridization oven at 68° C.

5.4. Northern Blot Probe Sequences

The various probes used for labelling and hybridisations, were mostly based on the entire coding sequence of the various inserted genes; The primers for making the riboprobes are described in Table 1, and were, for eGFP: primers EGFP-FseI and EGFP-AscI; for CAT: CAT For FseI and CAT Rev AscI; for BSD: BSD For FseI and BSD Rev AscI; for sACE-1: ACE-full Fse and ACE-full Asc.

The Bd37 probe contained only a part of the Bd37 gene, and was generated using primers:

| SEQ ID NO | Primer name | Sequence 5'->3 |
|---|---|---|
| 67 | Bd37 Northern | FACGCAGCAAGGTGGTGCGAA |
| 68 | Bd37 Northern | RGCGCTGCTTCAACACTGTCACC |

6. CAT Elisa Assays

The expression of Chloramphenicol transferase (CAT) from the CAT gene inserted in recombinant *T. theileri* parasites was detected by Elisa, using a CAT ELISA® kit (Roche, 11363727001) according to the manufacturer's instructions. In short:

From a logarithmically growing parasite culture, at a concentration between 0.5 and 1×10^6 cells/ml, a precise parasite cell count was made immediately prior to sample preparation, to be able to calculate CAT expression per 10^6 parasites later. A sample of 10 nil of the counted culture was centrifuged (1000×g, 10 min., room temperature), and the cell pellet was washed 3 times in 1 ml of cold 1×PBS. Finally parasites were recovered by centrifugation in a 1.5 ml Eppendorf tube at 4000×g for 2 min. at room temp. The pelleted cells were resuspended in 1 ml of 1× Lysis buffer (provided with the kit) by rapping the tubes along a tube rack and then left to stand for 20 minutes at room temperature. Next the sample was centrifuged at 4000×g for 5 minutes to remove cell debris. The lysis-supernatant was divided into 2×500 µl in fresh Eppendorf tubes, snap frozen in liquid nitrogen, and stored at −80° C. until use. Samples of wild-type *T. theileri* were also harvested as negative controls.

The CAT ELISA was carried out as per the manufacturer's instructions with 1:10 and 1:100 dilutions of the cell-lysates, and CAT protein expression was measured by reading of the OD 405 nm. For determining quantitative expression levels, CAT expression levels were calculated in ng/10^6 parasites (in starting sample), from a reference sample of CAT protein of known concentration, according to the manufacturer's instructions.

7. In Vitro Results of Heterologous Expression by Recombinant *T. theileri* Parasites

7.1. eGFP Expression by Recombinant *T. theileri* Parasites from the Tubulin IR Locus Recombinant *T. theileri* parasites were generated with transfervector pabEABSDba (FIG. 3), which expressed the enhanced green fluorescent protein (eGFP) gene from the Tubulin IR genomic locus.

Stable recombinants were selected using Blasticidin drug-selection, and three lines of recombinant parasites were amplified in vitro. RNA was isolated from each line, as described above, and tested with a DIG-labelled riboprobe specific for eGFP mRNA. Results are presented in the left panels of FIG. 15: The lower left panel represents an image from an agarose gel, stained with Ethidium bromide, showing the total RNA that was loaded and run, before the gel was blotted. This serves to demonstrate that the loading of the RNA into the lanes was even.

The upper left panel shows the results after the blotting and hybridisation. eGFP mRNA was detected in all three lines of recombinant *T. theileri* parasites, but not in wildtype *T. theileri* RNA (untransfected parental cell-line). Some difference in the level of expression can be observed, however that reflects minor variability in sampling and processing.

In conclusion: all three independent lines of recombinant *T. theileri* express the eGFP gene from the Tubulin IR locus, in addition to expression of the Blasticidin drug-resistance gene.

7.2. sACE-1 Expression by Recombinant *T. theileri* Parasites from the Tubulin IR Locus Similar to the eGFP Northern blots described above, recombinant *T. theileri* parasites that expressed a soluble version of the *D. viviparus* acetylcholinesterase-1 (sACE-1) from the Tubulin IR locus, were generated, drug selected, and grown in vitro. The transfervector used to make the recombinant *T. theileri* tested here, was highly similar to the ones displayed in FIGS. 3 and 4, with two modifications: the ACE gene was incorporated in the upstream expression position, instead of eGFP or CAT; and the IR sequence in front of the downstream BSD gene was the PFR IR sequence in stead of the actin IR or the beta-alpha tubulin IR.

Results are presented in the right panels of FIG. 15, which show that ACE specific mRNA was detected from the recombinant parasite, but no expression was observed by the wild type parasite, even though the RNA amounts loaded were not completely equal.

In conclusion: a recombinant *T. theileri* was made that was shown to express the sACE-1 gene from the Tubulin IR genomic locus, next to expression of the Blasticidin drug-resistance gene.

7.3. CAT Expression by Recombinant *T. theileri* Parasites from the Tubulin IR Locus Again similar to the results above for the expression of the eGFP and ACE genes, the expression of a CAT gene from the Tubulin IR genomic locus was demonstrated for differently constructed recombinant *T. theileri* parasites; all expressing CAT, but varying in the IR sequence that was incorporated in between the CAT and the BSD gene; IR sequences used were from beta-alpha Tubulin IR (the map of the transfervector used is represented in FIG. 4); from PFR IR, and from the Actin IR (maps not represented but highly similar).

All three recombinants expressed the CAT gene (in addition to the BSD gene), as demonstrated by Northern blot and by CAT protein Elisa; results are presented in FIG. 16.

In the top two panels of FIG. 16, the Northern blot results of the three different recombinant *T. theileri* tested with a labelled CAT specific riboprobe are displayed. The difference in length observed for the CAT mRNA's is caused by the difference in length of the IR region used. For comparison, the expression of the BSD gene in these three recombinants was also tested by Northern blot, and is displayed in the top-most panel.

The bottom panel of FIG. 16 displays the results of an Elisa detecting CAT protein expression, for a negative control, and a CAT expressing recombinant *T. theileri*: the recombinant was produced using the pabCTBba transfervector (FIG. 4; a full and annotated sequence of this plasmid is presented in SEQ ID NO: 1).

In conclusion, it was once more demonstrated that recombinant *T. theileri* could be generated that express a heterologous nucleic acid, here: BSD, and CAT, and that modifications could be made in the design of the expression construct to vary and thus optimise expression as required.

7.4. Protein Expression by Recombinant *T. theileri* Parasites from the 18S SSU rRNA Gene Locus Similar to expression from the Tubulin IR locus, recombinant *T. theileri* parasites were also generated that expressed a number of proteins from the 18S SSU rRNA locus on their genome. Again, different genes were integrated and expressed, in different constellations, and with varying IR sequences. Some of the transfervectors used in these experiments are presented in FIGS. 5-14. Expression was demonstrated by way of Northern blotting and by Elisa for specific proteins.

An overview of results for the expression of one or more CAT genes in different conformations, from the 18S SSU rRNA genomic locus of recombinant *T. theileri* parasites in vitro is presented in Table 2.

The various constructs tested, having different elements in the insertion cassettes, are presented schematically. For most of these a corresponding vector map is presented in the Figures, numbers are indicated in the table. Protein genes used for this set of experiments were CAT and BSD; mostly CAT was present upstream of BSD, but the reverse was also tested. CAT has been inserted as single or as tandem insert, and either with or without signal sequences; signal sequences were either the BiP N-terminal signal or both BiP and a GPI anchor sequence.

CAT expression was determined by Elisa as described. To study protein trafficking and the effect thereon from N- or C-terminal sequences, CAT expression was also quantified in cell-culture supernatants, and the percentage of secreted CAT per total CAT expressed was calculated.

TABLE 2

Protein expression results from various constructs with one or more CAT genes in the 18S SSU rRNA gene of a recombinant *T. theileri* parasite

| FIG. | insertion cassette from 5'-> 3' | | | | | | | | | | | CAT expression ng/10^6 trypanosomes. Cellular | Secreted | % secr/ total |
|---|---|---|---|---|---|---|---|---|---|---|---|---|---|---|
| 5 | 5' SSU-Spl Lead | — | CAT | — | — | — | — | — | actin IR | BSD | ba Tub IR-3' SSU | 27.3 | 15.6 | 36 |
| no fig. | 5' SSU-Spl Lead | — | CAT | — | — | — | — | — | PFR IR | BSD | ba Tub IR-3' SSU | 22.1 | 8.5 | 28 |

TABLE 2-continued Protein expression results from various constructs with one or more CAT genes in the 18S SSU rRNA gene of a recombinant *T. theileri* parasite

| FIG. | insertion cassette from 5'-> 3' | | | | | | | | | | CAT expression ng/10^6 trypanosomes. | | | |
|---|---|---|---|---|---|---|---|---|---|---|---|---|---|---|
| | | | | | | | | | | | Cellular | Secreted | % secr/ total | |
| no fig. | 5' SSU-Spl Lead | — | CAT | — | — | — | — | — | ba Tub IR | BSD | ba Tub IR-3' SSU | 27.6 | 17.1 | 38 | intracellular |
| no fig. | 5' SSU-Spl Lead | — | BSD | — | — | — | — | — | actin IR | CAT | ba Tub IR-3' SSU | 46.3 | 15.7 | 25 | |
| no fig. | 5' SSU-Spl Lead | — | BSD | — | — | — | — | — | PFR IR | CAT | ba Tub IR-3' SSU | 38.3 | 11.6 | 23 | |
| 6 | 5' SSU-Spl Lead | — | BSD | — | — | — | — | — | ba Tub IR | CAT | ba Tub IR-3' SSU | 66.9 | 11.7 | 15 | |
| 7 | 5' SSU-Spl Lead | BiP | CAT | — | — | — | — | — | ba Tub IR | BSD | ba Tub IR-3' SSU | 0.27 | 0.64 | 70 | secreted |
| 8 | 5' SSU-Spl Lead | BiP | CAT | GPI | — | — | — | — | ba Tub IR | BSD | ba Tub IR-3' SSU | 3.6 | 0.29 | 7 | surface expr. |
| 9 | 5' SSU-Spl Lead | BiP | CAT | — | ba Tub IR | BiP | CAT | — | ba Tub IR | BSD | ba Tub IR-3' SSU | 3.1 | — | 54 | |
| 10 | 5' SSU-Spl Lead | BiP | CAT | GPI | ba Tub IR | BiP | CAT | GPI | ba Tub IR | BSD | ba Tub IR-3' SSU | 3.6 | — | 2 | |

7.5, Results and Conclusions from CAT Expression by Various Recombinant *T. theileri* Parasites The tested IR regions were all competent for RNA processing resulting in protein expression, and good levels of heterologous antigen expression and an average of 45 ng antigen/10^6 parasites was obtained from the *T. theileri* 18S SSU rRNA gene locus. It was noted that the upstream expression site in these constructs showed somewhat lower protein levels than the downstream expression site(s); a similar effect was also noted for insertions in the tubulin IR locus. Also some variations in the levels of secreted CAT protein were noted, which probably resulted from a process or normal cell death/lysis, even though the parasite cultures all looked normal.

The secretion level seemed to fluctuate around 20-25% in most cases tested, although there were outliers: CAT Expression in the absence of any trafficking signals resulted in about 38% of the expressed antigen being released into the cell culture medium (either by active secretion, or through release from dying cells). The addition of specific trafficking signals was successful in directing the heterologous antigen within *T. theileri* for secretion (with the BiP protein N-terminus), or for surface expression (with the BiP protein N-terminus and a GPI-anchor addition sequence at the C-terminus).

As expected, the BiP fusion CAT protein was found predominantly in the cell culture media, displaying a much higher secretion rate (73%) than the untargeted construct (15-38%, for different clones tested). The GPI-anchored CAT protein, in contrast, was found almost exclusively (95%) to be cell-associated, indicating its presence on the cell surface. Total CAT protein expression levels were somewhat lower when trafficking signals were used; this may be due to a shorter half-life in the extracellular milieu in the case of the secreted protein, or due to spatial constraints, or surface protein turnover, in the case of the GPI-anchored protein.

7.6. Expression of the Bd37 Gene by Recombinant *T. theileri* Parasites

Recombinant *T. theileri* were generated that expressed the *Babesia divergens* Bd37 antigen from the 18S SSU rRNA gene locus. Different constructs were made and tested, having one or two Bd37 genes inserted upstream of the BSD gene, and the Bd37 gene was tested with or without trafficking signals. Also a "core" version of the Bd37 gene was tested, i.e. without its native N- and C-terminal hydrophobic sequences.

The resulting recombinant parasites were tested in vitro, by Northern blot and Elisa. Next, some of these recombinants were tested in vivo in bovine animals by inoculation and monitoring immune-responses.

Figure 17:

7.7. Northern Blotting of Recombinant *T. theileri* Parasites Expressing the Bd37 Antigen By similar method as described above, the recombinant *T. theileri* parasites expressing one or more Bd37 inserts (in addition to a BSD gene) were analysed by Northern blotting: DIG-labelled probes specific for the Bd37 gene were used. Results are presented in FIG. 17.

*T. theileri* recombinants tested were generated by transfection with the insertion cassettes comprised in the transfervectors: Lanes 2 and 3: p53Bd37, (two separate clones were tested); Lane 4: p53BiPBd37; Lane 5: p53BiPBd37GPI; Lane 6: p53BB tandem (vector map in FIG. 11); and Lane 7: p53BBG tandem.

Results indicated that all recombinants expressed the Bd37 gene(s), with sizes of the transcripts modified depending whether no signals were attached (FIG. 17, lanes 2 and 3), or an N-terminal BiP signal was attached (lanes 4 and 6), or both BiP and GPI were attached (lanes 5 and 7). Tandem expression constructs (lanes 6 and 7) generally showed increased expression levels.

7.8. Detection of Bd37 Seroresponse in Bovines, Using Elisa

The level of seroresponse by bovines inoculated with a recombinant *T. theileri* parasite expressing the Bd37 vaccine antigen, was monitored by an antibody Elisa. Alternatively, a competition Elisa was used to detect the quality of the seroresponse; in the competition test a second antibody (a mouse monoclonal antibody specific for Bd37 and known to be capable of providing passive immunity) was used to detect competition for binding to a standard amount of coated recombinant Bd37 antigen. A short description of both methods:

Recombinant (*E. coli*) expressed His-tagged Bd37 antigen was diluted to 5 μg per ml in coating buffer (coating buffer=0.01 M sodium carbonate pH 9.6), and 100 μl was coated in microtitre wells overnight at 37° C., packed against evaporation. The coating buffer was removed and 200 µl blocking buffer (3% w/v BSA in 10 mM PBS) was added, and incubated at 37° C. for 60 minutes. The plates were washed 3 times with 200 µl washing buffer (10 mM PBS, pH 9.6). Bovine serum samples were diluted in blocking buffer, and 100 µl were incubated in the coated wells (all subsequent incubation steps were carried out at 37° C. for 60 minutes). Next plates were washed, and in case of competition Elisa, incubated with 100 µl of Moab Bd37 diluted 1:1000 in blocking buffer and incubate. Next plates were washed and incubated with conjugated antibody: 100 µl of an HRP conjugated anti-bovine or -anti-mouse antibody respectively, and incubated. Plates are washed, stained with TMB substrate, stopped with sulfuric acid, and OD is measured at 450 nm in an ELISA reader.

Bd37 Elisa results are presented in the section on the animal trials.

8. Nested PCR Assays for Detection of *T. theileri*

Nested PCR assays were developed to sensitively monitor the presence of *T. theileri*; either the infection with recombinant *T. theileri* parasites in inoculated bovines, or the detection of any pre-existing infection with wildtype *T. theileri* in the experimental bovine animals.

8.1. General Procedures

Bovine blood samples we divided into 2, and DNA was extracted as described below. Next, these 2 samples were each assayed in duplo according to the nested PCR protocol described below. This gives a total of four assays of each blood sample.

The primer-sets used were either directed to a *T. theileri* Tubulin IR sequence to detect all *T. theileri*, recombinant and wildtype, or to a specific inserted gene, e.g. the Bd37 gene, to detect specific recombinants. The protocols used were the same except for the annealing temperatures.

The resulting PCR products were assessed by gel-electrophoresis on a 1% agarose gel according to standard techniques, which was stained with Ethidium Bromide, looking for a band of the correct size. A bovine blood sample was considered positive if 2 or more of the 4 assays showed a correct band.

The signal strength for the PCR product of the Tubulin IR was generally higher than that of the inserted gene, which matches the difference in number of target copies: many for Tubulin IR, and one or two (when the recombinant parasites had been transfected with the tandem construct) for the heterologous gene insert.

Because of variation in signal strength for the positive bands, the were only used for qualitative interpretation: positive-negative scoring. The variation observed resulted from the very small amounts of *T. theileri* genomic material present in the bovine blood samples tested.

8.2. DNA Isolation from Whole Blood for PCR:

The procedure was modified from literature (Higuchi R., "Rapid, efficient DNA extraction for PCR from cells or blood", in: Amplifcations: a forum for PCR users, Norwalk, Conn. ed., Perkin Elmer Cetus, 1989, vol. 2, p. 1-3). In short: 1 ml of whole bovine blood was collected in an EDTA-containing vacutainer. 500 µl lysis buffer (see below) was added to each tube and vortexed to suspend evenly. Samples were centrifuged for 30 s. at 16.000×g to pellet the nuclei. Next, supernatant was carefully pipetted off and discarded. The pellet was resuspended in lysis buffer. The extraction was repeated two more times, or until no haemoglobin remained and pellet appeared creamy white with no red. Then the pellets were resuspended in 100 µl PBND buffer with proteinase K (see below), and incubated at 55° C. for 60 min. Finally, samples were heated to 97° C. for 10 min. to inactivate the proteinase K. The crude extracted DNA was used directly in PCR reactions.

Lysis buffer consisted of: 0.32 M Sucrose; 10 mM Tris-HCl (pH 7.5); 5 mM $MgCl_2$; and 0.75% v/v Triton X-100.

PBND buffer (PCR Buffer with Nonionic Detergents) consisted of: 50 mM KCl; 10 mM Tris-HCl (pH 8.3); 2.5 mM $MgCl_2$; 0.1 mg/ml gelatine; 0.45% (v/v) Nonidet P40; and 0.45% (v/v) Tween 20. This was sterilised by autoclaving, which also dissolved the gelatine. Stocks were stored frozen. Immediately before use, per ml of PBND buffer, 0.5 µl of 60 µg/ml proteinase K was added.

8.3. Nested PCR Protocol:

For all first round PCRs, the PCR reaction was set up in a total volume of 25 µl with: 3 µl of extracted DNA Sample; 5 µl of 5× GoTaq Flexi® Buffer; 1.25 µl $MgCl_2$ (at 25 mM); 0.1 µl (at 100 mM) of each of the two first round primers; 0.25 µl of dNTP mixture (at 2 mM of each nucleotide); 0.25 µl of DNA polymerase (at 5 U/µl); and 15.5 µl double distilled water. The reagents used were from the GoTaq Flexi® DNA Polymerase kit (Promega, M8305).

Next the PCR Reaction was run on a Biometra T Professional Basic® PCR machine with the following settings: initially: 4 min. at 95° C., and next 35 cycles of: 45 s. 95° C.; 45 s. of annealing; and 45 s. at 72° C.; followed by a final 4 minutes at 72° C. The annealing temperatures were different for the different PCR assays: for detecting a *T. theileri* Tubulin IR sequence, annealing was done at 60° C., and for detecting the inserted Bd37 gene, annealing was at 67° C.

After the first round, 3 µl of the PCR reaction product was used in the second PCR reaction using a reaction mix similar to that for the first round, except that only 4.4 µl of 5×DNA Pol Buffer was used, and of course the PCR primers used were those for the $2^{nd}$ stage. The second stage PCR used the same PCR temperature cycling program.

Primers used for the nested PCR assays were:

| SEQ ID NO | Primer name | Sequence 5'->3 |
|---|---|---|
| 69 | Tub Diag F1 | agtagcaacgacagcagcagt |
| 70 | Tub Diag R1 | gtaaagtgtttgaagaagagctcg |
| 71 | Tub Diag F2 | cgattctcttcgcctgtttgt |
| 72 | Tub Diag R2 | actaaccgcgaccaaagaagt |
| 73 | Bd37 Diag F1 | atgaaaaccagtaagattctcaac |
| 74 | Bd37 Diag R1 | tgataccgaagacaatggcagaca |
| 75 | Bd37 Diag F2 | agcgaaggatggcttcttaggact |
| 76 | Bd37 Diag R2 | tcaacactgctgctatctgcctcc |

Figure 18:
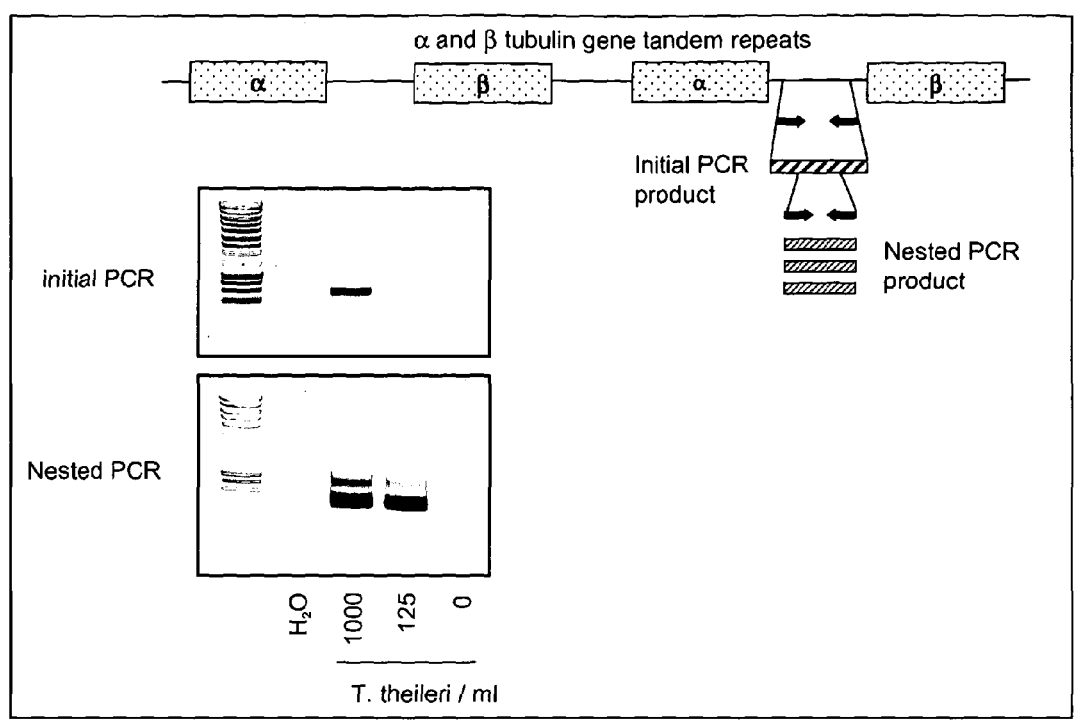

The set-up of the nested PCR assays for a *T. theileri* Tubulin IR, and initial results, are presented in FIG. 18. The increase in the assay's sensitivity going from the initial round to a nested $2^{nd}$ round stands out clearly.

The expected sizes of the PCR products are: for the Tubulin IR: $1^{st}$ round: 627 bp, and $2^{nd}$ round: 515 bp; and for the Bd37 gene insert: $1^{st}$ round: 887 bp and $2^{nd}$ round: 602 bp.

The specificity of the nested PCR for the Tubulin IR sequence was validated by testing known negative bovine cells: a cultured bovine MBDK cell line, to confirm that the screening was parasite specific. Also a herd of healthy farm cattle was tested, and infection with wildtype *T. theileri* was detected in 21 out of the 22 animals tested, even slightly higher than prevalence levels reported in literature.

The sensitivity of the nested PCR, in its optimised form as described, was such that it could routinely detect *T. theileri* parasites down to a level of about 10 per ml of the original sample; in the set up as described that means that from each original sample tested in fourfold, at least two assays needed to be positive to be counted. The sensitivity was validated by testing of mouse and bovine (parasite negative) blood samples that were spiked with known amounts of parasites.

9. Animal Trials Testing Recombinant *T. theileri* Parasites In Vivo

To test the feasibility and the efficacy of recombinant *T. theileri* expressing a heterologous nucleic acid inserted in their genome, animal trials in bovines were performed.

In one set-up, the efficacy of expression in vivo was tested, and because most of the experimental animals were *T. theileri* negative at the start of the experiment, this also provided information on the safety of the inoculation with recombinant *T. theileri*.

A follow up trial expanded on the positive findings, and used a different expression construct, a larger group of animals, with more animals that were *T. theileri* positive at the start of the experiment.

9.1. General Outline of $1^{st}$ Animal Trial

Recombinant *T. theileri* parasites expressing the Bd37 vaccine-antigen were prepared as described, by transfection with the insertion cassette from the transfervector p53BB Tandem (its vector map is presented in FIG. 11; the full sequence of this transfervector with annotation is presented in SEQ ID NO: 2). Stable recombinants were selected and amplified as described. These recombinants expressed the complete Bd37 vaccine-antigen from a tandem insert, each with an added N-terminal signal sequence directing secretion out of the parasite cell.

An animal trial (n=6) was performed in 6 weeks old calves, which ran for 13 weeks. The calves were kept in fly free level 2 containment facilities to prevent insect born natural infections. At 1 week prior to inoculation and at day zero, the calves were checked by nested PCR for any pre-existing *T. theileri* infection. At day zero, each calve was inoculated i.v. with $10^5$ recombinant *T. theileri* parasites expressing the tandem Bd37 vaccine antigens with N-terminal signal sequence. At day 16 one calve became ill with bacterial pneumonia unrelated to the experimental treatment, and was removed from the trial. At week 8 all remaining calves received a booster inoculation i.v. with $10^6$ of the same recombinant *T. theileri* parasites. At week 13 the trial was terminated.

All through the trial, and before its start, weekly blood samples were taken from all animals to monitor the presence of the recombinant *T. theileri* parasite by PCR, and detect the bovine's seroresponse to the Bd37 vaccine-antigen by Elisa as described.

9.2. PCR Results of $1^{st}$ Animal Trial

Figure 19:
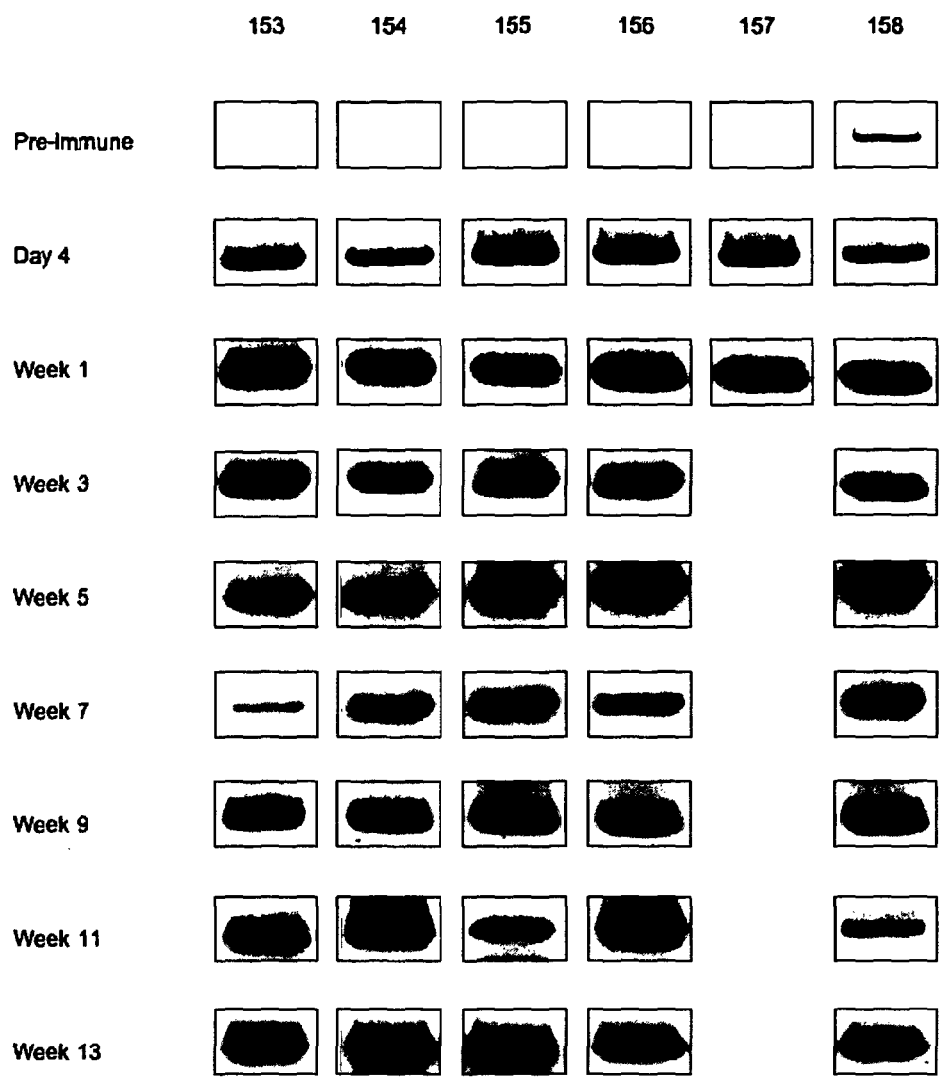
Figure 20:
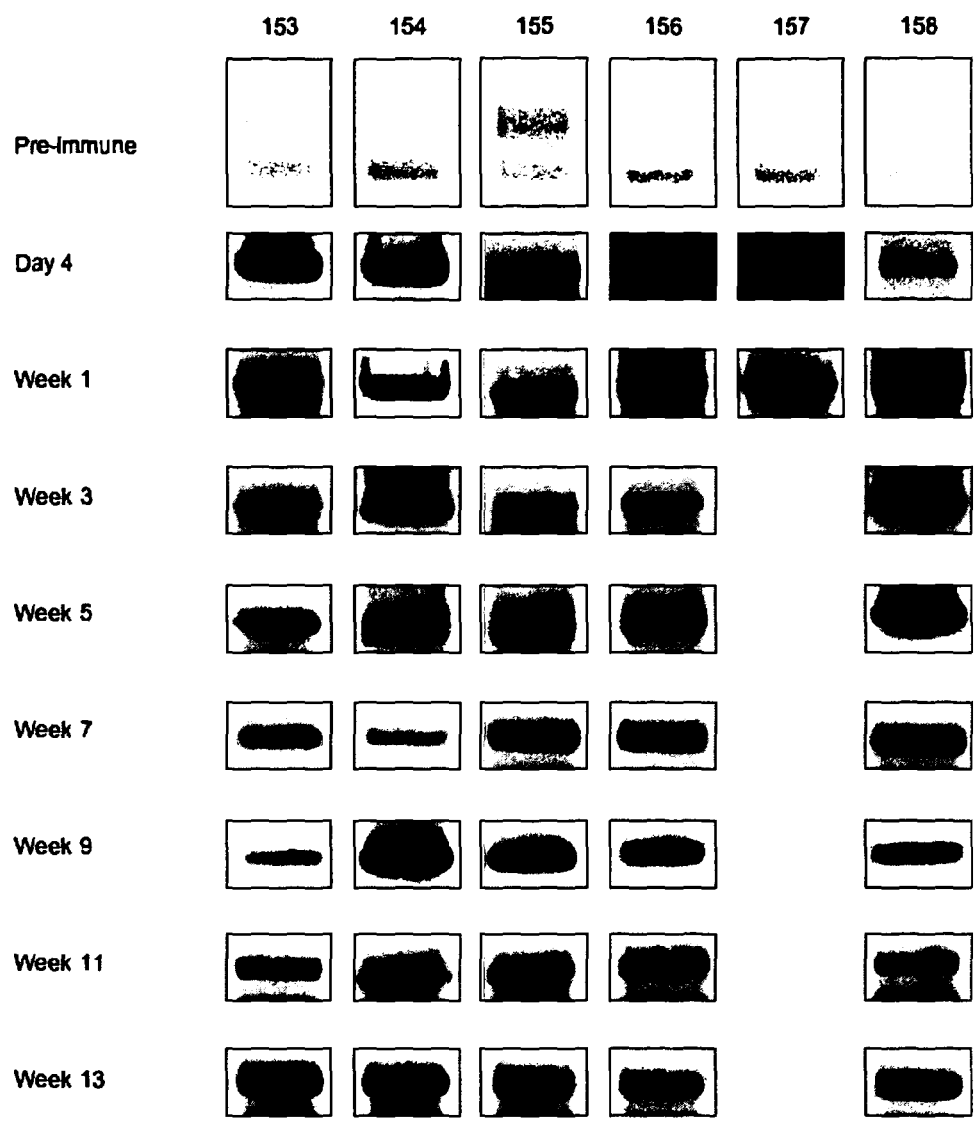

Nested PCR's were done at start and at regular intervals during the trial. Detection was for Tubulin IR, detecting all *T. theileri*, or for Bd37, detecting recombinant *T. theileri* parasites. Results are presented in FIGS. 19 and 20 respectively: only the location of the expected band is shown.

The results show that at the start of the trial, only calf 158 had a pre-existing *T. theileri* infection, which was non-recombinant as no animal had any reactivity with the Bd37 gene. All inoculated calves reacted positive from 4 days after inoculation, for *T. theileri*, and in particular for recombinant *T. theileri*. The infection with recombinant *T. theileri* parasites was maintained over the course of the trial up until week 13, and no animal cured itself of the infection.

9.3. Bd37 Elisa Results of $1^{st}$ Animal Trial

Serum samples collected before and during the animal trial were tested in the antibody Elisa and in competition Elisa.

Bd37 Antibody Elisa Results

Figure 21:
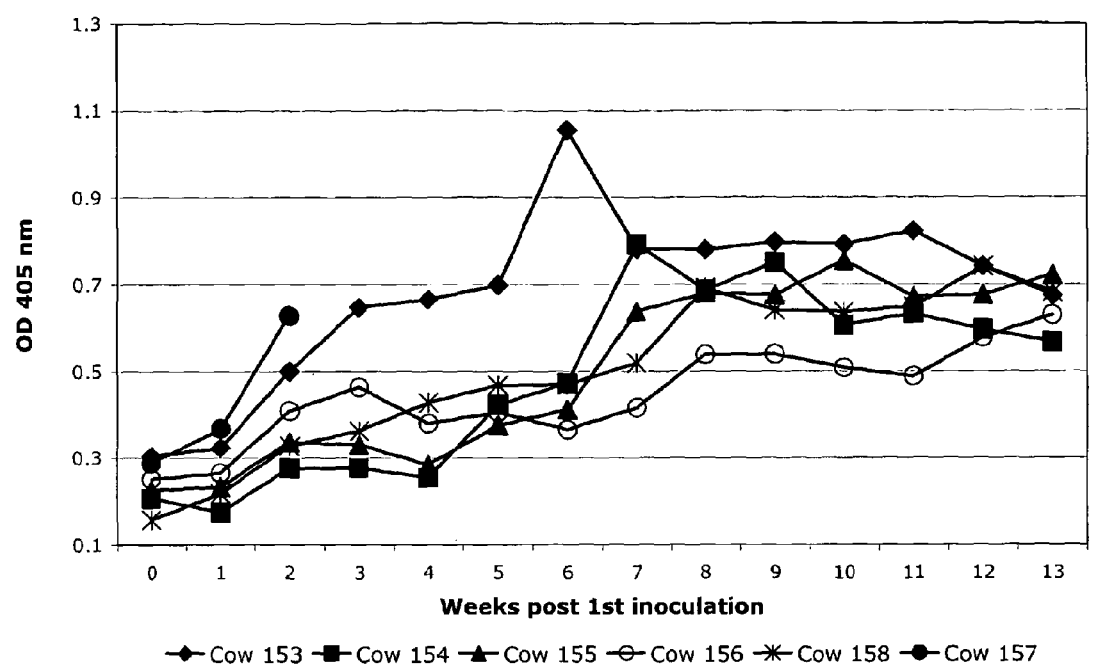

Results are presented in FIG. 21, and show that all animals seroconverted directly after inoculation, demonstrating the take of the recombinant *T. theileri* vaccination, and the feasibility of the *T. theileri* expression and delivery system.

Also calf 158 seroconverted, even though this had a pre-existing infection with wild type *T. theileri*.

Most notable was that while expression of the foreign Bd37 antigen continues, and the bovine host went through a specific seroconversion, nevertheless, the recombinant *T. theileri* does not get cleared by the host's immune system; on the contrary: the host's serum titres show a steady increase over the course of the experiment, indicating a sustained presence of the recombinant parasites, and a sustained expression of its heterologous insert to the bovine host animal.

At 8 weeks after the initial inoculation a booster inoculation was given. However no boost of the Bd37 specific antibody levels can be observed. Apparently an equilibrium level of *T. theileri* infection had already been established which was not increased.

Bd37 Competition Elisa Results

Figure 22:
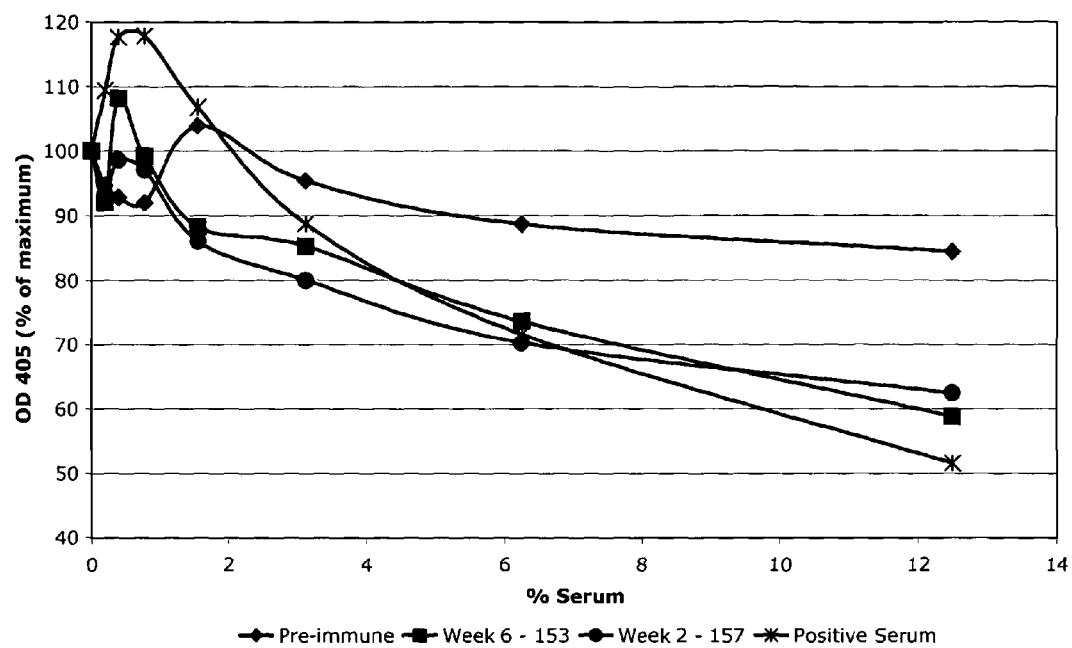

Results of the Bd37 competition Elisa are presented in FIG. 22; a positive anti-Bd37 (*E. coli* expressed) bovine serum, and a negative (pre-immune) bovine serum were included. Next, follow two samples from different animals in the trial.

As can be seen from the results, in the samples with low amounts of blocking sera there was some signal interference, leading to absorbance values above the 100% level (100% being the unblocked maximal binding level of the anti-Bd37 MoAb to the coated Bd37 protein). This cleaned out, as blocking increased.

All sera that contained Bd37 antibody were able to compete increasingly for binding at higher serum concentrations. The pre-immune serum had a noticeably lesser effect, hardly different from the levels at the lowest concentrations, which were considered negative.

The mouse monoclonal antibody that the bovine sera competed with, had been demonstrated to be effective in providing Gerbils a protective passive immunity against *B. divergens* challenge (Precigout, E. et al., 2004, Int. J. for Parasitol. vol. 34, p. 585-593; and Hadj-Kadour 2007, supra). Consequently it was concluded that the bovine antibodies that were induced, at the levels that were obtained, were equally protective against *B. divergens* challenge.

9.4. General Outline of $2^{nd}$ Animal Trial

To expand on the positive results of the animal trial described, an extended animal trial was initiated. This further studied the effect of the trafficking of the expressed heterologous insert, on the immune-response generated in the bovine host. Therefore recombinant *T. theileri* were generated using transfervector: p53Bd37core XmaI (FIG. 12); the resulting recombinant *T. theileri* parasites thus express the Bd37 antigen without N- or C-terminal hydrophobic sequences, so that expression built up inside the parasite.

2nd Animal Trial Protocol:

A group of 12 calves of 6 weeks old was set aside, and tested for pre-existing *T. theileri* infection by jugular venapuncture, and nested PCR on whole blood. 4 of the 12 animals were found to be *T. theileri* positive. Prior to housing in the containment facilities the calves were treated with Danafloxacin (anti-bacterial) and an insecticide. Calves were divided into two groups, each receiving 10^5 i.v. of the recombinant *T. theileri*. The take of the inoculation was monitored at day 2, 5 and 7 post-inoculation. The possibility for re-inoculation with a repeated, or an increased dose was calculated in, but appeared unnecessary as all animals reacted positive for recombinant *T. theileri* at day 7 p.i. The inoculated animals are being monitored to follow persistence of parasitaemia and establishment of antibody responses to the heterologous antigen, up to 12 weeks after initial inoculation.

The animals will be blood sampled (20 ml) every 7 days to monitor dynamics of infection and any antigen-specific antibody responses induced. Parasites will be expanded from sampled blood by in vitro culture to monitor continued expression of the expressed heterologous antigen by the TG parasites. At the time of sacrifice an additional 500 ml sample of blood will be taken in addition to normal samples for the purposes of producing a large quantity of serum.

LEGEND TO THE FIGURES

FIG. 1:

Graphical representation of various insertion cassettes used for the invention.

FIG. 2:

Growth rate of *T. theileri* parasites in in vitro culture at different starting densities. Error bars indicate a 5% confidence interval.

FIG. 3:

Map of transfervector pabEABSDba, comprising eGFP and BSD ORF's, flanked by RNA processing signals, and inserted in between targeting regions for insertion into the Tubulin IR region on the *T. theileri* genome.

FIG. 4:

Map of transfervector pabCTBba, comprising CAT and BSD ORF's, flanked by RNA processing signals, and inserted in between targeting regions for insertion into the Tubulin IR region on the *T. theileri* genome; the sequence is provided in SEQ ID NO: 1.

FIG. 5:

Map of transfervector p5'3' CAB, comprising CAT and BSD ORF's, flanked by RNA processing signals, with the Actin IR Splice leader acceptor site (SL) preceding the CAT gene, and the complete actin IR sequence in between the two coding genes; the whole is inserted in between targeting regions for insertion into the 18S SSU rRNA gene on the *T. theileri* genome.

FIG. 6:

Map of transfervector p5'3'BTC, comprising CAT and BSD ORF's, wherein BSD is in the upstream expression position. The genes are flanked by RNA processing signals, with the Actin IR Splice leader acceptor site preceding the BSD gene, and the beta-alpha Tubulin IR sequence in between the two coding genes; the whole is inserted in between targeting regions for insertion into the 18S SSU rRNA gene on the *T. theileri* genome.

FIG. 7:

Map of transfervector p5'3' BiPCAT, comprising CAT and BSD ORF's, flanked by RNA processing signals, and inserted in between targeting regions for insertion into the 18S SSU rRNA gene on the *T. theileri* genome. The CAT gene additionally was provided with an upstream trafficking signal (BiP).

FIG. 8:

Map of transfervector p5'3' BiPCATGPI, comprising CAT and BSD ORF's, flanked by RNA processing signals, and inserted in between targeting regions for insertion into the 18S SSU rRNA gene on the *T. theileri* genome. The CAT gene additionally was provided with upstream (BiP) and downstream (GPI) trafficking signals.

FIG. 9:

Map of transfervector p5'3' BC Tandem, comprising CAT and BSD ORF's, flanked by RNA processing signals, and inserted in between targeting regions for insertion into the 18S SSU rRNA gene on the *T. theileri* genome. The CAT gene additionally was provided with an upstream trafficking signal (BiP), and the whole BiP-CAT construct was duplicated and inserted in tandem.

FIG. 10:

Map of transfervector p5'3' BCG Tandem, comprising CAT and BSD ORF's, flanked by RNA processing signals, and inserted in between targeting regions for insertion into the 18S SSU rRNA gene on the *T. theileri* genome. The CAT gene additionally was provided with upstream (BiP) and downstream (GPI) trafficking signals, and the whole BiP-CAT-GPI construct was duplicated and inserted in tandem.

FIG. 11:

Map of transfervector p5'3' BB Tandem Xma, comprising Bd37 and BSD ORF's, flanked by RNA processing signals, and inserted in between targeting regions for insertion into the 18S SSU rRNA gene on the *T. theileri* genome. The Bd37 gene additionally was provided with an upstream trafficking signal (BiP), and the whole BiP-Bd37 construct was duplicated and inserted in tandem; the sequence is provided in SEQ ID NO: 2.

FIG. 12:

Map of transfervector p5'3' Bd37 Core XmaI, comprising Bd37 and BSD ORF's, whereby the Bd37 gene was cleared from N- and C-terminal hydrophobic sequences (hence: "core"). ORF's are flanked by RNA processing signals, and inserted in between targeting regions for insertion into the 18S SSU rRNA gene on the *T. theileri* genome.

FIG. 13:

Map of transfervector p5'3' BB Core Tandem XmaI, comprising the Bd37-core and BSD ORF's, flanked by RNA processing signals, and inserted in between targeting regions for insertion into the 18S SSU rRNA gene on the *T. theileri* genome. The Bd37-core ORF additionally was provided with an upstream trafficking signal (BiP), and the whole BiP-Bd37-core construct was duplicated and inserted in tandem.

FIG. 14:

Map of transfervector p5'3' BBG Core Tandem XmaI, comprising the Bd37-core and BSD ORF's, flanked by RNA processing signals, and inserted in between targeting regions for insertion into the 18S SSU rRNA gene on the *T. theileri* genome. The Bd37-core ORF additionally was provided with upstream (BiP) and downstream (GPI) trafficking signals, and the whole BiP-Bd37-core-GPI construct was duplicated and inserted in tandem.

FIG. 15:

Results from expression by recombinant *T. theileri* of heterologous genes from the Tubulin IR locus: expression of eGFP (left panels), and ACE proteins (right panels); with both lower panels presenting images from agarose gels stained with Ethidium bromide, showing the total RNA that was loaded and run, before the gel was blotted. The upper panels present the results of Northern blotting for eGFP (left) and sACE-1 (right). The three lanes for the eGFP expression represent three identical, but individually isolated, recombinants; 'wt' are RNA samples from wildtype *T. theileri* parasites.

FIG. 16:

Results from expression by recombinant *T. theileri* of the CAT gene from the Tubulin IR locus.

Top two panels: results of Northern blots for CAT expression by three different recombinant constructs, that differ in the IR sequence that was incorporated in between the CAT and the BSD gene; IR sequences used were from Actin IR, PFR IR, and beta-alpha Tubulin IR (last: see FIG. 4). The top most panel represents the BSD expression levels of these recombinants.

Figure 4:
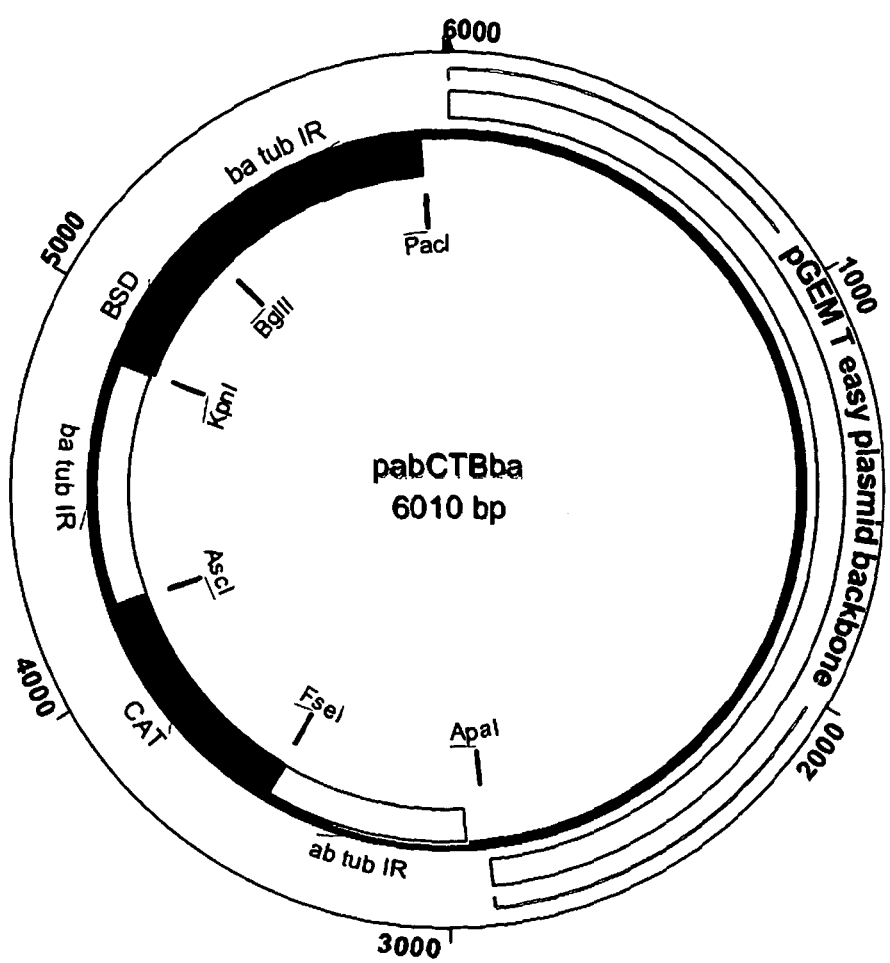
Figure 5:
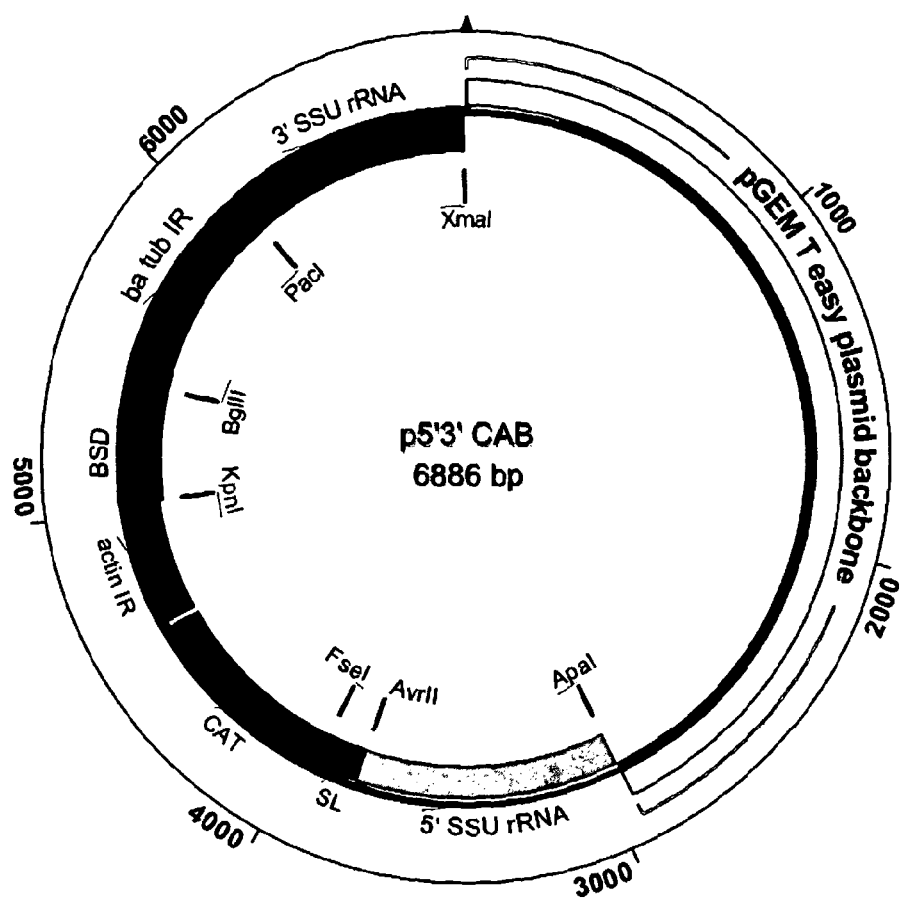
Figure 6:
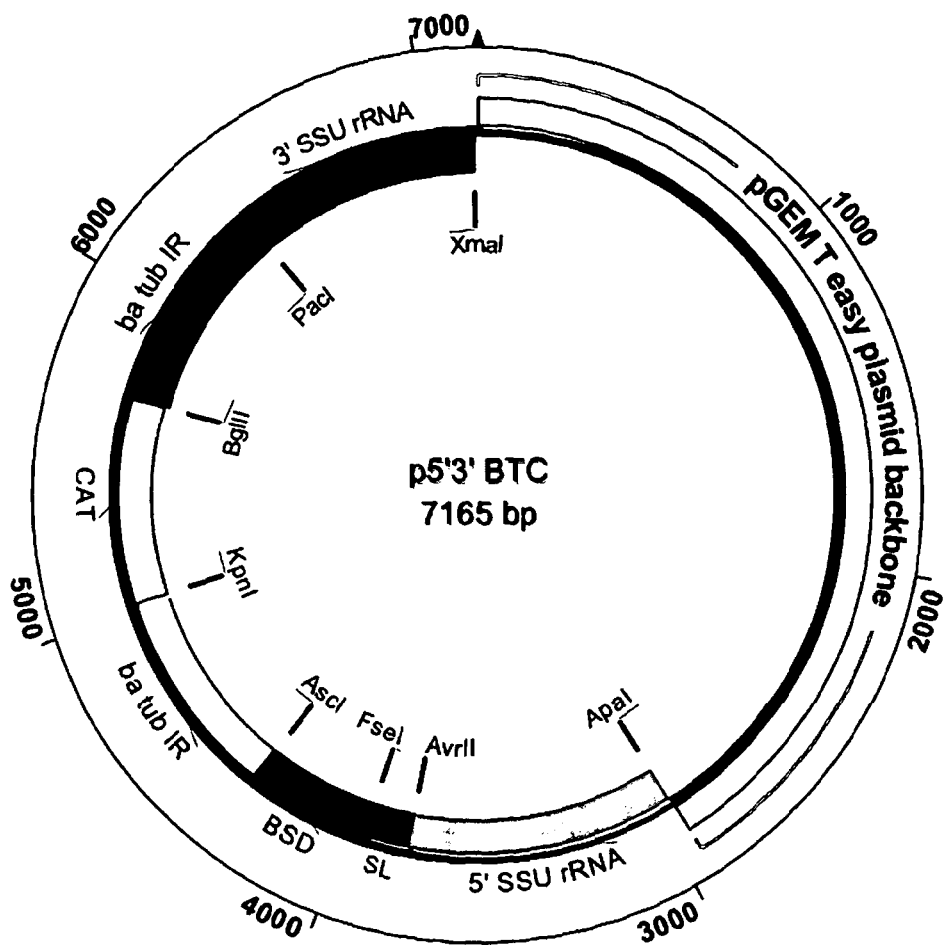
Figure 7:
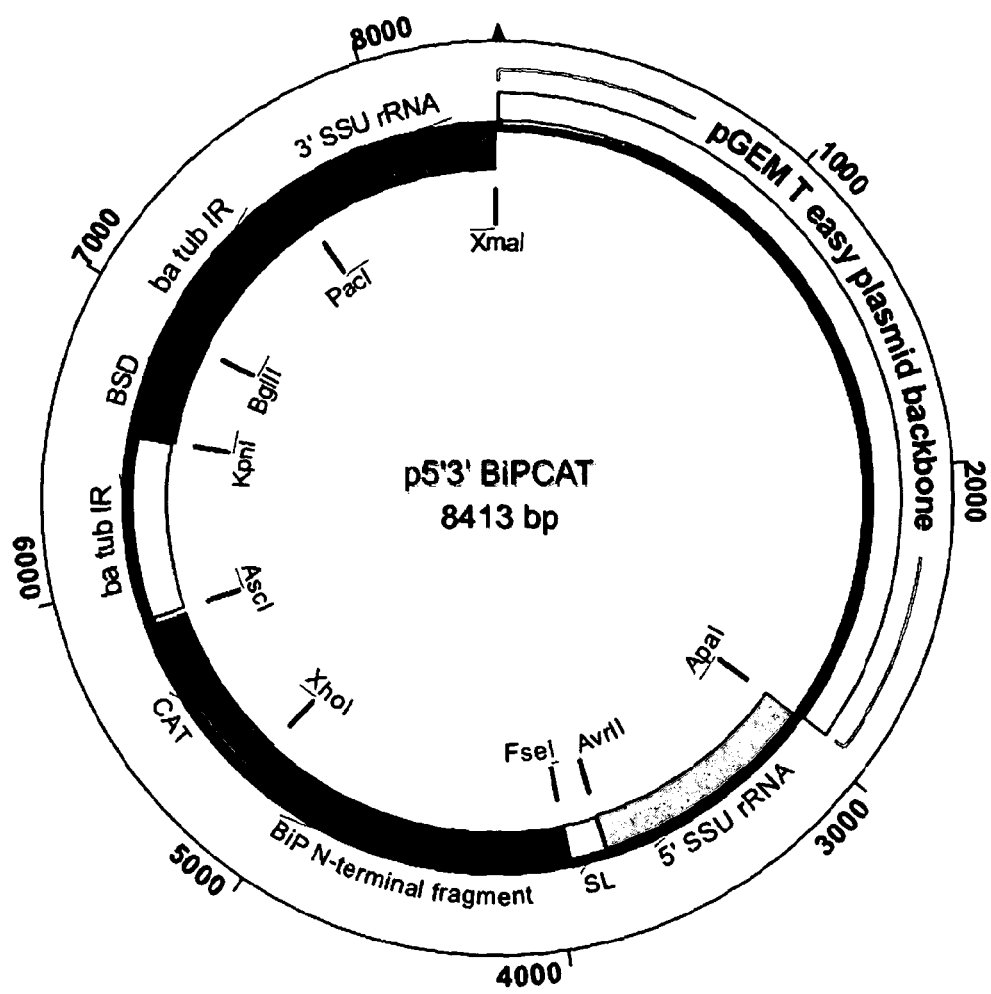
Figure 8:
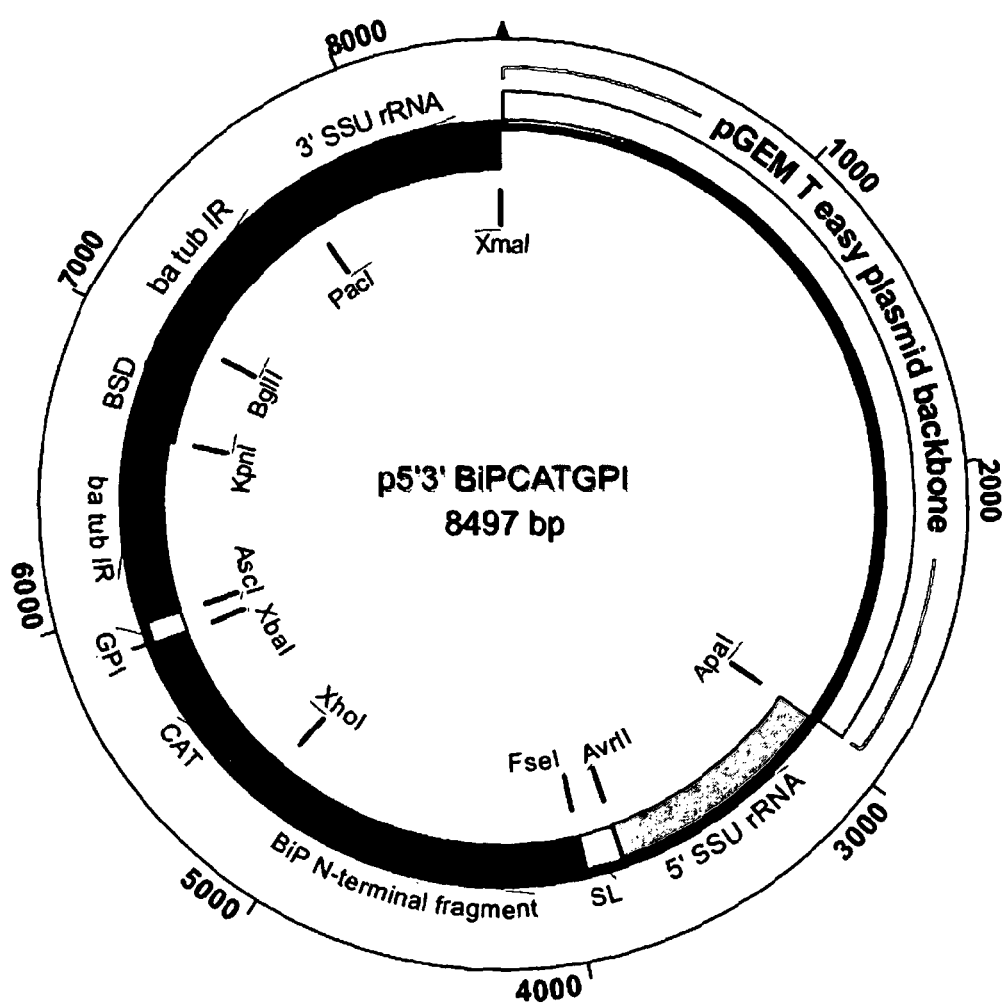
Figure 9:
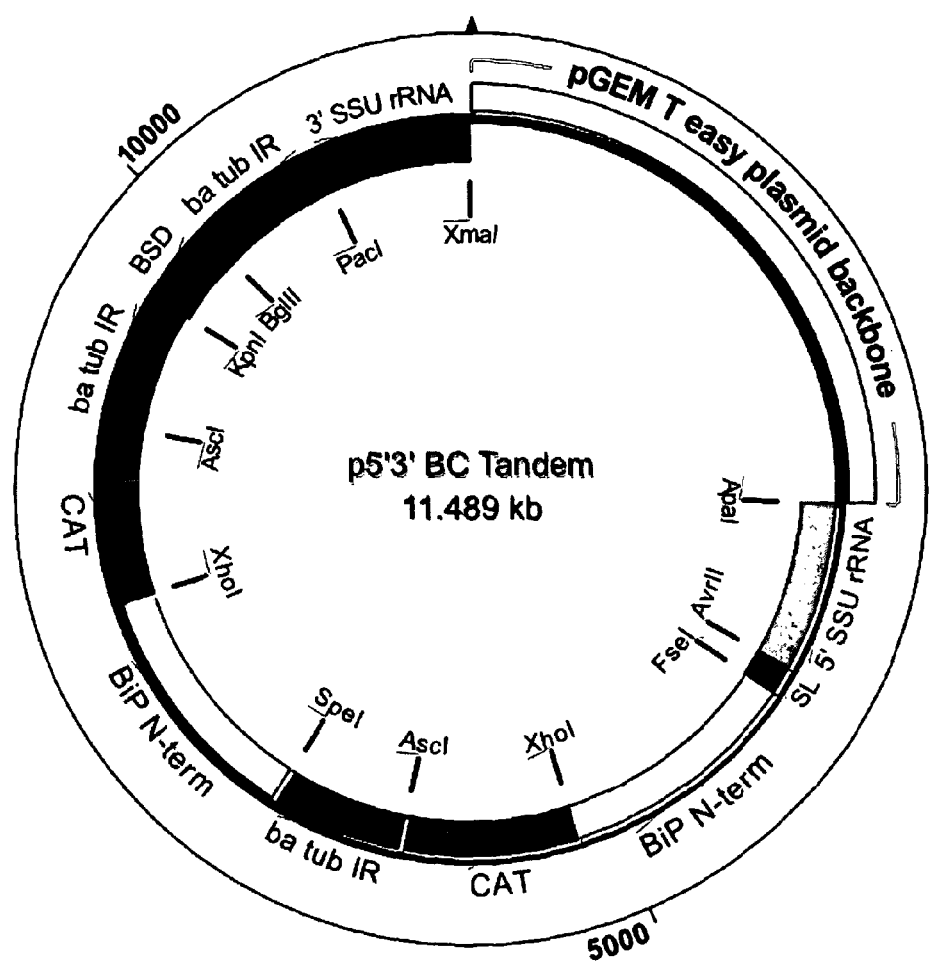
Figure 10:
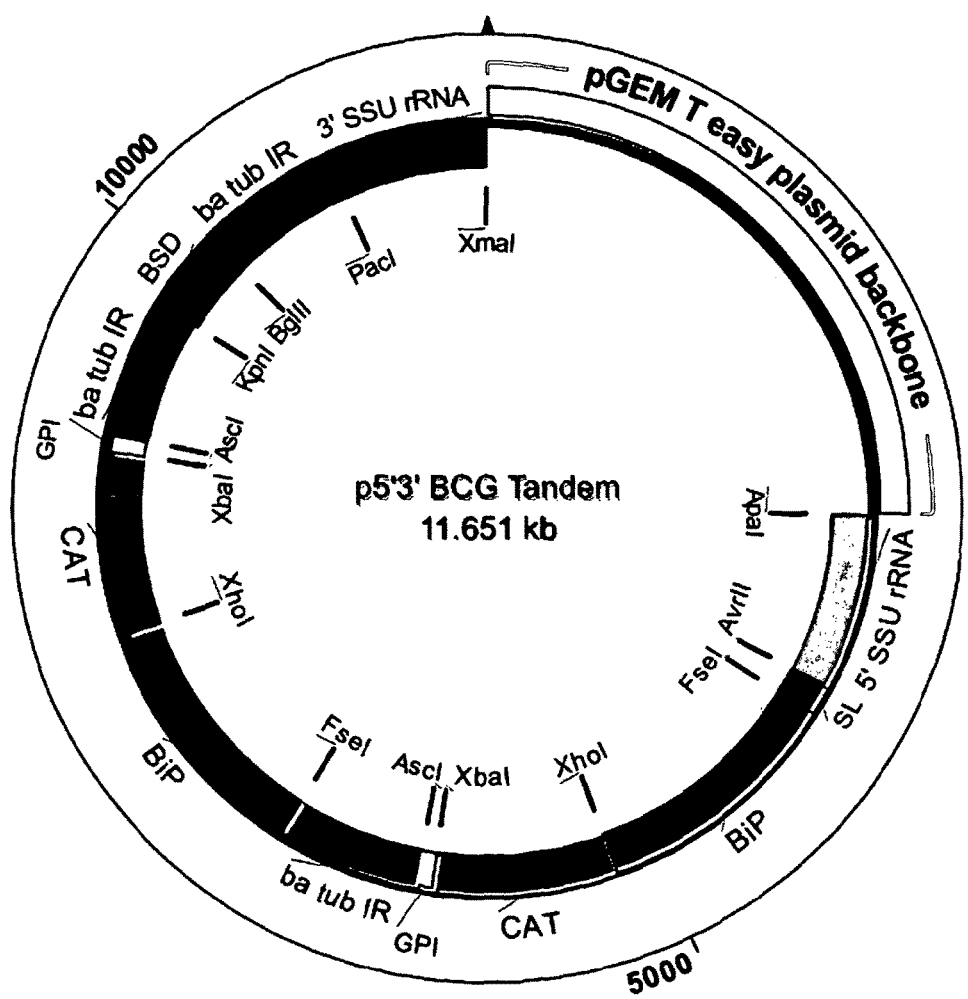

The bottom graph displays the results of an Elisa detecting CAT protein expression, for a negative control, and a CAT expressing recombinant *T. theileri*, produced from the pabCTBba transfervector (FIG. 4, and SEQ ID NO: 1).

Error bars indicate a 5% confidence interval.

FIG. 17:

Northern blot results detecting Bd37 mRNA from recombinant *T. theileri* parasites expressing one or more copies of the Bd37 vaccine antigen gene from the 18S SSU rRNA genome locus.

Lane 1: Parental line, un-transfected
Lane 2: *T. theileri* recombinant generated from transfervector p53Bd37-clone 1 (vector resembling that of FIG. 5, but with Bd37 in stead of CAT gene)
Lane 3: idem from vector p53Bd37-clone 2 (idem lane 2)
Lane 4: idem from vector p53BiPBd37 (vector resembling that of FIG. 7)

Lane 5: idem from vector p53BiPBd37GPI (vector resembling that of FIG. 8)

Lane 6: idem from vector p53BB tandem (FIG. 11)

Lane 7: idem from vector p53BBG tandem (vector resembling that of FIG. 10)

FIG. 18:

Outline and results of a nested PCR assay for the detection of all *T. theileri* parasites, via amplification of a *T. theileri* Tubulin IR sequence.

Left and left-bottom panels representing Eth.Br. stained agarose gels with PCR products from initial first PCR round, and from second nested PCR round.

Left most lane: molecular weight marker (sizes from bottom to top: 200, 400, 600, 800, and 1000 bp). Subsequent lanes: $H_2O$=negative control sample with water; and subsequently three lanes with respectively 1000, 125 or zero *T. theileri* parasites per ml of bovine blood.

FIG. 19 and FIG. 20:

Nested PCR's on recombinant parasites from animal trial; detection was of Tubulin IR, detecting all *T. theileri* (FIG. 19), or of the Bd37 gene insert, detecting recombinant *T. theileri* parasites (FIG. 20). Only the location of the expected band is shown.

FIG. 21:

Results of the Elisa detecting Bd37 antibodies produced in the calves during the course of the animal trial. Absorbance levels indicate presence of bound bovine antibody.

FIG. 22:

Results of the competition Elisa detecting Bd37 antibodies produced in the calves during the course of the animal trial. Increasing amounts of the animal test sera competed for binding to coated Bd37 antigen, with a Bd37 specific Moab. Absorbance levels indicate presence of bound murine antibody.

The invention claimed is:

1. A method for the sustained delivery of a heterologous protein to a bovine animal, said method comprising the inoculation of said bovine animal with a sustained delivery vector comprising a recombinant live *T. theileri* parasite, so as to achieve the sustained presence of the recombinant live *T. theileri* parasite, wherein the recombinant live *T. theileri* parasite comprises an additional nucleic acid sequence comprising from outside towards the centre:

restriction enzyme (RE) recognition sites;

inward from the RE sites, flanking target regions from the *T. theileri* genome;

internal to the target regions and flanking the central portion, signal sequences for RNA processing selected from the group consisting of SEQ ID NOS: 11-13, 20, 22 and 23; and centrally, at least one heterologous gene encoding at least one heterologous protein and nucleotides 4934 through 5326 from SEQ ID NO: 1 encoding a protein that provides resistance to blasticidin, and wherein the expression and delivery of the heterologous protein by the recombinant *T. theileri* parasite continues in a sustained way from the moment of inoculation of the bovine animal with the recombinant parasite, to as long as the parasite survives.

2. The method of claim 1, wherein the heterologous protein is a protein or protein-fragment selected from the group consisting of: an antigen, a cytokine, a hormone, an antimicrobial protein or an antibody.

3. The method of claim 1, wherein the method comprises inoculating said bovine animal with two or more different recombinant *Trypanosoma theileri* parasites.

\